US008809293B2

(12) United States Patent
Chin et al.

(10) Patent No.: US 8,809,293 B2
(45) Date of Patent: Aug. 19, 2014

(54) COMPOSITIONS AND METHODS FOR INHIBITING GENE EXPRESSION OF HEPATITIS B VIRUS

(75) Inventors: Daniel Chin, Bloomfield, NJ (US);
 Jochen Deckert, Kulmbach (DE);
 Markus Hossbach, Kulmbach (DE);
 Matthias John, Hallstadt (DE)

(73) Assignee: Arrowhead Madison Inc., Madison, WI (US)

( * ) Notice: Subject to any disclaimer, the term of this patent is extended or adjusted under 35 U.S.C. 154(b) by 48 days.

(21) Appl. No.: 13/535,454

(22) Filed: Jun. 28, 2012

(65) Prior Publication Data

US 2013/0005793 A1 Jan. 3, 2013

(30) Foreign Application Priority Data

Jun. 30, 2011 (EP) .................................. 11172235

(51) Int. Cl.
 *C12N 15/11* (2006.01)
 *A61K 48/00* (2006.01)
 *C07H 21/02* (2006.01)
 *C07H 21/04* (2006.01)

(52) U.S. Cl.
 USPC ........................................ 514/44 A; 536/24.5

(58) Field of Classification Search
 USPC ........................................ 514/44 A; 536/24.5
 See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts'o et al. |
| 5,023,243 | A | 6/1991 | Tullis |
| 5,034,506 | A | 7/1991 | Summerton et al. |
| 5,134,066 | A | 7/1992 | Rogers et al. |
| 5,212,295 | A | 5/1993 | Cook |
| 5,214,134 | A | 5/1993 | Weis et al. |
| 5,216,141 | A | 6/1993 | Benner |
| 5,218,105 | A | 6/1993 | Cook et al. |
| 5,264,423 | A | 11/1993 | Cohen et al. |
| 5,264,562 | A | 11/1993 | Matteucci |
| 5,321,131 | A | 6/1994 | Agrawal et al. |
| 5,359,044 | A | 10/1994 | Cook et al. |
| 5,399,676 | A | 3/1995 | Froehler |
| 5,405,939 | A | 4/1995 | Suhadolnik et al. |
| 5,453,496 | A | 9/1995 | Caruthers et al. |

(Continued)

FOREIGN PATENT DOCUMENTS

| | | |
|---|---|---|
| EP | 1752536 | 2/2007 |
| WO | 91/06309 | 5/1991 |

(Continued)

OTHER PUBLICATIONS

Elbashir et al. (The EMBO Journal, 2001 vol. 20, No. 23:6877-6888).*

(Continued)

*Primary Examiner* — Terra Cotta Gibbs
(74) *Attorney, Agent, or Firm* — Kirk Ekena

(57) ABSTRACT

The invention relates to a double-stranded ribonucleic acid (dsRNA) for inhibiting the expression of a Hepatitis B Virus gene. The invention also relates to a pharmaceutical composition comprising the dsRNA or nucleic acid molecules or vectors encoding the same together with a pharmaceutically acceptable carrier; methods for treating diseases caused by Hepatitis B Virus infection using said pharmaceutical composition; and methods for inhibiting the expression of a Hepatitis B Virus gene in a cell.

17 Claims, 38 Drawing Sheets

(56) References Cited

U.S. PATENT DOCUMENTS

| | | | |
|---|---|---|---|
| 5,455,233 | A | 10/1995 | Spielvogel et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,489,677 | A | 2/1996 | Sanghvi et al. |
| 5,506,351 | A | 4/1996 | McGee |
| 5,519,134 | A | 5/1996 | Acevedo et al. |
| 5,521,302 | A | 5/1996 | Cook |
| 5,539,082 | A | 7/1996 | Nielsen et al. |
| 5,541,307 | A | 7/1996 | Cook et al. |
| 5,552,540 | A | 9/1996 | Haralambidis |
| 5,554,746 | A | 9/1996 | Ravikumar et al. |
| 5,571,902 | A | 11/1996 | Ravikumar et al. |
| 5,578,718 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,646,265 | A | 7/1997 | McGee |
| 5,663,312 | A | 9/1997 | Chaturvedula |
| 5,670,633 | A | 9/1997 | Cook et al. |
| 5,700,920 | A | 12/1997 | Altmann et al. |
| 6,127,533 | A | 10/2000 | Cook et al. |
| 6,166,197 | A | 12/2000 | Cook et al. |
| 6,172,209 | B1 | 1/2001 | Manoharan et al. |
| 6,262,241 | B1 | 7/2001 | Cook et al. |
| 6,271,358 | B1 | 8/2001 | Manoharan et al. |
| 2003/0124651 | A1 | 7/2003 | Pasupuleti |
| 2003/0206887 | A1 | 11/2003 | Morissay |
| 2005/0032733 | A1 | 2/2005 | MaSwiggen |
| 2008/0145346 | A1 | 6/2008 | Ng |

FOREIGN PATENT DOCUMENTS

| | | |
|---|---|---|
| WO | 93/07883 | 4/1993 |
| WO | 00/22113 | 4/2000 |
| WO | 00/31105 | 6/2000 |
| WO | 03/020931 | 3/2003 |
| WO | 2005/065719 | 7/2005 |
| WO | 2005/116204 | 12/2005 |
| WO | 2006/017932 A1 | 2/2006 |
| WO | 2010/135322 | 11/2010 |
| WO | 2011/003780 | 1/2011 |

OTHER PUBLICATIONS

Akhtar S et al., "Nonviral delivery of synthetic siRNAs in vivo," Journal of Clinical Investigation (2007) 117: 3623-3632.
Atherton E et al., "The Fluorenylmethoxycarbonyl Amino Protecting Group" The Peptides, S. Udenfriend, J. Meienhofer, Eds., Academic Press, Inc. (1987) 9: 1-38.
Berkner KL et al., "Development of adenovirus vectors for the expression of heterologous genes," BioTechniques (1988) 6: 616-629.
Bucchini D et al., "Pancreatic expression of human insulin gene in transgenic mice," Proc. Natl. Acad. Sci. USA (1986) 83: 2511-2515.
Cook PD, "Medicinal Chemistry of Antisense Oligonucleotides-Future Opportunities." Anti-Cancer Drug Design (1991) 6: 585-607.
Chen S-H et al. "Gene therapy for brain tumors: Regression of experimental gliomas by adenovirus-mediated gene transfer in vivo," Proc. Natl. Acad. Sci. USA (1994) 91: 3054-3057.
Cone RD et al., "High-efficiency gene transfer into mammalian cells: Generation of helper-free recombinant retrovirus with broad mammalian host range," Proc. Natl. Acad. Sci. USA (1984) 81: 6349-6353.
Cornetta K et al., "Safety issues related to retroviral-mediated gene transfer in humans," Human Gene Therapy (1991) 2: 5-14.
Crooke et al., "Pharmacokinetic Properties of Several Novel Oligonucleotide Analogs in Mice." J. Pharmacal. Exp. Ther. (1996), 277: 923-927.
Danos O et al., "Safe and efficient generation of recombinant retroviruses with amphotropic and ecotropic host ranges," Proc. Natl. Acad. Sci. USA (1988) 85: 6460-6464.
Delgado C et al., "The Uses and Properties of PEG-Linked Proteins," Critical Reviews in Therapeutic Drug Carrier Systems (1992) 9(3,4): 249-304.
Docherty K et al., "Nutrient regulation of insulin gene expression," FASEB J. (1994) 8:20-24.
Englisch U et al., "Chemically Modified Oligonucleotides as Probes and Inhibitors," Angewandte Chemie, International Edition (1991) 30(6): 613-629.
Gassmann M et al., "Maintenance of an extrachromosomal plasmid vector in mouse embryonic stem cells," Proc. Natl. Acad. Sci. USA (1995) 92: 1292-1296.
Kroschwitz JL, "Monomers," Encyclopedia of Polymer Science and Engineering, John Wiley & Sons, New York, pp. 715-727.
Greene et al. Protective Groups in Organic Synthesis, Chapter 2, 2d ed., John Wiley & Sons, New York, 1991, and Oligonucleotides and Analogues a Practical Approach, Ekstein, F. Ed., IRL Press, N.Y, 1991.
Guzaev AP et al., "A Conformationally Preorganized Universal Solid Support for Efficient Oligonucleotide Synthesis," J. Am. Chem. Soc. (2003) 125: 2380-2381.
Hamm ML et al., "Incorporation of 2'-Deoxy-2'-mercaptocytidine into Oligonucleotides via Phosphoramidite Chemistry," J. Org. Chem. (1997) 62: 3415-3420.
Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.
Kabanov et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.
Letsinger RL et al., "Cholesteryl-conjugated oligonucleotides: Synthesis, properties, and activity as inhibitors of replication of human immunodeficiency virus in cell culture," Proc. NatL Acad. Sci. USA (1989) 85: 5553-5556.
Li S et al., "Folate-Mediated Targeting of Antisense Oligodeoxynucleotides to Ovarian Cancer Cells," Pharmaceutical Research (1998) 15(10): 1540-1545.
Manoharan M et al., "Chemical Modifications to Improve Uptake and Bioavailability of Antisense Oligonucleotides," Ann. N.Y. Acad. Sci. (1992) 660: 306-309.
Manoharan M et al., "Introduction of a Lipophilic Thioether Tether in the Minor Groove of Nucleic Acids for Antisense Applications," Bioorg. & Med. Chem. Letters (1993) 3: 2765-2770.
Manoharan M et al., "Cholic Acid-Oligonucleotide Conjugates for Antisense Applications," Bioorg. Med. & Chem. Lett. (1994) 4: 1053-1060.
Manoharan M et al., "Oligonucleotide Conjugates: Alteration of the Pharmacokinetic Properties of Antisense Agents," Nucleosides & Nucleotides (1995) 14: 969-973.
Manoharan M et al., "Lipidic Nucleic Acids," Tetrahedron Letters (1995) 36: 3651-3654.
Manoharan M, "Oligonucleotide Conjugates as Potential Antisense Drugs with Improved Uptake, Biodistribution, Targeted Delivery, and Mechanism of Action," Antisense & Nucleic Acid Drug Devel. (2002) 12: 103-128.
Mishra RK et al., "Improved leishmanicidal effect of phosphorothioate antisense oligonucleotides by LDL-mediated delivery," Biochim. et Biophysica Acta (1995) 1264: 229-237.
Nawrot B et al., "Chemical and Structural Diversity of siRNA Molecules," Current Topics in Medicinal Chemistry (2006) 6: 913-925.
Nguyen T et al., "RNAi therapeutics: an update on delivery." Current Opinion in Molecular Therapeutics (2008) 10(2): 158-167.
Oberhauser et al., "Effective Incorporation of 2'-O-methyl-oligoribonucleotides Into Liposomes and Enhanced Cell Association Through Modification with Thiocholesterol," Nucl. Acids Research (1992) 20: 533-538.

(56) References Cited

OTHER PUBLICATIONS

Polushin NN et al., "Synthesis of Oligonucleotides Containing 2'-Azido- and 2'-Amino-2'-deoxyuridine Using Phosphotriester Chemistry," Tetrahedron Letters (1996) 37(19): 3227-3230.
Rosenfeld MA et al., "Adenovirus-mediated transfer of a recombinant alpha 1-antitrypsin gene to the lung epithelium in vivo," Science (1991) 252: 431-434.
Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.
Samukov VV et al., "2-(4-Nitrophenyl)sulfonylethoxycarbonyl (Nsc) Group as a Base-Labile α-Amino Protection for Solid Phase Peptide Synthesis," Tetrahedron Letters (1994) 35(42): 7821-7824.
Shea et al., "Synthesis, Hybridization Properties and Antiviral Activity of Lipid-oligodeoxynucleotide Conjugates," Nucl. Acids Research (1990) 18: 3777-3783.
Svinarchuk et al, "Inhibition of HIV proliferation in MT-4 cells by antisense oligonucleotide conjugated to lipophilic groups," Biochimie (1993) 75: 49-54.
Thomson JB et al., "Synthesis and Properties of Diuridine Phosphate Analogues Containing Thio and Amino Modifications," J. Org. Chem. (1996) 61: 6273-6281.
Wagner RW, "The state of the art in antisense research." Nature Medicine (1995) 1(11): 1116-1118.
Williams DJ et al., "Thermodynamic Comparison of the Salt Dependence of Natural RNA Hairpins and RNA Hairpins with Non-Nucleotide Spacers," Biochemistry (1996) 35: 14665-14670.
Zamboni, "Liposomal, Nanoparticle, and Conjugated Formulations of Anticancer Agents," Clin. Cancer Res. (2005) 11: 8230-8234.
Ikeda et al., "Ligand-Targeting Delivery of Therapeutic siRNA," Pharmaceutical Research (2006) 23: 1631-1640.
Rosenfeld MA et al., "In vivo transfer of the human cystic fibrosis transmembrane conductance regulator gene to the airway epithelium" Cell (1992) 68(1): 143-155.
Sanghvi, Antisense Research and Applications, (1993) Chapter 15, p. 289-302, Crooke ST and Lebleu B ed., CRC Press.
Genbank Accession Nos. AP007263, AB 602818, AB644286, and AB554024.
Zhang, Y-L et al "RNA Interference inhibits hepatitis B virus of different genotypes in vitro and in vivo." BMC Microbiol. 2010, vol. 10:214, p. 1-10.

\* cited by examiner

Table 1. Core sequences of dsRNAs targeting Hepatitis B Virus gene.

| SEQ ID NO | sense strand sequence (5'-3') | SEQ ID NO | antisense strand sequence (5'-3') |
|---|---|---|---|
| 1 | CAAGGUAUGUUGCCCGUUU | 157 | AAACGGGCAACAUACCUUG |
| 2 | CUGUAGGCAUAAAUUGGUA | 158 | TACCAAUUUAUGCCUACAG |
| 3 | UCUGCGGCGUUUUAUCAUA | 159 | UAUGAUAAAACGCCGCAGA |
| 3 | UCUGCGGCGUUUUAUCAUA | 160 | TAUGAUAAAACGCCGCAGA |
| 4 | ACCUCUGCCUAAUCAUCUC | 161 | GAGAUGAUUAGGCAGAGGU |
| 5 | UUUACUAGUGCCAUUUGUA | 162 | TACAAAUGGCACUAGUAAA |
| 6 | ACCUCUGCCUAAUCAUCUA | 163 | TAGAUGAUUAGGCAGAGGU |
| 7 | CUGUAGGCAUAAAUUGGUC | 164 | GACCAAUUUAUGCCUACAG |
| 8 | UGUCUGCGGCGUUUUAUCA | 165 | UGAUAAAACGCCGCAGACA |
| 8 | UGUCUGCGGCGUUUUAUCA | 166 | TGAUAAAACGCCGCAGACA |
| 9 | UACUAGUGCCAUUUGUUCA | 167 | UGAACAAAUGGCACUAGUA |
| 9 | UACUAGUGCCAUUUGUUCA | 168 | TGAACAAAUGGCACUAGUA |
| 10 | CAACUUUUCACCUCUGCA | 169 | TGCAGAGGUGAAAAAGUUG |
| 11 | CCAUUUGUUCAGUGGUUCG | 170 | CGAACCACUGAACAAAUGG |
| 12 | CCAAGUGUUUGCUGACGCA | 171 | UGCGUCAGCAAACACUUGG |
| 12 | CCAAGUGUUUGCUGACGCA | 172 | TGCGUCAGCAAACACUUGG |
| 13 | CCAUUUGUUCAGUGGUUCA | 173 | TGAACCACUGAACAAAUGG |
| 14 | UUUACUAGUGCCAUUUGUU | 174 | AACAAAUGGCACUAGUAAA |
| 15 | CACCUCUGCCUAAUCAUCA | 175 | TGAUGAUUAGGCAGAGGUG |
| 16 | CUGGCUCAGUUUACUAGUG | 176 | CACUAGUAAACUGAGCCAG |
| 17 | CAAGGUAUGUUGCCCGUUA | 177 | TAACGGGCAACAUACCUUG |
| 18 | CUGGCUCAGUUUACUAGUA | 178 | TACUAGUAAACUGAGCCAG |
| 19 | GAGGCUGUAGGCAUAAAUU | 179 | AAUUUAUGCCUACAGCCUC |
| 20 | CAGUUUACUAGUGCCAUUU | 180 | AAAUGGCACUAGUAAACUG |
| 21 | AGGUAUGUUGCCCGUUUGU | 181 | ACAAACGGGCAACAUACCU |
| 22 | UAUGUUGCCCGUUUGUCCA | 182 | UGGACAAACGGGCAACAUA |
| 23 | GAGGCUGUAGGCAUAAAUA | 183 | TAUUUAUGCCUACAGCCUC |
| 24 | GUCUGCGGCGUUUUAUCAU | 184 | AUGAUAAAACGCCGCAGAC |
| 25 | CAACUUUUCACCUCUGCC | 185 | GGCAGAGGUGAAAAAGUUG |
| 26 | CCGUGUGCACUUCGCUUCA | 186 | UGAAGCGAAGUGCACACGG |
| 26 | CCGUGUGCACUUCGCUUCA | 187 | TGAAGCGAAGUGCACACGG |
| 27 | UCAAGGUAUGUUGCCCGUA | 188 | TACGGGCAACAUACCUUGA |
| 28 | CAGUUUACUAGUGCCAUUA | 189 | TAAUGGCACUAGUAAACUG |
| 29 | UGGUGGACUUCUCUCAAUU | 190 | AAUUGAGAGAAGUCCACCA |
| 30 | AGGUAUGUUGCCCGUUUGA | 191 | TCAAACGGGCAACAUACCU |
| 31 | CUGCUCGUGUUACAGGCGG | 192 | CCGCCUGUAACACGAGCAG |
| 32 | UAUGUUGCCCGUUUGUCCU | 193 | AGGACAAACGGGCAACAUA |
| 33 | UCAAGGUAUGUUGCCCGUU | 194 | AACGGGCAACAUACCUUGA |
| 34 | UCUUAUCAACACUUCCGGA | 195 | UCCGGAAGUGUUGAUAAGA |
| 34 | UCUUAUCAACACUUCCGGA | 196 | TCCGGAAGUGUUGAUAAGA |

FIG. 1A

| 35 | CACCUCUGCCUAAUCAUCU | 197 | AGAUGAUUAGGCAGAGGUG |
|---|---|---|---|
| 36 | AUAAGAGGACUCUUGGACU | 198 | AGUCCAAGAGUCCUCUUAU |
| 37 | GUCUGCGGCGUUUUAUCAA | 199 | TUGAUAAAACGCCGCAGAC |
| 38 | GGCGCUGAAUCCCGCGGAC | 200 | GUCCGCGGGAUUCAGCGCC |
| 39 | CGCGUCGCAGAAGAUCUCA | 201 | UGAGAUCUUCUGCGACGCG |
| 40 | AAUGUCAACGACCGACCUU | 202 | AAGGUCGGUCGUUGACAUU |
| 41 | GCUCAGUUUACUAGUGCCA | 203 | UGGCACUAGUAAACUGAGC |
| 42 | UGGUGGACUUCUCUCAAUA | 204 | TAUUGAGAGAAGUCCACCA |
| 43 | AUCGCCGCGUCGCAGAAGA | 205 | UCUUCUGCGACGCGGCGAU |
| 44 | GCCAUUUGUUCAGUGGUUC | 206 | GAACCACUGAACAAAUGGC |
| 45 | CGAUCCAUACUGCGGAACU | 207 | AGUUCCGCAGUAUGGAUCG |
| 46 | UCACCUCUGCCUAAUCAUC | 208 | GAUGAUUAGGCAGAGGUGA |
| 47 | GUGGACUUCUCUCAAUUUU | 209 | AAAAUUGAGAGAAGUCCAC |
| 48 | GGGUCACCAUAUUCUUGGG | 210 | CCCAAGAAUAUGGUGACCC |
| 49 | GCCGCGUCGCAGAAGAUCU | 211 | AGAUCUUCUGCGACGCGGC |
| 50 | UCAAUCGCCGCGUCGCAGA | 212 | UCUGCGACGCGGCGAUUGA |
| 51 | UGGAUGUGUCUGCGGCGUU | 213 | AACGCCGCAGACACAUCCA |
| 52 | UACUGUUCAAGCCUCCAAG | 214 | CUUGGAGGCUUGAACAGUA |
| 53 | GUUUACUAGUGCCAUUUGU | 215 | ACAAAUGGCACUAGUAAAC |
| 54 | ACUAGUGCCAUUUGUUCAG | 216 | CUGAACAAAUGGCACUAGU |
| 55 | CCGCGUCGCAGAAGAUCUC | 217 | GAGAUCUUCUGCGACGCGG |
| 56 | UAUCUUAUCAACACUUCCG | 218 | CGGAAGUGUUGAUAAGAUA |
| 57 | GGCCAAAAUUCGCAGUCCC | 219 | GGGACUGCGAAUUUUGGCC |
| 58 | UUCACCUCUGCCUAAUCAU | 220 | AUGAUUAGGCAGAGGUGAA |
| 59 | CUCAGUUUACUAGUGCCAU | 221 | AUGGCACUAGUAAACUGAG |
| 60 | UGUUGCCCGUUUGUCCUCU | 222 | AGAGGACAAACGGGCAACA |
| 61 | UAGUGCCAUUUGUUCAGUG | 223 | CACUGAACAAAUGGCACUA |
| 62 | AGGCUGUAGGCAUAAAUUG | 224 | CAAUUUAUGCCUACAGCCU |
| 63 | AUGUGUCUGCGGCGUUUUA | 225 | UAAAACGCCGCAGACACAU |
| 63 | AUGUGUCUGCGGCGUUUUA | 226 | TAAAACGCCGCAGACACAU |
| 64 | ACUUCGCUUCACCUCUGCA | 227 | UGCAGAGGUGAAGCGAAGU |
| 65 | CGUGCACUUCGCUUCAC | 228 | GUGAAGCGAAGUGCACACG |
| 66 | GUGGUGGACUUCUCUCAAU | 229 | AUUGAGAGAAGUCCACCAC |
| 67 | UGUGUCUGCGGCGUUUUAU | 230 | AUAAAACGCCGCAGACACA |
| 68 | AAGGUAUGUUGCCCGUUUG | 231 | CAAACGGGCAACAUACCUU |
| 69 | UCAACGACCGACCUUGAGG | 232 | CCUCAAGGUCGGUCGUUGA |
| 70 | CAUAAGAGGACUCUUGGAC | 233 | GUCCAAGAGUCCUCUUAUG |
| 71 | GUCAACGACCGACCUUGAG | 234 | CUCAAGGUCGGUCGUUGAC |
| 72 | AUAUUCUUGGGAACAAGAG | 235 | CUCUUGUUCCCAAGAAUAU |
| 73 | UGCUCUGUUACAGGCGGG | 236 | CCCGCCUGUAACACGAGCA |
| 74 | CAAUCGCCGCGUCGCAGAA | 237 | UUCUGCGACGCGGCGAUUG |
| 75 | ACUGUUCAAGCCUCCAAGC | 238 | GCUGGAGGCUUGAACAGU |
| 76 | CGCCGCGUCGCAGAAGAUC | 239 | GAUCUUCUGCGACGCGGCG |

FIG. 1B

| | | | |
|---|---|---|---|
| 77 | CAUUUGUUCAGUGGUUCGU | 240 | ACGAACCACUGAACAAAUG |
| 78 | CGCUGAAUCCCGCGGACGA | 241 | UCGUCCGCGGGAUUCAGCG |
| 79 | UGGGUCACCAUAUUCUUGG | 242 | CCAAGAAUAUGGUGACCCA |
| 80 | UCCUCUGCCGAUCCAUACU | 243 | AGUAUGGAUCGGCAGAGGA |
| 81 | AUGUCAACGACCGACCUUG | 244 | CAAGGUCGGUCGUUGACAU |
| 82 | CCUCUGCCUAAUCAUCUCA | 245 | UGAGAUGAUUAGGCAGAGG |
| 83 | ACCGUGUGCACUUCGCUUC | 246 | GAAGCGAAGUGCACACGGU |
| 84 | UGCCGAUCCAUACUGCGGA | 247 | UCCGCAGUAUGGAUCGGCA |
| 85 | CAGAGUCUAGACUCGUGGU | 248 | ACCACGAGUCUAGACUCUG |
| 86 | CUGUUCAAGCCUCCAAGCU | 249 | AGCUUGGAGGCUUGAACAG |
| 87 | GGAGGCUGUAGGCAUAAAU | 250 | AUUUAUGCCUACAGCCUCC |
| 88 | AGGAGGCUGUAGGCAUAAA | 251 | UUUAUGCCUACAGCCUCCU |
| 89 | GGUGGACUUCUCUCAAUUU | 252 | AAAUUGAGAGAAGUCCACC |
| 90 | GCAACUUUUCACCUCUGC | 253 | GCAGAGGUGAAAAAGUUGC |
| 91 | CUGCUCGUGUUACAGGCGA | 254 | TCGCCUGUAACACGAGCAG |
| 92 | CUAGUGCCAUUUGUUCAGU | 255 | ACUGAACAAAUGGCACUAG |
| 93 | CUGCCGAUCCAUACUGCGG | 256 | CCGCAGUAUGGAUCGGCAG |
| 94 | GUGUGCACUUCGCUUCACC | 257 | GGUGAAGCGAAGUGCACAC |
| 95 | GCUCGUGUUACAGGCGGGC | 258 | GCCCGCCUGUAACACGAGC |
| 96 | CCUAUCUUAUCAACACUUC | 259 | GAAGUGUUGAUAAGAUAGG |
| 97 | UCUCAAUCGCCGCGUCGCA | 260 | UGCGACGCGGCGAUUGAGA |
| 98 | GCCCGUCUGUGCCUUCUCA | 261 | UGAGAAGGCACAGACGGGC |
| 99 | CUAUCUUAUCAACACUUCC | 262 | GGAAGUGUUGAUAAGAUAG |
| 100 | AUGUUGCCCGUUUGUCCUC | 263 | GAGGACAAACGGGCAACAU |
| 101 | GUAUGUUGCCCGUUUGUCC | 264 | GGACAAACGGGCAACAUAC |
| 102 | CUUCGCUUCACCUCUGCAC | 265 | GUGCAGAGGUGAAGCGAAG |
| 103 | UGUGCACUUCGCUUCACCU | 266 | AGGUGAAGCGAAGUGCACA |
| 104 | GCCAAAAUUCGCAGUCCCG | 267 | CGGGACUGCGAAUUUUGGC |
| 105 | CCUGCUCGUGUUACAGGCG | 268 | CGCCUGUAACACGAGCAGG |
| 106 | UGGAGUGUGGAUUCGCACU | 269 | AGUGCGAAUCCACACUCCA |
| 107 | AACGACCGACCUUGAGGCA | 270 | UGCCUCAAGGUCGGUCGUU |
| 108 | ACAGAGUCUAGACUCGUGG | 271 | CCACGAGUCUAGACUCUGU |
| 109 | AAUCGCCGCGUCGCAGAAG | 272 | CUUCUGCGACGCGGCGAUU |
| 110 | GGUAUGUUGCCCGUUUGUC | 273 | GACAAACGGGCAACAUACC |
| 111 | GCCGAUCCAUACUGCGGAA | 274 | UUCCGCAGUAUGGAUCGGC |
| 112 | GCCCUAUCUUAUCAACACU | 275 | AGUGUUGAUAAGAUAGGGC |
| 113 | AGUUUACUAGUGCCAUUUG | 276 | CAAAUGGCACUAGUAAACU |
| 114 | UGUCAACGACCGACCUUGA | 277 | UCAAGGUCGGUCGUUGACA |
| 115 | ACUUCUCUCAAUUUUCUAG | 278 | CUAGAAAAUUGAGAGAAGU |
| 116 | GCGCGGGACGUCCUUUGUC | 279 | GACAAAGGACGUCCCGCGC |
| 117 | UCUAGACUCGUGGUGGACU | 280 | AGUCCACCACGAGUCUAGA |
| 118 | GAUCCAUACUGCGGAACUC | 281 | GAGUUCCGCAGUAUGGAUC |

FIG. 1C

| 119 | CUCUGCCGAUCCAUACUGC | 282 | GCAGUAUGGAUCGGCAGAG |
|---|---|---|---|
| 120 | UCUGCCGAUCCAUACUGCG | 283 | CGCAGUAUGGAUCGGCAGA |
| 121 | CCUCUGCCGAUCCAUACUG | 284 | CAGUAUGGAUCGGCAGAGG |
| 122 | GCACCUCUCUUUACGCGGU | 285 | ACCGCGUAAAGAGAGGUGC |
| 123 | AAGAACUCCCUCGCCUCGC | 286 | GCGAGGCGAGGGAGUUCUU |
| 124 | GAACUCCCUCGCCUCGCAG | 287 | CUGCGAGGCGAGGGAGUUC |
| 125 | UCUCUCAAUUUUCUAGGGC | 288 | GCCCUAGAAAAUUGAGAGA |
| 126 | GGGCGCACCUCUCUUUACG | 289 | CGUAAAGAGAGGUGCGCCC |
| 127 | CCGAUCCAUACUGCGGAAC | 290 | GUUCCGCAGUAUGGAUCGG |
| 128 | AACUCCCUCGCCUCGCAGA | 291 | UCUGCGAGGCGAGGGAGUU |
| 129 | CUCCUCUGCCGAUCCAUAC | 292 | GUAUGGAUCGGCAGAGGAG |
| 130 | GGAGUGUGGAUUCGCACUC | 293 | GAGUGCGAAUCCACACUCC |
| 131 | CGGGCGCACCUCUCUUUAC | 294 | GUAAAGAGAGGUGCGCCCG |
| 132 | GUCUCAAUCGCCGCGUCGC | 295 | GCGACGCGGCGAUUGAGAC |
| 133 | AUCCAUACUGCGGAACUCC | 296 | GGAGUUCCGCAGUAUGGAU |
| 134 | CGCACCUCUCUUUACGCGG | 297 | CCGCGUAAAGAGAGGUGCG |
| 135 | CAACGACCGACCUUGAGGC | 298 | GCCUCAAGGUCGGUCGUUG |
| 136 | CCAUACUGCGGAACUCCUA | 299 | UAGGAGUUCCGCAGUAUGG |
| 137 | UGAAUCCCGCGGACGACCC | 300 | GGGUCGUCCGCGGGAUUCA |
| 138 | AGAACUCCCUCGCCUCGCA | 301 | UGCGAGGCGAGGGAGUUCU |
| 139 | GGCGCACCUCUCUUUACGC | 302 | GCGUAAAGAGAGGUGCGCC |
| 140 | GCGCACCUCUCUUUACGCG | 303 | CGCGUAAAGAGAGGUGCGC |
| 141 | GCUGAAUCCCGCGGACGAC | 304 | GUCGUCCGCGGGAUUCAGC |
| 142 | CACUUCGCUUCACCUCUGC | 305 | GCAGAGGUGAAGCGAAGUG |
| 143 | CUCAAUCGCCGCGUCGCAG | 306 | CUGCGACGCGGCGAUUGAG |
| 144 | UCCCGUCGGCGCUGAAUCC | 307 | GGAUUCAGCGCCGACGGGA |
| 145 | CUGAAUCCCGCGGACGACC | 308 | GGUCGUCCGCGGGAUUCAG |
| 146 | AGAGUCUAGACUCUGGGUG | 309 | CACCACGAGUCUAGACUCU |
| 147 | UCCAUACUGCGGAACUCCU | 310 | AGGAGUUCCGCAGUAUGGA |
| 148 | GCGCUGAAUCCCGCGGACG | 311 | CGUCCGCGGGAUUCAGCGC |
| 149 | AGUGUGGAUUCGCACUCCU | 312 | AGGAGUGCGAAUCCACACU |
| 150 | CCCUGCUCGUGUUACAGGC | 313 | GCCUGUAACACGAGCAGGG |
| 151 | GAAUCCCGCGGACGACCCG | 314 | CGGGUCGUCCGCGGGAUUC |
| 152 | AAGCUGUGCCUUGGGUGGC | 315 | GCCACCCAAGGCACAGCUU |
| 153 | GCCCUGCUCGUGUUACAGG | 316 | CCUGUAACACGAGCAGGGC |
| 154 | GUCCGUCGGCGCUGAAUC | 317 | GAUUCAGCGCCGACGGGAC |
| 155 | AUCUUAUCAACACUUCCGG | 318 | CCGGAAGUGUUGAUAAGAU |
| 156 | CUUAUCAACACUUCCGGAA | 319 | UUCCGGAAGUGUUGAUAAG |
| 156 | CUUAUCAACACUUCCGGAA | 320 | TUCCGGAAGUGUUGAUAAG |

FIG. 1D

Table 2. Activity testing in psiCHECK2 reporter system in COS7 cells.

| SEQ ID NO | sense strand sequence (5'-3') | SEQ ID NO | antisense strand sequence (5'-3') | Activity testing in psiCHECK2 reporter system in COS7 cells | | | |
|---|---|---|---|---|---|---|---|
| | | | | 10 nM siRNA | | 1 nM siRNA | |
| | | | | mean remaining mRNA (%) | standard deviation (%) | mean remaining mRNA (%) | standard deviation (%) |
| 321 | caAGGuAuGuuGcccGuuudTsdT | 485 | AAACGGGcAAcAuACCUUGdTsdT | 13 | 1 | 13 | 1 |
| 322 | CfuGfaAfgCfcAfuAfaAfuUfgGfuAf(invdT) | 486 | pdTAfcCfaAfuUfuAfuGfcCfuAfcAfgdTsdT | 8 | 2 | 14 | 2 |
| 323 | ucuGcGGcGuuuuAucAuAdTsdT | 487 | uAUGAuAAAACGCCgcAGAdTsdT | 15 | 7 | 29 | 11 |
| 324 | UfcUfgCfgGfcGfuUfuUfaUfcAfuAf(invdT) | 488 | pdTAfuGfaUfaAfaAfcGfcCfgCfaGfadTsdT | 6 | 2 | 15 | 4 |
| 325 | accucuGccuAAucAucucdTsdT | 489 | GAGAUGAUuAGGcAGAGGUdTsdT | 17 | 1 | 16 | 2 |
| 326 | UfuUfaCfuAfgUfgCfcAfuUfuGfuAf(invdT) | 490 | pdTAfcAfaAfuGfgCfaCfuAfgUfaAfadTsdT | 8 | 0 | 17 | 1 |
| 327 | AfcCfuCfuGfcCfuAfaUfcCfuAf(invdT) | 491 | pdTAfgAfuUfaGfaUfuAfgGfcAfgGfudTsdT | 6 | 2 | 19 | 3 |
| 328 | cuGuAGGcAuAAAuuGGucdTsdT | 492 | GACcAAUUuAUGCcuAcAGdTsdT | 23 | 2 | 28 | 6 |
| 329 | ugucuGcGGcGuuuuAucAdTsdT | 493 | UGAuAAAACGCCgcAGAcAdTsdT | 33 | 3 | 34 | 10 |
| 330 | UfgUfcUfgCfgGfcGfuUfuUfaUfcAf(invdT) | 494 | pdTGfaUfaAfaAfcGfcCfgCfaGfacCfadTsdT | 6 | 0 | 20 | 3 |
| 331 | uacuAGuGccAuuuGuucAdTsdT | 495 | UGAAcAAAuGGcACuAGuAdTsdT | 18 | 3 | 20 | 2 |
| 332 | UfaCfuAfgUfgCfcAfuUfuGfuUfcAf(invdT) | 496 | pdTGfaAfcAfaAfuGfgCfaCfuAfgUfadTsdT | 6 | 2 | 21 | 4 |
| 333 | CfaAfcUfuUfuUfcAfcCfuCfuGfcAf(invdT) | 497 | pdTGfcAfgAfgGfuGfaAfaAfaAfuUfgdTsdT | 6 | 2 | 21 | 3 |
| 334 | ccAuuuGuucAGuGuucGdTsdT | 498 | CGAAcAcUGAAcAAAUGGdTsdT | 12 | 1 | 21 | 1 |
| 335 | ccAAGuGuuuGcuGAcGcAdTsdT | 499 | UGCGUcAGcAAAcACUUGGdTsdT | 18 | 2 | 23 | 4 |
| 336 | CfcAfaGfuUfgCfuUfgAfcGfcAf(invdT) | 500 | pdTGfcGfucCfaGfcAfaAfcAfcUfuGfgdTsdT | 8 | 1 | 23 | 5 |
| 337 | CfcAfuUfgGfuUfcAfgUfgGfuUfcAf(invdT) | 501 | pdTGfaAfcCfaCfuGfaAfcAfaAfuGfgdTsdT | 7 | 2 | 24 | 3 |
| 338 | uuuAcuAGuGccAuuuGuudTsdT | 502 | AAcAAAUGGcACuAGuAAAdTsdT | 21 | 2 | 24 | 4 |
| 339 | CfaCfcUfcUfgCfcUfaAfuCfuAf(invdT) | 503 | pdTGfaUfgAfuUfaGfgCfaGfaGfgUfgdTsdT | 9 | 0 | 25 | 2 |
| 340 | cuGGccuAGuuuAcuAGuGdTsdT | 504 | cACuAGuAAACUGAGCcAGdTsdT | 34 | 3 | 29 | 7 |
| 341 | CfaAfgGfuAfuGfuGfCfcCfgUfuAf(invdT) | 505 | pdTGfaCfgfgCfaAfcAfuAfcCfuUfgdTsdT | 8 | 0 | 31 | 3 |
| 342 | CfuGfgCfcUfaGfuUfuAfcUfaGfuAf(invdT) | 506 | pdTAfcUfaGfuAfaAfcUfgGfcCfAfgdTsdT | 11 | 3 | 32 | 5 |
| 343 | gaGGcuAGGcAuAAuudTsdT | 507 | AAUUuAUGCcuAcAGCCUCdTsdT | 16 | 1 | 32 | 8 |
| 344 | caGuuuActuAGuGccAuuudTsdT | 508 | AAAuGGcAcuAGuAAACUGdTsdT | 37 | 1 | 33 | 8 |

FIG. 2A

| | | | | | | |
|---|---|---|---|---|---|---|
| 345 | agGuAuGuuGcccGuuuGudTsdT | 509 | AcAAACGGGcAAcAuACCUdTsdT | 33 | 3 | 34 | 4 |
| 346 | UfaUfgUfuGfcCfcGfuUfuGfuGfcCfcAf(invdT) | 510 | pdTGfgAfcAfaAfcGfgGfcAfaCfaUfadTsdT | 9 | 3 | 35 | 5 |
| 347 | GfaGfgCfuGfuAfgGfcAfuAfaAfuAf(invdT) | 511 | pdTAfuUfuAfuGfcCfuAfcAfgCfcUfcdTsdT | 9 | 1 | 36 | 4 |
| 348 | gucuGcGGcGuuuuAucAcudTsdT | 512 | AUGAuAAACGCCgAAACAGACdTsdT | 26 | 3 | 36 | 14 |
| 349 | caAcuuuuucAccucuGccdTsdT | 513 | GGcAGAGGUGAAAAAGUUGGdTsdT | 24 | 2 | 37 | 9 |
| 350 | ccGuGuGcAcucuGcuucAdTsdT | 514 | UGAAGCGAAGUGcAcACGGdTsdT | 13 | 1 | 16 | 5 |
| 351 | CfcGfuGfuGfcAfcUfcCfgCfuUfcAf(invdT) | 515 | pdTGfaAfgCfgAfaGfuGfcAfcAfcGfgdTsdT | 13 | 2 | 38 | 4 |
| 352 | UfcAfaGfgUfaUfgUfuGfcCfcGfuAf(invdT) | 516 | pdTAfcGfgGfcAfaCfaCfcUfuGfadTsdT | 12 | 1 | 38 | 4 |
| 353 | CfaGfuUfuAfcUfaGfuGfcCfaUfuAf(invdT) | 517 | pdTAfaUfgGfcAfcUfaGfuAfaAfcUfgdTsdT | 12 | 2 | 38 | 5 |
| 354 | ugGuGGAcucucucuAAuudTsdT | 518 | AAUUGAGAGAAGUCcACcAdTsdT | 24 | 6 | 39 | 16 |
| 355 | AfgGfuAfuGfuUfcCfcCfgUfuUfgAf(invdT) | 519 | pdTCfaAfaCfgGfgCfaAfcAfuCfudTsdT | 18 | 1 | 40 | 4 |
| 356 | cuGcucGuGuuAcAGGcGGdTsdT | 520 | CCGCCUGuAAcACAGAGcAGdTsdT | 26 | 2 | 40 | 11 |
| 357 | uauGuuGcccGuuuGuccudTsdT | 521 | AGGAcAAACGGGcAAcAAdTsdT | 42 | 1 | 40 | 3 |
| 358 | ucAAGGAuGuuGcccGuudTsdT | 522 | AACGGGcAAcAuACCUUGAdTsdT | 31 | 4 | 42 | 12 |
| 359 | ucuuAucAACAcuccGGAdTsdT | 523 | UCCGGAAGUGUUGAuAAGAdTsdT | 35 | 2 | 43 | 38 |
| 360 | UfcUfuAfuCfaAfcAfcUfuCfcGfgAf(invdT) | 524 | pdTCfcGfaAfgUfuUfgAfuAfaGfadTsdT | 32 | 2 | 46 | 3 |
| 361 | caccucuGccuAAucAucudTsdT | 525 | AGAUGAUuAGGcAGAGGUGdTsdT | 31 | 3 | 47 | 8 |
| 362 | auAAGAGGAcucuuGGAcudTsdT | 526 | AGUccAAGAGUCCUCUuAUdTsdT | 28 | 1 | 49 | 6 |
| 363 | GfuCfuCfgCfgfgUfuUfuAfuCfaAf(invdT) | 527 | pdTUfgAfuAfaAfaCfgCfcGfcAfgAfcdTsdT | 15 | 0 | 51 | 4 |
| 364 | gggGcuGAAucccGcGGAcudTsdT | 528 | GUCCGCGGGAUUcAGCGCCdTsdT | 24 | 3 | 51 | 10 |
| 365 | cgcGucGcAGAAGAucucAdTsdT | 529 | UGAGAUCUUCUGGCACGGdTsdT | 46 | 3 | 53 | 6 |
| 366 | aauGucAAcGAccGAccudTsdT | 530 | AAGGUCGGUCGUUGAcAUdTsdT | 40 | 1 | 54 | 8 |
| 367 | gcucAGuuuAcuAGuGccAdTsdT | 531 | UGGcACuAGuAAACUGAGCdTsdT | 37 | 5 | 51 | 4 |
| 368 | UfgGfuGfgAfcCfuCfuCfcAfuAf(invdT) | 532 | pdTAfuUfgAfgAfgAfgfuCfcAfcCfadTsdT | 20 | 4 | 58 | 6 |
| 369 | aucGccGcGucGcAGAAGAdTsdT | 533 | UCUUCUGCACGCGGCGAUdTsdT | 57 | 6 | 58 | 1 |
| 370 | gccAuuuGuucAGuGGAucudTsdT | 534 | GAACCACUGAACAAAUGGCdTsdT | 36 | 3 | 60 | 6 |
| 371 | cgAuccAuAcuGGGAAucudTsdT | 535 | AGUUCCGcAGuAUGGAUCdTsdT | 43 | 8 | 61 | 9 |
| 372 | ucAcccuGccuAAucAucdTsdT | 536 | GAUGAUuAGGcAGAGGUGAdTsdT | 48 | 4 | 61 | 10 |
| 373 | guGGAcuuucucuAAuuucdTsdT | 537 | AAAAUUGAGAGAAAGUCcACdTsdT | 31 | 4 | 61 | 5 |
| 374 | ggGucAccAuAuucuuGGGdTsdT | 538 | CCcAAGAAAUAUGGUGACCdTsdT | 58 | 6 | 62 | 10 |
| 375 | gccGcGucGcAGAAGAucudTsdT | 539 | AGAUCUUCUGCGACGCGGCdTsdT | 59 | 3 | 64 | 7 |

FIG. 2B

| | | | | | | | |
|---|---|---|---|---|---|---|---|
| 376 | ucAAucGcccGcGucGcAGAdTsdT | 540 | UCUGCGACGCGGCGAUUGAdTsdT | 59 | 1 | 64 | 9 |
| 377 | ugGAuGuGucGcGGcGuudTsdT | 541 | AACGCCgCAGAcAcAGuACCAdTsdT | 44 | 8 | 65 | 12 |
| 378 | uacuGuucAAGccuccAAGdTsdT | 542 | CUUGGAGGCUUGAAcAGuAAACAdTsdT | 51 | 2 | 65 | 32 |
| 379 | guuuAcuAGuGccAuuuGudTsdT | 543 | AcAAAUGGcACuAGuAAACdTsdT | 44 | 5 | 66 | 6 |
| 380 | acuAGuGccAuuuGuucAGdTsdT | 544 | CUGAAcAAAUGGcACuAGUdTsdT | 56 | 0 | 66 | 5 |
| 381 | ccGcGucGcAGAAGAAucucdTsdT | 545 | GAGAUCUUCUCGCGACGCGGdTsdT | 59 | 3 | 67 | 11 |
| 382 | uaucuuAucAAcAcuuccGdTsdT | 546 | CGGAAGUGUUGAuAAGAuAdTsdT | 37 | 1 | 67 | 51 |
| 383 | ggccAAAAuucGcAGcccdTsdT | 547 | GGGACUGCGAAUUUUGGCCdTsdT | 49 | 6 | 67 | 7 |
| 384 | uucAccucGccuAAucAudTsdT | 548 | AuGAUuAGGcAGAGGUGAAdTsdT | 50 | 4 | 68 | 7 |
| 385 | cucAGuuuAcuAGuGccAudTsdT | 549 | AuGGcACuAGuAAACUGAGdTsdT | 52 | 2 | 68 | 6 |
| 386 | uguuGcccGuuuGucccucdTsdT | 550 | AGAGGAcAAACGGGcAAcAdTsdT | 50 | 2 | 69 | 4 |
| 387 | uaGuGccAuuuGuucAGuGudTsdT | 551 | cACUGAAcAAAUGGcACuAdTsdT | 46 | 1 | 70 | 8 |
| 388 | agGcGuAGGcAuAAAuuGdTsdT | 552 | cAAUUuAUGCCuACAGCCUdTsdT | 69 | 3 | 71 | 13 |
| 389 | auGuGucuGcGGcGuuuuAdTsdT | 553 | uAAAACGCCgcAGAcAcAUdTsdT | 17 | 6 | 33 | 12 |
| 390 | AfuGfuGfuCfuGfcGfgCfgUfuUfuAf(invdT) | 554 | pdTAfaAfaCfgCfcGfcAfgAfcAfcAfudTsdT | 24 | 3 | 72 | 4 |
| 391 | acuucGcuucAcccucGcAdTsdT | 555 | UGcAGAGGUGAAGCGAAGUdTsdT | 49 | 4 | 73 | 4 |
| 392 | cguGuGcAcuucGcuucAcdTsdT | 556 | GUGAAGCGAAGUGcACACGdTsdT | 45 | 3 | 73 | 10 |
| 393 | guGGuGGAcuucucuAAudTsdT | 557 | AUUGAGAGAAGUCCACcACdTsdT | 47 | 5 | 73 | 5 |
| 394 | uguGucuGcGGcGuuuuAudTsdT | 558 | AuAAAACGCCgcAGAcAcAUdTsdT | 62 | 8 | 75 | 14 |
| 395 | aaGGuAuGuuGcccGuuuGdTsdT | 559 | cAAACGGGcAAcAuACCUUdTsdT | 61 | 3 | 76 | 2 |
| 396 | ucAAcGAccGAccuuGAGGdTsdT | 560 | CCUcAAGGUCGGUCGUUGAdTsdT | 57 | 1 | 76 | 16 |
| 397 | cauAAGAGGAcucuuGGAcdTsdT | 561 | GUCcAAGAGUCCUCUuAUGdTsdT | 62 | 4 | 76 | 4 |
| 398 | gucAAcGAccGAccuuGAGdTsdT | 562 | CUcAAGGUCGGUCGUUGACdTsdT | 55 | 2 | 77 | 13 |
| 399 | auAuucuuGGGAAcAAGAGdTsdT | 563 | CUCUGUUCCuAAGAAuAAUdTsdT | 56 | 5 | 77 | 11 |
| 400 | ugcucGuGuuAcAGGcGGGdTsdT | 564 | CCCGCCUGuAAcACGAGcAdTsdT | 61 | 5 | 78 | 4 |
| 401 | cAAucGcGucGcAGAAdTsdT | 565 | UUCUGCGACGCGGCGAUUGdTsdT | 65 | 1 | 78 | 4 |
| 402 | acuGuucAAGccuccAAGcdTsdT | 566 | GCUUGGAGGCUUGAAcAGUdTsdT | 86 | 3 | 78 | 5 |
| 403 | cgccGcGucAGuGAGAAGcdTsdT | 567 | GAUCUUCUGcGACGCGGCdTsdT | 71 | 3 | 79 | 2 |
| 404 | cauuuGuucAGuGuucGudTsdT | 568 | ACGAACcACUGAAcAAAUGdTsdT | 54 | 5 | 80 | 4 |
| 405 | cgcAAucccGcGGAcGcAGdTsdT | 569 | UCGUCCGCGGGAUUcAGCGdTsdT | 62 | 2 | 80 | 7 |

FIG. 2C

| | | | | | |
|---|---|---|---|---|---|
| 406 | ugGucAccAuAuucuGGdTsdT | 570 | CcAAGAAuAUGGUGAccAdTsdT | 75 | 2 | 80 | 16 |
| 407 | uccucuGccGAuccAuAcudTsdT | 571 | AGuAUGGAUCGGcAGAGGAdTsdT | 73 | 2 | 81 | 3 |
| 408 | auGucAAcGAccGAccuuGdTsdT | 572 | cAAGGUCGGUCGUuGAcAUdTsdT | 69 | 8 | 81 | 7 |
| 409 | ccucuGccuAAucAucucAdTsdT | 573 | UGAGAuGAUuAGGcAGAGGdTsdT | 81 | 4 | 81 | 4 |
| 410 | accGuGuGcAcucuGcuucdTsdT | 574 | GAAGCGAAGUGcACGGUdTsdT | 46 | 5 | 81 | 7 |
| 411 | ugccGAuccAuAcuGcGGAdTsdT | 575 | UCCGcAGuAUGGAUCGGGAdTsdT | 61 | 8 | 81 | 5 |
| 412 | caGAGucuAGAcucGuGGudTsdT | 576 | ACcACGAGUCuAGACUCUGdTsdT | 65 | 9 | 81 | 5 |
| 413 | cuGuucAAGccuccAAGcudTsdT | 577 | AGCUUGGAGGCUUGAAcAGdTsdT | 82 | 3 | 82 | 21 |
| 414 | ggAGGcuGuAGGcAuAAAudTsdT | 578 | AUUuAUGCCuAcAGCCuCCdTsdT | 68 | 2 | 82 | 12 |
| 415 | agAGGcuGuAGGcAuAAAdTsdT | 579 | UUuAUGCCuAcAGCCuCCUdTsdT | 55 | 4 | 83 | 5 |
| 416 | gguGGAcuucucucAAuuudTsdT | 580 | AAAUUGAGAGAAGCcACCdTsdT | 62 | 7 | 84 | 2 |
| 417 | gcAAcuuuuucAccucuGcdTsdT | 581 | GcAGAGGUGAAAAAGUUGCudTsdT | 93 | 1 | 85 | 5 |
| 418 | CfuGfcUfcGfuUfaCfaGfcGfgAf(invdT) | 582 | pdTcfgCfcUfgUfaAfcAfcGfaGfcAfgdTsdT | 56 | 1 | 86 | 2 |
| 419 | cuAGuGccAuuuGuucAGudTsdT | 583 | ACUGAAcAAAUGGcACuAGdTsdT | 66 | 0 | 86 | 6 |
| 420 | cuGccGAuccAuAcuGcGGdTsdT | 584 | CCGcAGuAUGGAUCGGcAGdTsdT | 73 | 8 | 86 | 5 |
| 421 | guGuGcAcuucGcuucAccdTsdT | 585 | GGUGAAGCGAAGUGcAcAGdTsdT | 54 | 4 | 87 | 4 |
| 422 | gcucGuGuuAcAGGcGGGcdTsdT | 586 | GCCCGCCUGuAAcACGAGCdTsdT | 91 | 4 | 87 | 5 |
| 423 | ccuAucuAucAcAcuucdTsdT | 587 | GAAGUGUUGAuAAGAuAGGdTsdT | 37 | 2 | 88 | 45 |
| 424 | ucucAAucGccGcGucGcAdTsdT | 588 | UGCGACGCGGCGAUUGAGAdTsdT | 79 | 4 | 88 | 6 |
| 425 | gcccGucuGuGccuucuAcdTsdT | 589 | UGAGAAGGcACAGACGGGCdTsdT | 85 | 4 | 88 | 16 |
| 426 | cuAucuuAucAAcAcuucdTsdT | 590 | GGAAGUGUUGAuAAGAuAGdTsdT | 43 | 3 | 90 | 23 |
| 427 | auGuuGcccGuuuuGuccudTsdT | 591 | GAGGAcAAACGGGcAAcAUdTsdT | 87 | 5 | 90 | 4 |
| 428 | guAuGuGcccGuuuuGuccdTsdT | 592 | GGAcAAACGGGcAAcAuACdTsdT | 88 | 4 | 90 | 11 |
| 429 | cuucGcuucAccucuGcAcdTsdT | 593 | GUGcAGAGGUGAAGCGAAGdTsdT | 69 | 7 | 91 | 5 |
| 430 | uguGcAcuucGcuucAccudTsdT | 594 | AGGUGAAGCGAAGUGcAcAdTsdT | 76 | 3 | 91 | 14 |
| 431 | gccAAAAuucGcAGucccGdTsdT | 595 | CGGGACUGCGAAUUUuGGCdTsdT | 81 | 3 | 92 | 3 |
| 432 | ccuGcucGuuAcAGGcGGdTsdT | 596 | CGCCUGuAAcACGAGcAGGdTsdT | 86 | 3 | 92 | 1 |
| 433 | ugGAGuGuGAuucGcAcudTsdT | 597 | AGUGCGAAUCcAcACUCcAdTsdT | 87 | 4 | 92 | 3 |
| 434 | aacGAccGAccuuGAuucGcAdTsdT | 598 | UGCCUcAAGGUCGUCGUUUdTsdT | 83 | 9 | 92 | 3 |
| 435 | acAGAGucuAGAcucGuGGdTsdT | 599 | CcACGAGUCuAGACUCUGdTsdT | 89 | 4 | 92 | 4 |

FIG. 2D

| | | | | | | |
|---|---|---|---|---|---|---|
| 436 | aaucGccGcGucGcAGAAGdTsdT | | 600 | CUUCUGCGACGCGGGCGAUUdTsdT | 85 | 6 | 92 | 2 |
| 437 | gguAuGuuGcccGuuuGucdTsdT | | 601 | GacAAAcGGGcAAcAuAccdTsdT | 80 | 2 | 93 | 3 |
| 438 | gccGAuccAuAcuGcGGAAdTsdT | | 602 | UUCCGcAGuAUGGAUCGGcdTsdT | 79 | 3 | 93 | 3 |
| 439 | gcccuAucuuAucAcAcudTsdT | | 603 | AGUGUUGAuAAGAuAGGGCdTsdT | 84 | 4 | 94 | 50 |
| 440 | aguuuAcuAGuGccAuuuGdTsdT | | 604 | cAAAUGGcAcuAGuAAACUdTsdT | 89 | 7 | 95 | 8 |
| 441 | ugucAAcGAccGAccuuGAdTsdT | | 605 | UcAAGGUCGGUCGUUgAcAdTsdT | 84 | 5 | 95 | 8 |
| 442 | acuucucuAAuuuucuAGdTsdT | | 606 | CuAGAAAAUUGAGAGAAGUdTsdT | 103 | 3 | 95 | 6 |
| 443 | gCGcGGGAcGucccuuuGucdTsdT | | 607 | GacAAAGGACGUCCCGCGCdTsdT | 88 | 4 | 97 | 3 |
| 444 | ucuAGAcucGuGuGGAcudTsdT | | 608 | AGUCCACCACGAGUCuAGAdTsdT | 90 | 5 | 97 | 2 |
| 445 | gauccAuAcuGcGGAAcucdTsdT | | 609 | GAGUUCCGcAGuAUGGAUCdTsdT | 73 | 6 | 98 | 4 |
| 446 | cucucGccGAuccAuAcuGcdTsdT | | 610 | GcAGuAUGGAUCGGcAGAGdTsdT | 100 | 5 | 99 | 7 |
| 447 | ucuGccGAuccAuAcuGcGcdTsdT | | 611 | CGcAGuAUGGAUCGGcAGAdTsdT | 88 | 6 | 99 | 4 |
| 448 | ccucuGccGAuccAuAcuGdTsdT | | 612 | cAGuAUGGAUCGGcAGAGGdTsdT | 98 | 11 | 99 | 5 |
| 449 | gcAccucuuuAcGcGGudTsdT | | 613 | ACCGGuAAAGAGAGGUGCAdTsdT | 82 | 7 | 100 | 4 |
| 450 | aaGAAcuccucGccucGcdTsdT | | 614 | GCGAGGCGAGGGAGGUUCUUdTsdT | 97 | 6 | 100 | 1 |
| 451 | gaAcucccucGccucGcAGdTsdT | | 615 | CUGCGAGGCGAGGGAGUUCdTsdT | 100 | 2 | 100 | 2 |
| 452 | ucucuAAuuucuAGGGCdTsdT | | 616 | GCCCuAGAAAAUUGAGAGAdTsdT | 102 | 4 | 100 | 8 |
| 453 | ggGcAccucuuuAcGdTsdT | | 617 | CGuAAAGAGAGGUGCGCCCdTsdT | 80 | 4 | 100 | 3 |
| 454 | ccGAuccAuAcuGcGGAAcdTsdT | | 618 | GUUCCGcAGuAUGGAUCGGdTsdT | 83 | 5 | 101 | 3 |
| 455 | aaccccucGccucGcAGAdTsdT | | 619 | UCUGCGAGGCGAGGGAGUUdTsdT | 100 | 2 | 101 | 2 |
| 456 | cucucuGccGAuccAuAcdTsdT | | 620 | GuAUGGAUCGGcAGAGGAGdTsdT | 93 | 2 | 101 | 2 |
| 457 | ggAGuGuGAuuucGcAcucdTsdT | | 621 | GAGUGCGAAUCcAcAcUCCdTsdT | 97 | 5 | 101 | 3 |
| 458 | cgGGcGcAccucuuuAcdTsdT | | 622 | GuAAAGAGAGGUGCGCCCdTsdT | 83 | 6 | 101 | 6 |
| 459 | gucucAAuGcGcGcGucGcdTsdT | | 623 | GCGACGCGGCGAUUGAGACdTsdT | 92 | 4 | 102 | 9 |
| 460 | auccAuAcuGcGGAAcucdTsdT | | 624 | GGAGUUCCGcAGuAUGGAUdTsdT | 88 | 3 | 102 | 7 |
| 461 | cgcAccucuuuAcGcGGdTsdT | | 625 | CCGCGuAAAGAGAGGUGCdTsdT | 78 | 1 | 102 | 10 |
| 462 | caAcGAccGAccuuGAGGcdTsdT | | 626 | GCCUcAAGGUCGGUCGUUGdTsdT | 88 | 4 | 102 | 8 |
| 463 | ccAuAcuGcGGAAcuccuAdTsdT | | 627 | uAGGAGUUCCGcAGuAUGGdTsdT | 85 | 3 | 102 | 5 |
| 464 | ugAuccGGGAcGAcGAcccdTsdT | | 628 | GGGUCGUCCCGGGAUUcAdTsdT | 92 | 4 | 103 | 3 |
| 465 | agAAcuccucGccucGcAdTsdT | | 629 | UGCGAGGCGAGGGAGUUCUdTsdT | 94 | 5 | 103 | 2 |

FIG. 2E

| | | | | | | |
|---|---|---|---|---|---|---|
| 466 | ggcGcAccucucuuuAcGcGcdTsdT | 630 | GCGuAAAGAGAGGUGCGCCdTsdT | 97 | 7 | 103 | 10 |
| 467 | gcGcAccucucuuuAcGcGcGcdTsdT | 631 | CGCGuAAAGAGAGGUGCGCGCdTsdT | 99 | 5 | 104 | 7 |
| 468 | gcuGAAucccGcGGAcGAcdTsdT | 632 | GUCGUCCGCGGGAUUcAGCdTsdT | 84 | 2 | 104 | 3 |
| 469 | cacuucGcuucAcucucuGcdTsdT | 633 | GcAGAGGUGAAGCGAAGUGdTsdT | 90 | 4 | 105 | 12 |
| 470 | cucAAucGccGccGucGcAGdTsdT | 634 | CUGGGACGCGGGAUUGAGdTsdT | 99 | 3 | 105 | 14 |
| 471 | ucccGucGGcGcuGAAucccdTsdT | 635 | GGAUUcAGCGCCGACGGGAdTsdT | 91 | 3 | 106 | 7 |
| 472 | cuGAAucccGcGGAcGAccdTsdT | 636 | GGUCGUCCGCGGGAUUcAGdTsdT | 96 | 2 | 106 | 6 |
| 473 | agAGucuAGAcucGuGGuGdTsdT | 637 | cACcACGAGUcAGACUCUdTsdT | 93 | 4 | 107 | 9 |
| 474 | uccAuAcuGcGGAAcuccudTsdT | 638 | AGGAGUUCCGcAGuAUGGAdTsdT | 91 | 4 | 107 | 7 |
| 475 | gcGcuGAAucccGcGGAcGdTsdT | 639 | CGUCCGCGGGAUUcAGCGCdTsdT | 90 | 3 | 108 | 3 |
| 476 | aguGuGGAuucGcAcuccudTsdT | 640 | AGGAGUGCGAAUcAcACUdTsdT | 94 | 4 | 111 | 3 |
| 477 | cccuGcucGuGuuAcAGGGcdTsdT | 641 | GCCUGuAAcACGAGcAGGGdTsdT | 99 | 11 | 111 | 10 |
| 478 | gaAucccGcGGAcGAccGdTsdT | 642 | CGGGUCGUCCGCGGGAUUCdTsdT | 96 | 3 | 115 | 5 |
| 479 | aaGcuGuGccuuGGGuGGcdTsdT | 643 | GCcACCcAAGGcAcAGCUUdTsdT | 99 | 5 | 116 | 53 |
| 480 | gcccuGcucGuGuuAcAGGdTsdT | 644 | CCUGuAAcACGAGcAGGGCdTsdT | 96 | 5 | 116 | 11 |
| 481 | gucccGucGGcGcuGAAucdTsdT | 645 | GAUUcAGCGCCGACGGGACdTsdT | 93 | 2 | 118 | 4 |
| 482 | acuuuAucAAcAcuccGGAdTsdT | 646 | CCGGAAGUGUUGAuAAGAUdTsdT | 76 | 3 | 126 | 23 |
| 483 | cuuAucAAcAcuuccGGAAdTsdT | 647 | UUCCGGAAGUGUUGAuAAGdTsdT | 39 | 6 | 42 | 3 |

FIG. 2F

Table 3. Serum stability of dsRNAs targeting Hepatitis B Virus.

| SEQ ID No. Pair | Mouse Serum | | Human Serum | | Cynomologous Serum | |
|---|---|---|---|---|---|---|
| | sense $t_{1/2}$ (hr) | antisense $t_{1/2}$ (hr) | sense $t_{1/2}$ (hr) | antisense $t_{1/2}$ (hr) | sense $t_{1/2}$ (hr) | antisense $t_{1/2}$ (hr) |
| 321/485 | 26.4 | 0.5 | >48 | 2.1 | n.d. | n.d. |
| 325/489 | 27.2 | 6.7 | >48 | 8.8 | n.d. | n.d. |
| 350/514 | 11.3 | 2.6 | >48 | 17.0 | n.d. | n.d. |
| 326/490 | >48 | 11.7 | >48 | 43.9 | >48 | 5.5 |
| 324/488 | >48 | 13.3 | >48 | 44.7 | >48 | 6.4 |
| 328/492 | 19.1 | 9.9 | >48 | >48 | n.d. | n.d. |
| 322/486 | >48 | 14.5 | >48 | >48 | >48 | 6.5 |
| 327/491 | >48 | 16.0 | >48 | >48 | >48 | 8.1 |

FIG. 3

Table 4. Core sequences of dsRNAs targeting Hepatitis B Virus gene and their modified counterparts.

| | core sequence | | | modified sequence | | |
|---|---|---|---|---|---|---|
| SEQ ID No. | sense strand sequence (5'-3') | SEQ ID No. | antisense strand sequence (5'-3') | SEQ ID No. | sense strand sequence (5'-3') | SEQ ID No. | antisense strand sequence (5'-3') |
| 1 | CAAGGUAUGUUGCCCGUUU | 157 | AAACGGGCAACAUACCUUG | 321 | caAGGuAuGuuGcccGuuudTsdT | 485 | AAACGGGcAAcAuACCUUGdTsdT |
| 2 | CUGUAGGCAUAAAUUGGUA | 158 | TACCAAUUUAUGCCUACAG | 322 | CfuGfuAfgGfcAfuAfaAfuUfgGfuAf(invdT) | 486 | pdTAfcCfaAfuUfuAfuGfcCfuAfcAfgdTsdT |
| 3 | UCUGCGGGCGUUUUAUCAUA | 159 | UAUGAUAAAACGCCGCAGA | 323 | ucuGcGGGcGuuuuAucAuAdTsdT | 487 | uAUGAuAAAACGCCGcAGAdTsdT |
| 3 | UCUGCGGGCGUUUUAUCAUA | 160 | TAUGAUAAAACGCCGCAGA | 324 | UfcUfgCfgGfcGfuUfuUfaUfcAfuAf(invdT) | 488 | pdTAfuGfaUfaAfaAfcGfcCfgCfaGfadTsdT |
| 4 | ACCUCUGCCUAAUCAUCUC | 161 | GAGAUGAUUAGGCAGAGGU | 325 | accucuGccuAAucAucucdTsdT | 489 | GAGAUGAUuAGGcAGAGGUdTsdT |
| 5 | UUUACUAGUGCCAUUUGUA | 162 | TACAAAUGGCACUAGUAAA | 326 | UfuUfaCfuAfgUfgCcAfuUfuGfuAf(invdT) | 490 | pdTAfcAfaAfuGfgCfaCfuAfgUfaAfadTsdT |
| 6 | ACCUCUGCCUAAUCAUCUA | 163 | TAGAUGAUUAGGCAGAGGU | 327 | AfcCfuCfuGfcCfuAfaUfcAfuCfuAf(invdT) | 491 | pdTAfgAfuGfaUfuAfgGfcAfgAfgGfudTsdT |
| 7 | CUGUAGGCAUAAAUUGGUC | 164 | GACCAAUUUAUGCCUACAG | 328 | cuGuAGGcAuAAAuuGGucdTsdT | 492 | GACcAAUuuAUGCCuAcAGdTsdT |
| 8 | UGUCUGCGGGCGUUUUAUCA | 165 | UGAUAAAACGCCGCAGACA | 329 | ugucuGcGGGcGuuuuAucAdTsdT | 493 | UGAuAAAACGCCGcAGAcAdTsdT |
| 8 | UGUCUGCGGGCGUUUUAUCA | 166 | TGAUAAAACGCCGCAGACA | 330 | UfgUfcUfgCfgGfcGfuUfuUfaUfcAf(invdT) | 494 | pdTGfaUfaAfaAfcGfcCfgCfaGfaCfadTsdT |
| 9 | UACUAGUGCCAUUUGUUCA | 167 | UGAACAAAUGGCACUAGUA | 331 | uacuAGuGccAuuuGuucAdTsdT | 495 | UGAAcAAAUGGcACuAGuAdTsdT |
| 9 | UACUAGUGCCAUUUGUUCA | 168 | TGAACAAAUGGCACUAGUA | 332 | UfaCfuAfgUfgCcAfuUfuGfuUfcAf(invdT) | 496 | pdTGfaAfcAfaAfuGfgCfaCfuAfgUfadTsdT |
| 10 | CAACUUUUUCACCUCUGCA | 169 | TGCAGAGGUGAAAAAGUUG | 333 | CfaAfcUfuUfuUfcAfcCfuCfuGfcAf(invdT) | 497 | pdTGfcAfgAfgGfuGfaAfaAfaGfuUfgdTsdT |

FIG. 4A

| | | | | | |
|---|---|---|---|---|---|
| 11 | CCAUUGUUCAGUGGUUCG | 170 | CGAACCACUGAACAAAUGG | 334 | ccAuuuGuucAGuGGuucG dTsdT | 498 | CGAACcACUGAAcAAAUGGd TsdT |
| 12 | CCAAGUGUUUGCUGACGCA | 171 | UGCGUCAGCAAACACUUGG | 335 | ccAAGuGuuuGcuGAcGc AdTsdT | 499 | UGCGUcAGCAAAcACUUGGd TsdT |
| 12 | CCAAGUGUUUGCUGACGCA | 172 | TGCGUCAGCAAACACUUGG | 336 | CfcAfaGfuGfuUfuGfcUfg AfcGfcAf(invdT) | 500 | pdTGfcGfcuCfaGfcAfaAfcAfc UfuGfgdTsdT |
| 13 | CCAUUGUUCAGUGGUUCA | 173 | TGAACCACUGAACAAAUGG | 337 | CfcAfuUfuGfuUfcAfgUfg GfuUfcAf(invdT) | 501 | pdTGfaAfcCfaCfuGfaAfcAfa AfuGfgdTsdT |
| 14 | UUUACUAGUGCCAUUUGUU | 174 | AACAAAUGGCACUAGUAAA | 338 | uuuAcuAcuAgUgCcAuuuGuu dTsdT | 502 | AAcAAAUGGcACuAGuAAAd TsdT |
| 15 | CACCUCUGCCUAAUCAUCA | 175 | TGAUGAUUAGGCAGAGGUG | 339 | CfaCfcUfcUfgCfcUfaAfuC faUfcAf(invdT) | 503 | pdTGfaUfgAfuUfaGfgCfaGfa GfgUfgdTsdT |
| 16 | CUGGCUCAGUUUACUAGUG | 176 | CACUAGUAAACUGAGCCAG | 340 | cuGGcucAGuuuAcuAGu GdTsdT | 504 | cACuAGuAAACUGAGCcAGd TsdT |
| 17 | CAAGGUAUGUUGCCCGUUA | 177 | TAACGGGCAACAUACCUUG | 341 | CfaAfgGfuAfuGfuUfgCfc CfgUfuAf(invdT) | 505 | pdTAfaCfgGfgCfaAfcAfuAfcC fuUfgdTsdT |
| 18 | CUGGCUCAGUUUACUAGUA | 178 | TACUAGUAAACUGAGCCAG | 342 | CfuGfgCfuCfaGfuUfuAfc UfaGfuAf(invdT) | 506 | pdTAfcGfuAfaAfcUfgAfgCfc AfugdTsdT |
| 19 | GAGGCUGUAGGCAUAAAUU | 179 | AAUUUAUGCCUACAGCCUC | 343 | gaGGcuGuAGGcAuAAAu udTsdT | 507 | AAUuuAuGCCuACAGCCUCd TsdT |
| 20 | CAGUUUACUAGUGCCAUUU | 180 | AAAUGGCACUAGUAAACUG | 344 | caGuuuAcuAGuGccAuuu dTsdT | 508 | AAAUGGcACuAGuAAACUGd TsdT |
| 21 | AGGUAUGUUGCCCGUUUGU | 181 | ACAAACGGGCAACAUACCU | 345 | agGuAuGuuGcccGuuuGu dTsdT | 509 | AcAAACGGGcAAcAuACCUd TsdT |
| 22 | UAUGUUGCCCGUUUGUU | 182 | UGGACAAACGGGCAACAUA | 346 | UfaUfgUfuGfcCfcGfuUfu GfuCfcAf(invdT) | 510 | pdTGfgAfcAfaAfcGfgGfcAfa CfaUfadTsdT |
| 23 | GAGGCUGUAGGCAUAAAUA | 183 | TAUUUAUGCCUACAGCCUC | 347 | GfaGfgCfuGfuAfgGfcAfu AfaAfuAf(invdT) | 511 | pdTAfuUfuAfuGfcCfuAfcAfg CfcUfcdTsdT |
| 24 | GUCUGCGGGCGUUUUAUCAU | 184 | AUGAUAAAACGCCCGCAGAC | 348 | gucuGcGGGcGuuuuAucAu dTsdT | 512 | AUGAuAAAACGCCCGcAGACd TsdT |
| 25 | CAACUUUUUCACCUCUGCC | 185 | GGCAGAGGUGAAAAAGUUG | 349 | cAAcuuuuucAccucuGccd TsdT | 513 | GGcAGAGGUGAAAAAGUUG dTsdT |

FIG. 4B

| | | | | | |
|---|---|---|---|---|---|
| 26 | CCGUGUGCACUUCGCUUCA | 186 | UGAAGCGAAGUGCACACGG | 350 | ccGuGuGcAcuucGcuucAdTsdT | 514 | UGAAGCGAAGUGCAcACGGdTsdT |
| 26 | CCGUGUGCACUUCGCUUCA | 187 | TGAAGCGAAGUGCACACGG | 351 | CfcGfuGfuGfcAfcUfuCfgCfuUfcAf(invdT) | 515 | pdTGfaAfgCfgAfaGfuGfcAfcAfcGfgdTsdT |
| 27 | UCAAGGUAUGUUGCCCGUA | 188 | TACGGGCAACAUACCUUGA | 352 | UfcAfaGfgUfaUfgUfuGfcCfcGfuAf(invdT) | 516 | pdTAfcGfgGfcAfaCfaUfaCfcUfuGfadTsdT |
| 28 | CAGUUUACUAGUGCCAUUA | 189 | TAAUGGCACUAGUAAACUG | 353 | CfaGfuUfuAfcUfaGfuGfcCfaUfuAf(invdT) | 517 | pdTAfaUfgGfcAfcUfaGfuAfaAfcUfgdTsdT |
| 29 | UGGUGGACUUCUCUCAAUU | 190 | AAUUGAGAGAAGUCCACCA | 354 | ugGuGGAcuucucucAAuudTsdT | 518 | AAUUGAGAGAAGUCcACcAdTsdT |
| 30 | AGGUAUGUUGCCCGUUUGA | 191 | TCAAACGGGCAACAUACCU | 355 | AfgGfuAfuGfuUfgCfcCfgUfuUfgAf(invdT) | 519 | pdTCfaAfaCfgGfgCfaAfcAfuAfcCfudTsdT |
| 31 | CUGCUCGUGUUACAGGCGG | 192 | CCGCCUGUAACACGAGCAG | 356 | cuGcucGuGuuAcAGGcGGdTsdT | 520 | CCGCCUGuAAcACGAGcAGdTsdT |
| 32 | UAUGUUGCCCGUUUGUCCU | 193 | AGGACAAACGGGCAACAUA | 357 | uauGuuGcccGuuuGuccudTsdT | 521 | AGGAcAAACGGGcAAcAuAdTsdT |
| 33 | UCAAGGUAUGUUGCCCGUU | 194 | AACGGGCAACAUACCUUGA | 358 | ucAAGGuAuGuuGcccGuudTsdT | 522 | AACGGGcAAcAuAcCUUGAdTsdT |
| 34 | UCUUAUCAACACUUCCGGA | 195 | UCCGGAAGUGUUGAUAAGA | 359 | ucuuAucAAcAcuuccGGAdTsdT | 523 | UCCGGAAGUGUUGAuAAGAdTsdT |
| 34 | UCUUAUCAACACUUCCGGA | 196 | TCCGGAAGUGUUGAUAAGA | 360 | UfcUfuAfuCfaAfcAfcUfuCfcGfgAf(invdT) | 524 | pdTCfcGfgAfaGfuGfuUfgAfuAfaGfadTsdT |
| 35 | CACCUCUGCCUAAUCAUCU | 197 | AGAUGAUUAGGCAGAGGUG | 361 | cAccucuGccuAAucAucudTsdT | 525 | AGAUGAUuAGGcAGAGGUGdTsdT |
| 36 | AUAAGAGGACUCUUGGACU | 198 | AGUCCAAGAGUCCUCUUAU | 362 | auAAGAGGAcucuuGGAcudTsdT | 526 | AGUCcAAGAGUCCUCUuAUdTsdT |
| 37 | GUCUGCGGCGUUUUAUCAA | 199 | TUGAUAAAACGCCGCAGAC | 363 | GfuCfuGfcGfgCfgUfuUfuAfuCfaAf(invdT) | 527 | pdTUfgAfuAfaAfaCfgCfcGfcAfgAfcdTsdT |
| 38 | GGGCCUGAAUCCCGCGGAC | 200 | GUCCGCGGGAUUCAGCGCC | 364 | ggGccuGAAucccGcGGAcdTsdT | 528 | GUCCGCGGGAUUcAGCGCCdTsdT |
| 39 | CGGCGUCGCAGAAGAUCUCA | 201 | UGAGAUCUUCUGCGACGCG | 365 | cgGcGucGcAGAAGAucucAdTsdT | 529 | UGAGAUCUUCUGCGACGCGdTsdT |

FIG. 4C

| | | | | | |
|---|---|---|---|---|---|
| 40 | AAUGUCAACGACCGACCUU | 202 | AAGGUCGGUCGUUGACAUU | 366 | aauGucAAcGAccGAccuudTsdT | 530 | AAGGUCGGUCGUUGAcAUUdTsdT |
| 41 | GCUCAGUUUACUAGUGCCA | 203 | UGGCACUAGUAAACUGAGC | 367 | gcucAGuuuAcuAGuGccAdTsdT | 531 | UGGcACuAGuAAACUGAGCdTsdT |
| 42 | UGGUGGACUUCUCUCAAUA | 204 | TAUUGAGAGAAGUCCACCA | 368 | UfgGfuGfgAfcUfuCfuCfuCfaAfuAf(invdT) | 532 | pdTAfuUfgAfgAfgAfaGfuCfcAfcCfadTsdT |
| 43 | AUCGCCGCGUCGCAGAAGA | 205 | UCUUCUGCGACGCGGCGAU | 369 | aucGccGcGucGcAGAAGAdTsdT | 533 | UCUUCUGCGACGCGGCGAUdTsdT |
| 44 | GCCAUUUGUUCAGUGGUUC | 206 | GAACCACUGAACAAAUGGC | 370 | gccAuuuGuucAGuGGuucdTsdT | 534 | GAACCACUGAAcAAAUGGCdTsdT |
| 45 | CGAUCCAUACUGCGGAACU | 207 | AGUUCCGCAGUAUGGAUCG | 371 | cgAuccAuAcuGcGGAAcudTsdT | 535 | AGUUCCGcAGuAUGGAUCGdTsdT |
| 46 | UCACCUCUGCCUAAUCAUC | 208 | GAUGAUUAGGCAGAGGUGA | 372 | ucAccucuGccuAAucAucdTsdT | 536 | GAUGAUuAGGcAGAGGUGAdTsdT |
| 47 | GUGGACUUCUCUCAAUUUU | 209 | AAAAUUGAGAGAAGUCCAC | 373 | guGGAcuucucucAAuuuudTsdT | 537 | AAAAUUGAGAGAAGUCCACdTsdT |
| 48 | GGGUCACCAUAUUCUUGGG | 210 | CCCAAGAAUAUGGUGACCC | 374 | gggUcAccAuAuucuuGGGdTsdT | 538 | CCcAAGAAuAUGGUGACCCdTsdT |
| 49 | GCCGCGUCGCAGAAGAUCU | 211 | AGAUCUUCUGCGACGCGGC | 375 | gccGcGucGcAGAAGAucudTsdT | 539 | AGAUCUUCUGCGACGCGGCdTsdT |
| 50 | UCAAUCGCCGGCGUCGCAGA | 212 | UCUGCGACGCCGGCGAUUGA | 376 | ucAAucGccGcGucGcAGAdTsdT | 540 | UCUGCGACGCGGCGAUUGAdTsdT |
| 51 | UGGAUGUGCUGCGGCGUU | 213 | AACGCCGCAGACACAUCCA | 377 | ugGAuGuGcuGcGGCGudTsdT | 541 | AACGCCGcAGAcAcAUCCAdTsdT |
| 52 | UACUGUUCAAGCCUCCAAG | 214 | CUUGGAGGCUUGAACAGUA | 378 | uacuGuucAAGccuccAAG | 542 | CUUGGAGGCUUGAAcAGuAdTsdT |
| 53 | GUUUACUAGUGCCAUUUGU | 215 | ACAAAUGGCACUAGUAAAC | 379 | guuuAcuAGuGccAuuuGu | 543 | AcAAAUGGcACuAGuAAACdTsdT |
| 54 | ACUAGUGCCAUUUGUUCAG | 216 | CUGAACAAAUGGCACUAGU | 380 | acuAGuGccAuuuGuucAG | 544 | CUGAAcAAAUGGcACuAGUdTsdT |
| 55 | CCGCGUCGCAGAGAUCUC | 217 | GAGAUCUUCUGCGACGCGG | 381 | ccGcGucGcAGAAGAucuc | 545 | GAGAUCUUCUGCGACGCGGdTsdT |

FIG. 4D

| # | Seq 1 | # | Seq 2 | # | Seq 3 |
|---|---|---|---|---|---|
| 56 | UAUCUUAUCAACACUUCCG | 218 | CGGAAGUGUUGAUAAGAU A | 382 | uaucuuAucAAcAcuuccGdTsdT | 546 | CGGAAGUGUUGAuAAGAuA dTsdT |
| 57 | GGCCAAAAUUCGCAGUCCC | 219 | GGGACUGCGAAUUUUGGCC | 383 | ggccAAAAuucGcAGucccdTsdT | 547 | GGGACUGCGAAUUUUGGCC dTsdT |
| 58 | UUCACCUCUGCCUAAUCAU | 220 | AUGAUUAGGCAGAGGUGA A | 384 | uucAccucuGccuAAucAudTsdT | 548 | AUGAUuAGGcAGAGGUGAA dTsdT |
| 59 | CUCAGUUUACUAGUGCCAU | 221 | AUGGCACUAGUAAACUGAG | 385 | cucAGuuuAcuAGuGccAudTsdT | 549 | AUGGcACuAGuAAACUGAG dTsdT |
| 60 | UGUUGCCCGUUUGUCCUCU | 222 | AGAGGACAAACGGGCAACA | 386 | uguuGcccGuuuGuccucudTsdT | 550 | AGAGGAcAAACGGGcAAcAd TsdT |
| 61 | UAGUGCCAUUUGUUCAGUG | 223 | CACUGAACAAAUGGCACUA | 387 | uaGuGccAuuuGuucAGuGdTsdT | 551 | cACUGAAcAAAUGGcACuAd TsdT |
| 62 | AGGCUGUAGGCAUAAAUUG | 224 | CAAUUUAUGCCUACAGCCU | 388 | agGcuGuAGGcAuAAAuuGdTsdT | 552 | cAAUUuAUGCCuAcAGCCUd TsdT |
| 63 | AUGUGUCUGCGGCGUUUUA | 225 | UAAAACGCCGCAGACACAU | 389 | auGuGucuGcGGcGuuuuAdTsdT | 553 | uAAAACGCCGcAGAcAcAUd TsdT |
| 63 | AUGUGUCUGCGGCGUUUUA | 226 | TAAAACGCCGCAGACACAU | 390 | AfuGfuGfucfuGfcGfcGfgUfuUfuAf(invdT) | 554 | pdTAfAfAfaCfgCfcGfcAfgAfcA fcAfudTsdT |
| 64 | ACUUCGCUUCACCUCUGCA | 227 | UGCAGAGGUGAAGCGAAGU | 391 | acuucGcuucAccucuGcAdTsdT | 555 | UGcAGAGGUGAAGCGAAGU dTsdT |
| 65 | CGUGUGCACUUCGCUUCAC | 228 | GUGAAGCGAAGUGCACACG | 392 | cguGuGcAcuucGcuucAcdTsdT | 556 | GUGAAGCGAAGUGcAcACG dTsdT |
| 66 | GUGGUGGACUUCUCUAAU | 229 | AUUGAGAGAAGUCCACCAC | 393 | guGuGGAcuucucuAAudTsdT | 557 | AUUGAGAGAAGUCCAcCAcd TsdT |
| 67 | UGUGUCUGCGGCGUUUUAU | 230 | AUAAAACGCCGCAGACACA | 394 | uguGucuGcGGcGuuuuAudTsdT | 558 | AuAAAACGCCGcAGAcAcAdT sdT |
| 68 | AAGGUAUGUUGCCGUUUG | 231 | CAAACGGCAACAUACCUU | 395 | aaGGuAuGuuGcccGuuuGdTsdT | 559 | cAAACGGGcAAcAuACCUUd TsdT |
| 69 | UCAACGACCGACCUUGAGG | 232 | CCUCAAGGUCGGUCGUUGA | 396 | ucAAcGAccGAccuuGAGGdTsdT | 560 | CCUcAAGGUCGGUCGUUGA dTsdT |
| 70 | CAUAAAGAGGACUCUUGGAC | 233 | GUCCAAGAGUCCUCUUAUG | 397 | cauAAGAGGAcucuuGGAcdTsdT | 561 | GUCcAAGAGUCCUCUuAUG dTsdT |

FIG. 4E

| | | | | | |
|---|---|---|---|---|---|
| 71 | GUCAACGACCGACCUUG AG | 234 | CUCAAGGUCGGUCGUUGAC | 398 | gucAAcGAccGAccuuGAG dTsdT | 562 | CUcAAGGUCGGUCGUUGAC dTsdT |
| 72 | AUAUUCUUGGGAACAA GAG | 235 | CUCUUGUUCCCAAGAAUAU | 399 | auAuucuuGGGAAcAAGA GdTsdT | 563 | CUCUUGUUcccAAGAAuAU dTsdT |
| 73 | UGCUCGUGUUACAGGC GGG | 236 | CCCGCCUGUAACACGAGCA | 400 | ugcucGuGuuAcAGGcGG GdTsdT | 564 | CCCGCCUGuAAcACGAGcAd TsdT |
| 74 | CAAUCGCCGCGUCGCAG AA | 237 | UUCUGCGACGCGGCGAUUG | 401 | caAucGccGcGucGcAGAA dTsdT | 565 | UUCUGcGACGCGGCGAUUG dTsdT |
| 75 | ACUGUUCAAGCCUCCAA GC | 238 | GCUUGGAGGCUUGAACAG U | 402 | acuGuucAAGccuccAAGc dTsdT | 566 | GCUUGGAGGCUUGAAcAGU dTsdT |
| 76 | CGCCCGCGUCGCAGAAGA UC | 239 | GAUCUUCUGCGACGCGGCG | 403 | cgccGcGucGcAGAAGAuc dTsdT | 567 | GAUCUUCUGcGACGCGGCG dTsdT |
| 77 | CAUUUGUUCAGUGGUU CGU | 240 | ACGAACCACUGAACAAAUG | 404 | cauuuGuucAGuGGuucGu dTsdT | 568 | ACGAACcACUGAAcAAAUGd TsdT |
| 78 | CGCUGAAUCCGGGAC GA | 241 | UCGUCCGGGAUUCAGCG | 405 | cgcuGAAucccGcGGAcGA dTsdT | 569 | UCGUCCGcGGGAUUcAGCG dTsdT |
| 79 | UGGGUCACCAUAUUCU UGG | 242 | CCAAGAAUAUGGUGACCCA | 406 | ugGGucAccAuAuucuuGG dTsdT | 570 | CcAAGAAuAUGGUGACCcAd TsdT |
| 80 | UCCUCUGCCGAUCCAUA CU | 243 | AGUAUGGAUCGGCAGAGGA | 407 | uccucuGccGAuccAuAcud TsdT | 571 | AGuAUGGAUCGGcAGAGGA dTsdT |
| 81 | AUGUCAAGACCGACCU UG | 244 | CAAGGUCGGUCGUUGACAU | 408 | auGucAAcGAccGAccuuG TsdT | 572 | cAAGGUCGGUCGUUGAcAU dTsdT |
| 82 | CCCUCUGCCUAAUCAUCU CA | 245 | UGAGAUGAUUAGGCAGAG G | 409 | cccucuGccuaAAucAucucAd TsdT | 573 | UGAGAUGAUuAGGcAGAGG dTsdT |
| 83 | ACCGUGUGCACUUCGCU UC | 246 | GAAGCGAAGUGCACACGGU | 410 | accGuGuGcAcuucGcuuc dTsdT | 574 | GAAGCGAAGUGcACACGGU dTsdT |
| 84 | UGCCGAUCCAUAUCGGCG GA | 247 | UCCGCGAGUAUGGAUCGGCA | 411 | ugccGAuccAuAcuGcGGA dTsdT | 575 | UCCGcGAuAUGGAUCGGcA dTsdT |
| 85 | CAGAGUCUAGACUCGUG GU | 248 | ACCACGAGUCUAGACUCUG | 412 | caGAGucuAGAcucGuGud TsdT | 576 | ACcACGAGucuAGACUCUg dTsdT |
| 86 | CUGUUCAAGCCUCCAAG CU | 249 | AGCUUGGAGGCUUGAACAG | 413 | cuGuucAAGccuccAAGcu dTsdT | 577 | AGCUUGGAGGCUUGAAcAG dTsdT |

FIG. 4F

| # | Col1 | # | Col3 | # | Col5 |
|---|---|---|---|---|---|
| 87 | GGAGGCUGUAGGCAUA AAU | 250 | AUUUAUGCCUACAGCCUCC | 414 | ggAGGcuGuAGGcAuAAA udTsdT | 578 | AUUuAUGCCuAcAGCCUCCd TsdT |
| 88 | AGGAGGCUGUAGGCAU AAA | 251 | UUUAUGCCUACAGCCUCCU | 415 | agGAGGcuGuAGGcAuAA AdTsdT | 579 | UUuAUGCCuAcAGCCUCCUd TsdT |
| 89 | GGUGGACUUCUCUCAA UUU | 252 | AAAUUGAGAGAAGUCCACC | 416 | gguGGAcuucucucAAuuu dTsdT | 580 | AAAUUGAGAGAAGUCCACC dTsdT |
| 90 | GCAACUUUUUCACCUCU GC | 253 | GCAGAGGUGAAAAAGUUGC | 417 | gcAAcuuuuucAccucuGcd TsdT | 581 | GCAGAGGUGAAAAGUUGC dTsdT |
| 91 | CUGCUCGUGUUACAGGC GA | 254 | TCGCCUGUAACACGAGCAG | 418 | CfuGfcUfcGfuGfuUfaCfa GfgCfgAf(invdT) | 582 | pdTCfgCfcUfgUfaAfcAfcGfa GfcAfgdTsdT |
| 92 | CUAGUGCCAUUUGUUC AGU | 255 | ACUGAACAAAUGGCACUAG | 419 | cuAGuGccAuuuGuucAGu dTsdT | 583 | ACUGAAcAAAuGGcACuAGd TsdT |
| 93 | CUGCCGAUCCAUACUGC GG | 256 | CCGCAGUAUGGAUCGGCAG | 420 | cuGccGAuccAuAcuGcGG dTsdT | 584 | CCGcAGuAUGGAUCGGcAGd TsdT |
| 94 | GUGUGCACUUCGCUUCA CC | 257 | GGUGAAGCGAAGUGCACAC | 421 | guGuGcAcuucGcuucAccd TsdT | 585 | GGUGAAGCGAAGUGCAcAC dTsdT |
| 95 | GCUCGUGUUACAGGCG GGC | 258 | GCCCGCCUGUAACACGAGC | 422 | gcucGuGuuAcAGGcGGG cdTsdT | 586 | GCCCGCCUGuAACACGAGCd TsdT |
| 96 | CCUAUCUUAUCAACACU UC | 259 | GAAGUGUUGAUAAGAUAG G | 423 | ccuAucuuAucAAcAcuucd TsdT | 587 | GAAGUGUUGAuAAGAuAGG dTsdT |
| 97 | UCUCAAUCGCCGCGUCA CA | 260 | UGCGACGCGGCGAUUGAGA | 424 | ucucAAucGccGcGucGcA dTsdT | 588 | UGCGACGCGGCGAUUGAGA dTsdT |
| 98 | GCCCGUCUGUGCCUUCU CA | 261 | UGAGAAGGCACAGACGGGC | 425 | gcccGucuGuGccuucucAd TsdT | 589 | UGAGAAGGcAcAGACGGGC dTsdT |
| 99 | CUAUCUUAUCAACACUU CC | 262 | GGAAGUGUUGAUAAGAUA G | 426 | cuAucuuAucAAcAcuucd TsdT | 590 | GGAAGUGUUGAuAAGAuAG dTsdT |
| 100 | AUGUUGCCCGUUUGUC CUC | 263 | GAGGACAAACGGGCAACAU | 427 | auGuuGcccGuuuGuccuc dTsdT | 591 | GAGGAcAAACGGGcAACAUd TsdT |
| 101 | GUAUGUUGCCCGUUUG UCC | 264 | GGACAAACGGGCAACAUAC | 428 | guAuGuuGcccGuuuGucc dTsdT | 592 | GGAcAAACGGGcAAcAuACd TsdT |
| 102 | CUUCGCUUCACCUCUGC AC | 265 | GUGCAGAGGUGAAGCGAAG | 429 | cuucGcuucAccucuGcAd TsdT | 593 | GUGcAGAGGUGAAGCGAAG dTsdT |

FIG. 4G

| | | | | | |
|---|---|---|---|---|---|
| 103 | UGUGCACUUCGCUUCAC CU | 266 | AGGUGAAGCGAAGUGCACA | 430 | uguGcAcuucGcuucAccud TsdT | 594 | AGGUGAAGCGAAGUGcAcA dTsdT |
| 104 | GCCAAAAUUCGCAGUCC CG | 267 | CGGGACUGCGAAUUUGGC | 431 | gccAAAAuucGcAGucccG dTsdT | 595 | CGGGACUGCGAAUUUUGGC dTsdT |
| 105 | CCUGCUCGUGUUACAGG CG | 268 | CGCCUGUAACACGAGCAGG | 432 | ccuGcucGuGuuAcAGGcG TsdT | 596 | CGCCUGuAAcACGAGcAGGd TsdT |
| 106 | UGGAGUGGAUUCGC ACU | 269 | AGUGCGAAUCCACACUCCA | 433 | ugGAGuGuGGAuucGcAc udTsdT | 597 | AGUGCGAAUCCAcACUCCAd TsdT |
| 107 | AACGACCGACCUUGAGG CA | 270 | UGCCUCAAGGUCGGUCGUU | 434 | aacGAccGAccuuGAGGcA dTsdT | 598 | UGCCUcAAGGUCGGUCGUU dTsdT |
| 108 | ACAGAGUCUAGACUCGU GG | 271 | CCACGAGUCUAGACUCUGU | 435 | acAGAGucuAGAcucGuG GdTsdT | 599 | CcACGAGUCuAGACUCUGU dTsdT |
| 109 | AAUCGCCGCGUCGCAGA AG | 272 | CUUCUGCGACGCGGCGAUU | 436 | aauGccGcGucGcAGAAG dTsdT | 600 | CUUCuGCGACGCGGCGAUU dTsdT |
| 110 | GGUAUGUUGCCCGUUU GUC | 273 | GACAAACGGGCAACAUACC | 437 | gguAuGuuGcccGuuuGuc TsdT | 601 | GAcAAACGGGcAAcAuACCd TsdT |
| 111 | GCCGAUCCAUACUGGG AA | 274 | UUCCGCAGUAUGGAUCGGC | 438 | gccGAuccAuAcuGcGGAA dTsdT | 602 | UUCCGcAGuAUGGAUCGGC dTsdT |
| 112 | GCCCUAUCUUAUCAACA CU | 275 | AGUGUUGAUAAGAUAGGG C | 439 | gcccuAuccuuAucAACAcud TsdT | 603 | AGUGUUGAuAAGAuAGGGC dTsdT |
| 113 | AGUUUACUAGUGCCAU UUG | 276 | CAAAUGGCACUAGUAAACU | 440 | aguuuAcuAGuGccAuuuG dTsdT | 604 | cAAAUGGcACuAGuAAACUd TsdT |
| 114 | UGUCAAGGUCGACCUU GA | 277 | UCAAGGUCGGUCGUUGACA | 441 | ugucAAcGAccGAccuuGA dTsdT | 605 | UcAAGGUCGGUCGUUGAcA dTsdT |
| 115 | ACUUCUCUCAAUUUUCU AG | 278 | CUAGAAAAUUGAGAGAAGU | 442 | acuucucucAAuuuucuAG dTsdT | 606 | CuAGAAAAUUGAGAGAAGU dTsdT |
| 116 | GCGCGGGACGUCCUUU GUC | 279 | GACAAAGGACGUCCCGCGC | 443 | gcGcGGGAcGuccuuuGuc TsdT | 607 | GAcAAAGGACGUCCCGCGCd TsdT |
| 117 | UCUAGACUCGUGGUGG ACU | 280 | AGUCCACCACGAGUCUAGA | 444 | ucuAGAcucGuGGuGGAc udTsdT | 608 | AGUCcACCACGAGUCuAGAd TsdT |
| 118 | GAUCCAUACUGCGGAAC UC | 281 | GAGUUCCGCAGUAUGGAUC | 445 | gauccAuAcuGcGGAAcuc dTsdT | 609 | GAGUUCCGcAGuAUGGAUC dTsdT |

FIG. 4H

| 119 | CUCUGCCGAUCCAUACU GC | 282 | GCAGUAUGGAUCGGCAGAG | 446 | cucuGccGAuccAuAcuGcd TsdT | 610 | GcAGuAUGGAUCGGcAGAG dTsdT |
| 120 | UCUGCCGAUCCAUACUG CG | 283 | CGCAGUAUGGAUCGGCAGA | 447 | ucuGccGAuccAuAcuGcG dTsdT | 611 | CGcAGuAUGGAUCGGcAGA dTsdT |
| 121 | CCUCUGCCGAUCCAUAC UG | 284 | CAGUAUGGAUCGGCAGAGG | 448 | ccucGccGAuccAuAcuGd TsdT | 612 | cAGuAUGGAUCGGcAGAGG dTsdT |
| 122 | GCACCUCUCUUUACGCG GU | 285 | ACCGCGUAAAGAGAGGUGC | 449 | gcAccucucuuuAcGcGud TsdT | 613 | ACCGCGuAAAGAGAGGUGC dTsdT |
| 123 | AAGAACUCCCUCGCCUC GC | 286 | GCGAGGCGAGGGAGUUCU U | 450 | aaGAAcucccucGccucGcd TsdT | 614 | GCGAGGCGAGGGAGUUCU UdTsdT |
| 124 | GAACUCCCUCGCCUCGC AG | 287 | CUGCGAGGCGAGGGAGUUC | 451 | gaAcucccucGccucGcAGd TsdT | 615 | CUGCGAGGCGAGGGAGUUC dTsdT |
| 125 | UCUCUCAAUUUCUAGG GGC | 288 | GCCCUAGAAAAUUGAGAGA | 452 | ucucucAAuuuucuAGGGc dTsdT | 616 | GCCCuAGAAAAUUGAGAGA dTsdT |
| 126 | GGGGCACCUCUCUUUA CG | 289 | CGUAAAGAGAGGUGCCCC | 453 | ggGcGcAccucucuuuAcGd TsdT | 617 | CGuAAAGAGAGGUGCCCC dTsdT |
| 127 | CCGAUCCAUACUGCGGA AC | 290 | GUUCCGCAGUAUGGAUCGG | 454 | ccGAuccAuAcuGcGGAAc dTsdT | 618 | GUUCCGcAGuAUGGAUCGG dTsdT |
| 128 | AACUCCCUCGCCUCGCA GA | 291 | UCUGCGAGGCGAGGGAGU U | 455 | aacucccucGccucGcAGAd TsdT | 619 | UCUGCGAGGCGAGGGAGU UdTsdT |
| 129 | CUCCUCUGCCGAUCCAU AC | 292 | GUAUGGAUCGGCAGAGGA G | 456 | cuccucuGccGAuccAuAcd TsdT | 620 | GuAUGGAUCGGcAGAGGAG dTsdT |
| 130 | GGAGUGUGGAUUCGCA CUC | 293 | GAGUGCGAAUCCACACUCC | 457 | ggAGuGuGGAUucGcAcuc dTsdT | 621 | GAGUGCGAAUCcACACUCCd TsdT |
| 131 | CGGGCGCACCUCUCUUU AC | 294 | GUAAAGAGAGGUGCGCCCG | 458 | cgGGcGcAccucucuuuAcd TsdT | 622 | GuAAAGAGAGGUGCGCCCG dTsdT |
| 132 | GUCUCAAUCGCCGGUC GC | 295 | GCGACGCGGCGAUUGAGAC | 459 | gucucAAucGccGGucGcd TsdT | 623 | GCGACGCGGCGAUUGAGAC dTsdT |
| 133 | AUCCAUACUGCGGAACU CC | 296 | GGAGUUCCGCAGUAUGGA U | 460 | auccAuAcuGcGGAAcucc dTsdT | 624 | GGAGUUCCGcAGuAUGGAU dTsdT |
| 134 | CGCACCUCUCUUUACGC GG | 297 | CCGCGUAAAGAGAGGUGCG | 461 | cgcAccucucuuuAcGcGGd TsdT | 625 | CCGCGuAAAGAGAGGUGCG dTsdT |

FIG. 4I

| | | | | | |
|---|---|---|---|---|---|
| 135 | CAACGACCGACCUUGAGGC | 298 | GCCUCAAGGUCGGUCGUUG | 462 | caAcGAccGAccuuGAGGc dTsdT | 626 | GCCUcAAGGUCGGUCGUUG dTsdT |
| 136 | CCAUACUGGCGGAACUCCUA | 299 | UAGGAGUUCCGCAGUAUG G | 463 | ccAuAcuGcGGAAcuccuA dTsdT | 627 | uAGGAGUUCCGcAGuAUGG dTsdT |
| 137 | UGAAUCCCGCGGACGACCC | 300 | GGGUCGUCCGCGGGAUUCA | 464 | ugAAucccGcGGAcGAccc dTsdT | 628 | GGGUCGUCCGcGGGAUUcA dTsdT |
| 138 | AGAACUCCCUCGCCUCGCA | 301 | UGCGAGGCGAGGGAGUUC U | 465 | agAAcucccucGccucGcAd TsdT | 629 | UGCGAGGCGAGGGAGUUC UdTsdT |
| 139 | GGGCACCUCUCUUUACGC | 302 | GCGUAAAGAGAGGUGCGCC | 466 | gggCAccucucuuuAcGcd TsdT | 630 | GCGuAAAGAGAGGUGCGCC dTsdT |
| 140 | GCGCACCUCUCUUUACGCG | 303 | CGCGUAAAGAGAGGUGCGC | 467 | gcGcAccucucuuuAcGcGd TsdT | 631 | CGCGuAAAGAGAGGUGCGC dTsdT |
| 141 | GCUGAAUCCCGCGGACGAC | 304 | GUCGUCCGCGGGAUUCAGC | 468 | gcuGAAucccGcGGAcGAc TsdT | 632 | GUCGUCCGcGGGAUUcAGC dTsdT |
| 142 | CACUUGCUUCACCUCUGC | 305 | GCAGAGGUGAAGCGAAGUG | 469 | cacuuGcuucAccucuGcd TsdT | 633 | GcAGAGGUGAAGCGAAGUG dTsdT |
| 143 | CUCAAUCGCGGCGUCGC AG | 306 | CUGCGACGCCGCGAUUGAG | 470 | cucAAucGcCGcGucGcAG TsdT | 634 | CUGCGACGCCGCGAUUGAG dTsdT |
| 144 | UCCCGUCGGGCUGAAUCC | 307 | GGAUUCAGCCCGACGGGA | 471 | ucccGucGGGcuGAAucc dTsdT | 635 | GGAUUcAGCCCGACGGGA dTsdT |
| 145 | CUGAAUCCCGCGGACGACC | 308 | GGUCGUCCGCGGGAUUCAG | 472 | cuGAAucccGcGGAcGAcc dTsdT | 636 | GGUCGUCCGcGGGAUUcAG dTsdT |
| 146 | AGAGUCUAGACUCUGUG | 309 | CACCACGAGUCUAGACUCU | 473 | agAGucuAGAcucuGuGGd TsdT | 637 | cACCACGAGUCuAGACUCUd TsdT |
| 147 | UCCAUACUGGCGGAACUCCU | 310 | AGGAGUUCCGCAGUAUGGA | 474 | uccAuAcuGcGGAAcuccu dTsdT | 638 | AGGAGUUCCGcAGuAUGGA dTsdT |
| 148 | GCGCUGAAUCCCGCGGACG | 311 | CGUCCGCGGGAUUCAGCGC | 475 | gcGcuGAAucccGcGGAcG dTsdT | 639 | CGUCCGcGGGAUUcAGCGC dTsdT |
| 149 | AGUGUGGAUUCGCACUCCU | 312 | AGGAGUGCGAAUCCACACU | 476 | aguGuGGAuucGcAcuccu dTsdT | 640 | AGGAGUGCGAAUCCACACU dTsdT |
| 150 | CCCUGCUCGUGUUACAG GC | 313 | GCCUGUAACACGAGCAGGG | 477 | cccuGcucGuGuuAcAGGc dTsdT | 641 | GCCUGuAAcACGAGcAGGGd TsdT |

FIG. 4J

| 151 | GAAUCCCGGGGACGACC CG | 314 | CGGGUCGUCCGCGGGAUUC | 478 | gaAucccGcGGAcGAcccG dTsdT | 642 | CGGGUCGUCCGCGGGAUUC dTsdT |
| --- | --- | --- | --- | --- | --- | --- | --- |
| 152 | AAGCUGUGCCUUGGGU GGC | 315 | GCCACCCAAGGCACAGCUU | 479 | aaGcuGuGccuuGGGuGG cdTsdT | 643 | GCCACCcAAGGcAcAGCUUd TsdT |
| 153 | GCCCUGCUCGUGUUACA GG | 316 | CCUGUAACACGAGCAGGGC | 480 | gcccuGcucGuGuuAcAGG dTsdT | 644 | CCUGuAAcACGAGcAGGGCd TsdT |
| 154 | GUCCCGUCGGCGCUGAA UC | 317 | GAUUCAGCGCCGACGGGAC | 481 | guccCGucGGCGcuGAAuc dTsdT | 645 | GAUUcAGCGCCGACGGGAC dTsdT |
| 155 | AUCUUAUCAACACUUCC GG | 318 | CCGGAAGUGUUGAUAAGA U | 482 | aucuuAucAAcAcuuccGG dTsdT | 646 | CCGGAAGUGUUGAuAAGAU dTsdT |
| 156 | CUUAUCAACACUUCCGG AA | 319 | UUCCGGAAGUGUUGAUAA G | 483 | cuuAucAAcAcuuccGGAA dTsdT | 647 | UUCCGGAAGUGUUGAuAAG dTsdT |
| 156 | CUUAUCAACACUUCCGG AA | 320 | TUCCGGAAGUGUUGAUAAGdT | 484 | CfuUfaUfcAfaCfaCfuUfcC fgGfaAf(invdT) | 648 | pdTUfcCfgGfaAfgUfgUfuGfa UfaAfgdTsdT |

FIG. 4K

Table 5. Target site sequences of dsRNAs targeting Hepatitis B Virus

| position of 17mer in acc. AM282986.1 | Unmodified dsRNAs of table 1 SEQ ID No. pair | Unmodified dsRNAs of table 1 SEQ ID No. pair | Modified dsRNAs of table 2 SEQ ID No. pair | Modified dsRNAs of table 2 SEQ ID No. pair | 17mer target site sequence (5'-3') SEQ ID No. | 17mer target site sequence (5'-3') | genotype coverage [%] A (n=332) | genotype coverage [%] B (n=615) | genotype coverage [%] C (n=1332) | genotype coverage [%] D (n=475) |
|---|---|---|---|---|---|---|---|---|---|---|
| 456 | 1/157 | 17/177 | 321/485 | 341/505 | 649 | AAGGUAUGUUGCCCGUU | 91.3 | 94.3 | 94.9 | 78.3 |
| 383 | 3/159 | 3/160 | 323/487 | 324/488 | 650 | CUGCGGCGUUUUAUCAU | 96.7 | 95.9 | 95.9 | 94.3 |
| 1828 | 4/161 | 6/163 | 325/489 | 327/491 | 651 | CCUCUGCCUAAUCAUCU | 95.5 | 81.8 | 96.8 | 92.8 |
| 1782 | 7/164 | 2/158 | 328/492 | 322/486 | 652 | UGUAGGCAUAAAUUGGU | 97.9 | 96.1 | 95.9 | 97.5 |
| 381 | 8/165 | 8/166 | 329/493 | 330/494 | 653 | GUCUGCGGCGUUUUAUC | 96.4 | 84.9 | 94 | 93.9 |
| 679 | 9/167 | 9/168 | 331/495 | 332/496 | 654 | ACUAGUGCCAUUUGUUC | 96.4 | 90.4 | 94.9 | 94.7 |
| 687 | 11/170 | 13/173 | 334/498 | 337/501 | 655 | CAUUUGUUCAGUGGUUC | 96.7 | 90.4 | 96.1 | 97.7 |
| 1177 | 12/171 | 12/172 | 335/499 | 336/500 | 656 | CAAGUGUUUGCUGACGC | 91.3 | 95.9 | 91.8 | 77.5 |
| 677 | 14/174 | 5/162 | 338/502 | 326/490 | 657 | UUACUAGUGCCAUUUGU | 95.5 | 88.9 | 94.2 | 94.7 |
| 668 | 16/176 | 18/178 | 340/504 | 342/506 | 658 | UGGCUCAGUUUACUAGU | 97 | 94.6 | 91 | 94.7 |
| 1778 | 19/179 | 23/183 | 343/507 | 347/511 | 659 | AGGCUGUAGGCAUAAAU | 97.9 | 95.8 | 96.2 | 97.5 |
| 674 | 20/180 | 28/189 | 344/508 | 353/517 | 660 | AGUUUACUAGUGCCAUU | 95.2 | 88.3 | 93.8 | 93.9 |
| 458 | 21/181 | 30/191 | 345/509 | 355/519 | 661 | GGUAUGUUGCCCGUUUG | 94.6 | 96.1 | 98.1 | 80.2 |
| 382 | 24/184 | 37/199 | 348/512 | 363/527 | 662 | UCUGCGGCGUUUUAUCA | 96.7 | 95.6 | 95.3 | 95.8 |
| 1818 | 25/185 | 10/169 | 349/513 | 333/497 | 663 | AACUUUUUCACCUCUGC | 96.1 | 92 | 96.5 | 84.8 |
| 1576 | 26/186 | 26/187 | 350/514 | 351/515 | 664 | CGUGUGCACUUCGCUUC | 97.6 | 98.4 | 98.3 | 95.6 |
| 258 | 29/190 | 42/204 | 354/518 | 368/532 | 665 | GGUGGACUUCUCUCAAU | 91.9 | 83.6 | 97.3 | 90.5 |
| 189 | 31/192 | 91/254 | 356/520 | 418/582 | 666 | UGCUCGUGUUACAGGCG | 93.7 | 93 | 93.8 | 76 |
| 461 | 32/193 | 22/182 | 357/521 | 346/510 | 667 | AUGUUGCCCGUUUGUCC | 95.5 | 96.1 | 98.4 | 79.8 |
| 455 | 33/194 | 27/188 | 358/522 | 352/516 | 668 | CAAGGUAUGUUGCCCGU | 91 | 95.4 | 93.5 | 93.3 |
| 2317 | 34/195 | 34/196 | 359/523 | 360/524 | 669 | CUUAUCAACACUUCCGG | 89.8 | 89.8 | 94.8 | 77.7 |
| 1827 | 35/197 | 15/175 | 361/525 | 339/503 | 670 | ACCUCUGCCUAAUCAUC | 95.8 | 82.1 | 96.5 | 92.8 |
| 1655 | 36/198 | | 362/526 | | 671 | UAAGAGGACUCUUGGAC | 92.2 | 88.1 | 90.2 | 91.4 |
| 1438 | 38/200 | | 364/528 | | 672 | GCGCUGAAUCCCGCGGA | 95.5 | 94.1 | 92 | 79.6 |

FIG. 5A

| | | | | | | | |
|---|---|---|---|---|---|---|---|
| 2419 | 39/201 | | 365/529 | GCGUCGCAGAAGAUCUC | 94.6 | 89.6 | 92.3 | 83.2 |
| 1680 | 40/202 | | 366/530 | AUGUCAACGACCGACCU | 96.7 | 83.9 | 93.6 | 93.5 |
| 671 | 41/203 | | 367/531 | CUCAGUUUACUAGUGCC | 96.7 | 94.8 | 92.6 | 94.7 |
| 2414 | 43/205 | | 369/533 | UCGCCGCGUCGCAGAAG | 88.6 | 84.1 | 95.1 | 92.4 |
| 686 | 44/206 | | 370/534 | CCAUUUGUUCAGUGGUU | 96.7 | 90.4 | 96 | 97.5 |
| 1263 | 45/207 | | 371/535 | GAUCCAUACUGCGGAAC | 97.3 | 89.9 | 93.8 | 95.6 |
| 1826 | 46/208 | | 372/536 | CACCUCUGCCUAAUCAU | 96.1 | 81.8 | 96.5 | 91.6 |
| 260 | 47/209 | | 373/537 | UGGACUUCUCUCAAUUU | 91.6 | 83.4 | 97.3 | 90.7 |
| 2821 | 48/210 | | 374/538 | GGUCACCAUAUUCUUGG | 86.7 | 95.4 | 96.5 | 85.3 |
| 2417 | 49/211 | | 375/539 | CCGCUCGCAGAAGAUC | 94.9 | 94.8 | 95 | 92.2 |
| 2411 | 50/212 | | 376/540 | CAAUCGCCGCGUCGCAG | 87.7 | 84.6 | 94.3 | 90.9 |
| 375 | 51/213 | | 377/541 | GGAUGUCUGGGGCGU | 95.2 | 85.7 | 94.5 | 93.7 |
| 1859 | 52/214 | | 378/542 | ACUGUUCAAGCCUCCAA | 68.4 | 91.9 | 97 | 96.4 |
| 676 | 53/215 | | 379/543 | UUUACUAGUGCCAUUUG | 95.5 | 88.9 | 94.1 | 94.7 |
| 680 | 54/216 | | 380/544 | CUAGUGCCAUUUGUUCA | 96.1 | 90.2 | 94.9 | 94.7 |
| 2418 | 55/217 | | 381/545 | CGCGUCGCAGAAGAUCU | 95.2 | 94.8 | 95 | 92.4 |
| 2315 | 56/218 | | 382/546 | AUCUUAUCAACACUUCC | 90.1 | 89.8 | 94.8 | 78.3 |
| 303 | 57/219 | | 383/547 | GCCAAAAUUCGCAGUCC | 98.5 | 97.2 | 85.7 | 94.7 |
| 1825 | 58/220 | | 384/548 | UCACCUCUGCCUAAUCA | 96.7 | 82 | 96.6 | 92 |
| 672 | 59/221 | | 385/549 | UCAGUUUACUAGUGCCA | 94.9 | 88.5 | 93.8 | 94.1 |
| 463 | 60/222 | | 386/550 | GUUGCCGUUUGUCCUC | 94.9 | 95.1 | 98.4 | 78.9 |
| 682 | 61/223 | | 387/551 | AGUGCCAUUUGUUCAGU | 96.1 | 89.9 | 94.8 | 94.5 |
| 1779 | 62/224 | | 388/552 | GGCUGUAGGCAUAAAUU | 97.9 | 96.3 | 96.3 | 97.7 |
| 378 | 63/225 | 63/226 | 389/553 390/554 | UGUGUCUGCGGCGUUUU | 96.7 | 84.9 | 93.5 | 94.3 |
| 1584 | 64/227 | | 391/555 | CUUCGCUUCACCUCUGC | 97.6 | 98.4 | 97.9 | 95.4 |
| 1577 | 65/228 | | 392/556 | GUGCACUUCGCUUCA | 97.6 | 98.2 | 98.5 | 95.4 |
| 257 | 66/229 | | 393/557 | UGGUGGACUUCUCUCAA | 91.9 | 83.6 | 97.1 | 90.5 |
| 379 | 67/230 | | 394/558 | GUGUCUGCGGCGUUUUA | 96.1 | 84.9 | 93.6 | 94.1 |
| 457 | 68/231 | | 395/559 | AGGUAUGUUGCCCGUUU | 91.3 | 94.8 | 96.7 | 79.2 |

FIG. 5B

| | | | Sequence | | | | |
|---|---|---|---|---|---|---|---|
| 1684 | 69/232 | 396/560 | CAACGACCGACCUUGAG | 96.4 | 85.4 | 94.1 | 93.3 |
| 1654 | 70/233 | 397/561 | AUAAGAGGACUCUUGGA | 92.2 | 87.8 | 90.2 | 91.2 |
| 1683 | 71/234 | 398/562 | UCAACGACCGACCUUGA | 96.7 | 85.7 | 94.2 | 93.1 |
| 2829 | 72/235 | 399/563 | UAUUCUUGGAACAAGA | 87 | 96.7 | 97.1 | 85.1 |
| 190 | 73/236 | 400/564 | GCUCGUGUUACAGGCGG | 94.9 | 93.3 | 94 | 76 |
| 2412 | 74/237 | 401/565 | AAUCGCCGUCGCAGA | 88 | 85.7 | 95.1 | 92.8 |
| 1860 | 75/238 | 402/566 | CUGUUCAAGCCUCCAAG | 68.4 | 91.7 | 97 | 96.4 |
| 2416 | 76/239 | 403/567 | GCCGCGUCGCAGAAGAU | 88.3 | 83.6 | 93.8 | 90.7 |
| 688 | 77/240 | 404/568 | AUUUGUUCAGUGGUUCG | 96.7 | 90.6 | 96.1 | 97.7 |
| 1440 | 78/241 | 405/569 | GCUGAAUCCGCGGACG | 95.8 | 95.3 | 92.8 | 79.8 |
| 2820 | 79/242 | 406/570 | GGGUCACCAUAUUCUUG | 86.4 | 95.3 | 96.8 | 85.3 |
| 1255 | 80/243 | 407/571 | CCUCUGCCGAUCCAUAC | 97.6 | 90.2 | 94.9 | 88.8 |
| 1681 | 81/244 | 408/572 | UGUCAAGACCGACCUU | 96.7 | 85.7 | 94.3 | 93.7 |
| 1829 | 82/245 | 409/573 | CUCUGCCUAAUCAUCUC | 95.8 | 82.8 | 97 | 89.3 |
| 1575 | 83/246 | 410/574 | CCGUGUGCACUUCGCUU | 97.6 | 98.5 | 98.3 | 95.8 |
| 1260 | 84/247 | 411/575 | GCCGAUCCAUACUGCGG | 97 | 88.6 | 92.9 | 95.2 |
| 243 | 85/248 | 412/576 | AGAGUCUAGACUCGUGG | 93.7 | 96.9 | 95.7 | 96 |
| 1861 | 86/249 | 413/577 | UGUUCAAGCCUCCAAGC | 68.4 | 91.7 | 96.9 | 96.4 |
| 1777 | 87/250 | 414/578 | GAGGCUGUAGGCAUAAA | 97.9 | 95.8 | 96.3 | 97.7 |
| 1776 | 88/251 | 415/579 | GGAGGCUGUAGGCAUAA | 96.7 | 95.4 | 96.2 | 97.7 |
| 259 | 89/252 | 416/580 | GUGGACUUCUCUCAAUU | 91.9 | 83.7 | 97.5 | 90.7 |
| 1817 | 90/253 | 417/581 | CAACUUUUCACCUCUG | 95.8 | 91.7 | 96.2 | 84.4 |
| 681 | 92/255 | 419/583 | UAGUGCCAUUUGUUCAG | 96.1 | 89.9 | 94.9 | 94.7 |
| 1259 | 93/256 | 420/584 | UGCCGAUCCAUACUGCG | 96.7 | 88.5 | 92.8 | 94.9 |
| 1578 | 94/257 | 421/585 | UGUGCACUUCGCUUCAC | 97.6 | 98 | 98.6 | 95.8 |
| 191 | 95/258 | 422/586 | CUCGUGUUACAGGCGGG | 94.9 | 92.7 | 92.5 | 96 |
| 2313 | 96/259 | 423/587 | CUAUCUUAUCAACACUU | 90.1 | 89.4 | 95.3 | 78.3 |
| 2409 | 97/260 | 424/588 | CUCAAUCGCCGCGUCGC | 88.6 | 85.2 | 96.7 | 93.1 |
| 1548 | 98/261 | 425/589 | CCCGUCUGUGCCUUCUC | 97.9 | 96.7 | 95.7 | 98.1 |

FIG. 5C

| | | | Sequence | | | |
|---|---|---|---|---|---|---|
| 2314 | 99/262 | 426/590 | UAUCUUAUCAACACUUC | 90.1 | 89.8 | 94.9 | 78.3 |
| 462 | 100/263 | 427/591 | UGUUGCCCGUUUGUCCU | 95.2 | 95.3 | 98.4 | 79.2 |
| 460 | 101/264 | 428/592 | UAUGUUGCCCGUUUGUC | 95.5 | 96.1 | 98.3 | 79.6 |
| 1585 | 102/265 | 429/593 | UUCGCUUCACCUCUGCA | 97.3 | 98.4 | 97.8 | 94.7 |
| 1579 | 103/266 | 430/594 | GUGCACUUCGCUUCACC | 97.9 | 98.4 | 98.6 | 95.8 |
| 304 | 104/267 | 431/595 | CCAAAAUUCGCAGUCCC | 98.5 | 97.4 | 85.9 | 95.2 |
| 188 | 105/268 | 432/596 | CUGCUCGUGUUACAGGC | 93.7 | 93 | 93.8 | 75.8 |
| 2267 | 106/269 | 433/597 | GGAGUGGGAUUCGCAC | 93.7 | 96.4 | 94.4 | 97.3 |
| 1686 | 107/270 | 434/598 | ACGACCGACCUUGAGGC | 96.4 | 85.9 | 93.8 | 93.1 |
| 242 | 108/271 | 435/599 | CAGAGUCUAGACUCGUG | 93.1 | 96.7 | 94.9 | 92.6 |
| 2413 | 109/272 | 436/600 | AUCGCCGGUCGCAGAA | 88.6 | 84.1 | 95 | 92.8 |
| 459 | 110/273 | 437/601 | GUAUGUUGCCCGUUUGU | 95.2 | 95.9 | 98.3 | 79.6 |
| 1261 | 111/274 | 438/602 | CCGAUCCAUACUGCGGA | 97.3 | 89.8 | 94.1 | 96 |
| 2311 | 112/275 | 439/603 | CCCUAUCUUAUCAACAC | 93.7 | 88.9 | 95.3 | 78.3 |
| 675 | 113/276 | 440/604 | GUUUACUAGUGCCAUUU | 95.2 | 88.6 | 93.8 | 93.9 |
| 1682 | 114/277 | 441/605 | GUCAACGACCGACCUUG | 97 | 85.7 | 94.4 | 93.1 |
| 264 | 115/278 | 442/606 | CUUCUCUCAAUUUUCUA | 90.7 | 82 | 96.4 | 88.2 |
| 1408 | 116/279 | 443/607 | CGCGGGACGUCCUUUGU | 95.5 | 96.9 | 95.9 | 94.5 |
| 248 | 117/280 | 444/608 | CUAGACUGCGUGGUGGAC | 95.5 | 97.2 | 96.5 | 97.1 |
| 1264 | 118/281 | 445/609 | AUCCAUACUGGGAACU | 97.9 | 89.4 | 94.1 | 95.6 |
| 1257 | 119/282 | 446/610 | UCUGCCGAUCCAUACUG | 96.7 | 88.5 | 91.1 | 86.9 |
| 1258 | 120/283 | 447/611 | CUGCCGAUCCAUACUGC | 96.7 | 92.5 | 92.2 | 88.4 |
| 1256 | 121/284 | 448/612 | CUCUGCCGAUCCAUACU | 96.7 | 88.1 | 90.7 | 86.5 |
| 1527 | 122/285 | 449/613 | CACCUCUUUACGCGG | 95.8 | 94.6 | 95.9 | 98.3 |
| 2381 | 123/286 | 450/614 | AGAACUCCCUCGCCCUCG | 91.6 | 95.8 | 97.3 | 89.9 |
| 2383 | 124/287 | 451/615 | AACUCCCUCGCCCUCGA | 97.3 | 95.8 | 97.3 | 90.5 |
| 267 | 125/288 | 452/616 | CUCUCAAUUUUCUAGGG | 90.1 | 82.3 | 96.4 | 87.6 |
| 1523 | 126/289 | 453/617 | GGCGCACCCUCUUUAC | 95.5 | 95.1 | 95.6 | 97.9 |
| 1262 | 127/290 | 454/618 | CGAUCCAUACUGGGAA | 97.6 | 89.9 | 94 | 95.8 |

FIG. 5D

| | | | | | | |
|---|---|---|---|---|---|---|
| 2384 | 128/291 | 455/619 | 760 | ACUCCCUGCGCCUCGCAG | 97.6 | 95.8 | 96.9 | 90.1 |
| 1254 | 129/292 | 456/620 | 761 | UCCUCUGCCGAUCCAUA | 97.6 | 89.6 | 94.7 | 89.1 |
| 2268 | 130/293 | 457/621 | 762 | GAGUGGAUUCGCACU | 93.7 | 93.8 | 93.5 | 97.3 |
| 1522 | 131/294 | 458/622 | 763 | GGGCGCACCUCUCUUUA | 95.5 | 95.1 | 95.6 | 97.9 |
| 2408 | 132/295 | 459/623 | 764 | UCUCAAUCGCCGCUCG | 88.6 | 84.4 | 96.4 | 93.1 |
| 1265 | 133/296 | 460/624 | 765 | UCCAUACUGGGAACUC | 97.6 | 88.5 | 91.2 | 95.2 |
| 1526 | 134/297 | 461/625 | 766 | GCACCUCUUUACGCG | 95.5 | 94.8 | 95.8 | 98.3 |
| 1685 | 135/298 | 462/626 | 767 | AACGACGACCUUGAGG | 96.4 | 85.2 | 94.1 | 93.3 |
| 1267 | 136/299 | 463/627 | 768 | CAUACUGGGAACUCCU | 97.6 | 88.1 | 90.1 | 95.2 |
| 1443 | 137/300 | 464/628 | 769 | GAAUCCCGCGGACGACC | 95.5 | 95.4 | 92.3 | 79.2 |
| 2382 | 138/301 | 465/629 | 770 | GAACUCCCUCGCCUGC | 97.3 | 96.1 | 97.9 | 91.6 |
| 1524 | 139/302 | 466/630 | 771 | GCGCACCUCUCUUUACG | 95.2 | 95 | 95.6 | 97.9 |
| 1525 | 140/303 | 467/631 | 772 | CGCACCUCUCUUUACGC | 95.2 | 94.8 | 95.8 | 98.3 |
| 1441 | 141/304 | 468/632 | 773 | CUGAAUCCCGGACGA | 95.8 | 95.3 | 94.1 | 79.6 |
| 1583 | 142/305 | 469/633 | 774 | ACUUCGUUCACCUCUG | 97.6 | 98.4 | 98.2 | 96.6 |
| 2410 | 143/306 | 470/634 | 775 | UCAAUCGCCGCUCGCA | 88 | 84.6 | 94.8 | 92 |
| 1431 | 144/307 | 471/635 | 776 | CCCGUCGGCCUGAAUC | 87.7 | 93.5 | 87.7 | 94.7 |
| 1442 | 145/308 | 472/636 | 777 | UGAAUCCCGGACGAC | 95.8 | 95.4 | 92.3 | 78.9 |
| 244 | 146/309 | 473/637 | 778 | GAGUCUAGACUCGUGGU | 93.7 | 96.7 | 96 | 95.8 |
| 1266 | 147/310 | 474/638 | 779 | CCAUACUGGGAACUCC | 97.6 | 88.3 | 89.9 | 95.2 |
| 1439 | 148/311 | 475/639 | 780 | CGCUGAAUCCCGGAC | 95.8 | 94.8 | 92.1 | 79.8 |
| 2270 | 149/312 | 476/640 | 781 | GUGUGGAUUCGCACUCC | 96.1 | 94.6 | 94.6 | 97.7 |
| 187 | 150/313 | 477/641 | 782 | CCUGCUCGUGUUACAGG | 93.7 | 93.2 | 94.1 | 76 |
| 1444 | 151/314 | 478/642 | 783 | AAUCCCGCGGACGACCC | 95.5 | 95.4 | 92.4 | 79.2 |
| 1875 | 152/315 | 479/643 | 784 | AGCUGUGCCUUGGGUGG | 73.8 | 96.1 | 96.4 | 96.2 |
| 186 | 153/316 | 480/644 | 785 | CCCUGCUCGUGUUACAG | 93.7 | 93 | 93.9 | 76 |
| 1430 | 154/317 | 481/645 | 786 | UCCCGUCGGCCUGAAU | 87.3 | 93.5 | 87.6 | 94.7 |
| 2316 | 155/318 | 482/646 | 787 | UCUUAUCAACACUUCCG | 89.8 | 89.8 | 94.8 | 77.7 |
| 2318 | 156/319 156/320 | 483/647 484/648 | 788 | UUAUCAACACUUCCGA | 89.8 | 89.9 | 94.7 | 77.7 |

FIG. 5E

Table 6. NCBI Genbank accession Nos. of Hepatitis B Virus genomic sequences

Genotype A

| | | | | | | | |
|---|---|---|---|---|---|---|---|
| FJ692613 | FJ692587 | AF090838 | FJ692590 | DQ020003 | AF090839 | GQ477476 | GQ477473 |
| FJ692584 | EU859907 | AJ131570 | EU859910 | FJ349223 | FJ023662 | AY862867 | EU859928 |
| AY233287 | AY233279 | FJ692609 | AF297624 | AB270536 | GQ331048 | AM295795 | FJ692555 |
| EU859904 | FJ692610 | FJ692563 | GQ477496 | EU859934 | FJ692582 | AB453982 | EU594391 |
| FJ692579 | EU859927 | EU859942 | EU859930 | GQ477492 | AY233281 | EU594394 | FJ692588 |
| AY738141 | GQ477481 | AY934765 | AM184126 | AF143305 | EU859902 | EU859951 | AY934773 |
| GQ477482 | AY738142 | AY161141 | GQ331046 | DQ788725 | FM199974 | FJ692570 | FJ692575 |
| FJ692559 | AB453988 | AY373428 | EU859950 | EU859914 | EU859922 | GQ331047 | AY233276 |
| EU859924 | AM410963 | GQ477498 | FJ692571 | EU859948 | GQ477479 | AF143301 | EU859954 |
| GQ414522 | DQ298164 | GQ477465 | EU594395 | FJ692569 | GQ477484 | FJ692607 | EU859908 |
| FJ904434 | AJ131573 | AF418674 | AB453983 | FJ692594 | EF208113 | AF143303 | EU859898 |
| FJ692565 | AB241115 | AM184125 | GQ477477 | DQ315784 | EU859947 | EU859931 | FJ692556 |
| EU859944 | EF208115 | EU185786 | AB222707 | EU054331 | FJ692566 | AF297625 | GQ477470 |
| EU859918 | EU859941 | FJ692572 | AF043580 | GQ477501 | DQ298162 | GQ477497 | AY233288 |
| DQ788729 | FJ692560 | EU859953 | DQ315786 | AB126580 | GQ477460 | AY903452 | AY934770 |
| FJ692598 | AY934766 | AY934774 | FJ692596 | FJ692603 | U87746 | EU859911 | AY233275 |
| AY934763 | AB246317 | AY077735 | EU859916 | EU859909 | AB194952 | FJ692591 | FJ692576 |
| DQ298161 | GQ477466 | AB453980 | DQ788727 | FJ692574 | AF090841 | FJ692606 | AF043560 |
| AB194951 | FJ904411 | AM295797 | FJ692601 | EU859955 | AF143299 | GQ477504 | EU594392 |
| EU859938 | EU185788 | FM199979 | GQ477503 | AY233277 | AY233284 | AF143300 | AB453987 |
| GQ477463 | AY233282 | GQ477489 | AF143307 | AY934772 | GQ477480 | FJ692583 | EU859900 |
| AF090842 | FJ692581 | GQ477474 | EU859936 | FJ692589 | AY738143 | AY233280 | AY233283 |
| EU859944 | EU859901 | AM282986 | AF297622 | EU594390 | AM494718 | GQ477464 | FJ692580 |
| EU859925 | FM199977 | AF143302 | GQ477490 | FJ692554 | EU859926 | GQ477499 | AY738139 |
| FJ692558 | AM295799 | FJ692593 | AY902775 | EU859929 | AY128092 | AY373429 | EU185789 |
| AY738140 | GQ477487 | AY233290 | EU594393 | GQ477472 | FJ692611 | AY934764 | AB222708 |
| GQ477483 | EU859921 | AY934768 | EU859956 | AB453986 | AY233278 | FJ692562 | GQ477485 |
| FJ692578 | GQ477467 | EU859913 | AY233274 | GQ477500 | EU859906 | EU859943 | GQ477478 |
| EU859905 | GQ161813 | FJ692604 | FJ692577 | FJ692602 | AY233285 | EU410082 | EU859923 |
| FJ692585 | EF208114 | FJ349224 | AY934771 | FJ692595 | FJ692586 | FJ692608 | EU859903 |
| AY233286 | AY934767 | EU859933 | AY233289 | EU859949 | EU185787 | AF143306 | FJ349222 |
| FJ692612 | EU859940 | GQ477468 | GQ477471 | FJ692568 | AF418675 | FJ692600 | AB330371 |
| GQ477462 | FJ692561 | GQ477495 | EU859899 | EU859915 | GQ477494 | GQ477502 | AB330372 |
| EU859925 | AB241114 | AM295800 | FJ692557 | DQ315785 | GQ477469 | DQ788726 | AB330373 |
| EU086721 | DQ298165 | GQ477475 | FM199981 | GQ184323 | EU859932 | EU859917 | AJ627226 |
| AB194950 | AY034878 | GQ477488 | AB453985 | AF143304 | FJ692605 | FJ692597 | AJ627227 |
| EU859939 | EU859920 | AM295796 | EU366129 | GQ477493 | EU859912 | EU747320 | AJ627228 |
| AF143308 | GQ477486 | AB453981 | AF297623 | AF297621 | AY934769 | FM199980 | AP007263 |
| FJ692599 | FM199976 | FJ692573 | GQ477491 | EU859935 | FJ692592 | AB453984 | EU304331 |
| DQ788728 | AM295798 | EU859952 | EU859937 | DQ020002 | GQ184324 | AB453979 | EU414132 |
| EU859919 | FJ692567 | EU414134 | DQ298163 | AF090840 | EU859945 | S50225 | V00866 |
| FJ692564 | AB453989 | FM199978 | EU859946 | GQ477461 | AF143298 | | |

FIG. 6A

Genotype B

| | | | | | | | |
|---|---|---|---|---|---|---|---|
| EU306702 | GU332692 | AB073842 | AY800389 | AY206377 | AB106884 | AB073843 | FJ386688 |
| GU332701 | AB073822 | AB493832 | DQ463798 | FJ386636 | EU939630 | EU939633 | AJ131574 |
| EF473975 | AY596102 | GQ924634 | EU939670 | D23678 | FJ386656 | DQ463787 | AB073840 |
| FJ787444 | DQ904357 | AY167098 | AY596103 | DQ993680 | AB116083 | FJ386655 | AB219429 |
| D23679 | EU882001 | AB116082 | AB073823 | EF473974 | GQ377641 | AY293309 | DQ361535 |
| DQ993681 | GQ924608 | AB205122 | GQ377596 | AY781187 | AF121243 | U87747 | AB493830 |
| AY033072 | GQ924654 | EU306670 | GQ377537 | AY163870 | GQ924635 | EU564822 | DQ993710 |
| GQ924628 | EU939671 | EU939631 | EU919175 | EU306703 | FJ386676 | EU522074 | AB365445 |
| EU919174 | DQ463799 | AB106885 | GU332693 | GU332700 | AB493833 | AB205120 | EU882003 |
| FJ562311 | GQ377556 | GQ924648 | AY033073 | FJ562222 | FJ562262 | FJ386675 | FJ386582 |
| FJ386615 | GQ377568 | EU305543 | EU564823 | GQ377549 | FJ562312 | AB073847 | M54923 |
| EU939673 | DQ993683 | AB219428 | GQ377588 | GU332702 | GU332691 | AB287317 | EU660233 |
| GQ924656 | FJ386669 | AB073841 | AY217370 | EU306701 | EU939672 | EU305545 | AF121247 |
| GU332690 | GU332703 | FJ032344 | GQ924617 | FJ386634 | FJ386648 | AP011087 | GQ377573 |
| EF103278 | GQ377622 | GQ924637 | FJ386608 | FJ386668 | EU882002 | FJ032342 | EU522073 |
| GQ377602 | EU306700 | AB205121 | FJ386654 | AY206375 | DQ993711 | GQ377639 | FJ562246 |
| EU919176 | EU796068 | AY330917 | EU939632 | DQ993682 | FJ386583 | GQ924611 | EU564825 |
| AB300364 | EF473977 | GQ377643 | DQ448628 | GQ377569 | GQ924631 | AY800391 | X97851 |
| GQ377595 | FJ562260 | EU522075 | EF473976 | AB073821 | DQ993698 | EU939634 | DQ993684 |
| AY220698 | AB493831 | FJ562240 | FJ032358 | GQ377594 | AY217356 | EU939668 | AY206373 |
| GQ377625 | GU332697 | GQ924610 | AY217357 | EU306695 | EU306706 | AB471854 | AB493829 |
| AF479684 | EU919171 | EU939669 | DQ975271 | EU939629 | EU579441 | AY217368 | AB219430 |
| GU332704 | GQ377592 | EU939635 | DQ993699 | EU939675 | DQ993685 | AY596105 | EF473972 |
| EU306707 | AB073827 | AY800390 | GQ924630 | EU881998 | EU919173 | GQ924653 | DQ993686 |
| AY781183 | EU564824 | AY163869 | AB073826 | FJ386584 | EU306696 | FJ386610 | AF121245 |
| EU882004 | GQ377644 | GQ377638 | GU332696 | FJ349296 | GU332695 | EU939676 | AB073839 |
| FJ349236 | EU522072 | EU305544 | DQ377158 | AY596106 | FJ562316 | EU306705 | EU660231 |
| EU939674 | X97850 | AB287316 | GQ377604 | EF473971 | AB287329 | GU332706 | EU139543 |
| EU939628 | EU660232 | AB073846 | EU919170 | AB100695 | GQ377590 | FJ562224 | EU158262 |
| GQ924651 | AF121246 | AP011086 | GQ205440 | GU332705 | AB073825 | AB205119 | AB246335 |
| EU330998 | AB493835 | GU332707 | GQ377606 | AB287314 | EU660230 | AY217364 | AB073829 |
| EU306677 | AF282918 | EU939677 | GU332694 | DQ993708 | AY206380 | AY596109 | GQ377561 |
| EU939636 | AY206390 | AY596104 | AY217355 | AY800392 | FJ386660 | EU881997 | AB033555 |
| DQ993709 | EU487256 | AY217369 | AB241116 | EU939637 | EU306709 | GQ924603 | FJ386681 |
| AY217374 | AB241117 | AB471855 | GQ924632 | EU158263 | DQ995803 | DQ463792 | AY217358 |
| EU796071 | DQ993687 | AB073824 | EU487257 | EU330999 | FJ562289 | FJ562254 | DQ993696 |
| AP011085 | AB073858 | AB287328 | AY206391 | FJ562219 | D00329 | GU332699 | FJ518812 |
| AB287315 | EF473973 | EU306697 | AP011084 | EU564826 | AB073855 | EU439022 | AY167093 |
| EU305547 | EU306704 | FJ562259 | GQ377550 | AB073838 | AP011095 | DQ980548 | AP011089 |
| AB073845 | GQ377626 | EU919172 | AB073844 | AF121244 | DQ448620 | AB287325 | AB073849 |
| AB287319 | EU330994 | AY217365 | EU330995 | DQ993697 | GQ924641 | FM209516 | AB368295 |
| FJ562234 | EU570070 | AB073854 | AF121248 | AY217359 | EU939664 | EU306698 | GQ377629 |
| EU939666 | AB300371 | DQ448621 | AB073834 | AB033554 | EU939638 | AB287327 | AB493827 |
| FJ386600 | EU439023 | AY220703 | DQ993704 | FJ386680 | AY167102 | EU439020 | DQ995801 |

FIG. 6B

| DQ993705 | AB073828 | AP011094 | AY167101 | GQ377582 | DQ993707 | AF100308 | DQ448622 |
| AY167100 | AB287324 | EU306708 | GU357842 | AB073837 | AB010289 | AY217366 | FJ032352 |
| AB073835 | EU330989 | DQ995802 | EU939667 | EU306679 | FJ562236 | AY766463 | AB073857 |
| AF121249 | GU332698 | AB300370 | AP011088 | EU919161 | X98073 | EU939678 | GQ924621 |
| AB231909 | EU939627 | EU919162 | AB287318 | EU306684 | FJ386683 | FJ386642 | DQ993695 |
| AB246339 | DQ463793 | EU570071 | AB073848 | EU330996 | DQ993694 | DQ463790 | FJ518811 |
| FJ386682 | EU939639 | DQ448623 | EU306699 | EF494381 | EU939663 | AB073850 | AY217361 |
| AF282917 | EU939665 | GQ377542 | FJ562257 | FJ386684 | AY596110 | D23677 | DQ463797 |
| X98072 | EU330997 | AB073856 | GQ377558 | DQ448619 | AB195935 | GQ924626 | GQ924606 |
| GQ377634 | GQ377614 | DQ463791 | FJ032349 | DQ463800 | DQ993700 | AB116090 | AB212626 |
| FJ562296 | EU306678 | EU939679 | AB246340 | AB073830 | FJ787476 | EU570069 | AY596111 |
| FJ562237 | AB073836 | AY217367 | EU306710 | EU570075 | AB115551 | AF121250 | AB195934 |
| EU305548 | AY206383 | AF100309 | X98074 | EU306683 | AB117759 | AB287320 | FJ787477 |
| AB195933 | AB302095 | AY518556 | D00330 | GQ377612 | AB010292 | GQ377564 | DQ993701 |
| DQ993706 | FJ032353 | AB287326 | FJ562231 | FJ562303 | AP011090 | EU660224 | GQ924647 |
| GQ924640 | AP011096 | EU439021 | GU168597 | GQ924646 | DQ448625 | EU331000 | FJ386658 |
| EU939662 | AB246341 | GQ377565 | AY217363 | GQ924624 | GQ924644 | EU330993 | EU589335 |
| GQ377613 | EF494380 | AB287321 | EU547563 | AB010290 | DQ993702 | GQ924638 | GQ377547 |
| EU306682 | GU168596 | AF121251 | DQ463795 | DQ995804 | EU350409 | FM209513 | AB073853 |
| EU330990 | D00331 | EF134945 | FJ562253 | AB073852 | AB212625 | EU439019 | EU796067 |
| AB073831 | X98075 | GQ924627 | EU522066 | DQ448627 | AY596112 | AB219427 | AP011093 |
| DQ463801 | DQ463796 | DQ448624 | GQ377566 | FJ032357 | GQ377587 | GU168595 | AY220704 |
| GQ377525 | GQ924607 | FJ032354 | AB287322 | EU796066 | AB073832 | X98076 | DQ448626 |
| AY167097 | AY217360 | AP011091 | EF134946 | AP011092 | DQ463802 | FJ562321 | AB010291 |
| FJ562322 | EU331001 | AB073851 | EU595030 | DQ463789 | GQ377610 | EU306712 | FJ386666 |
| EU306711 | GQ377539 | GQ377519 | AY206387 | EU939661 | EU306681 | AB246342 | AB486012 |
| GQ924625 | GQ924659 | AB219426 | DQ463788 | AB493834 | FJ023634 | D50521 | AB302943 |
| EU595031 | DQ463794 | FM209512 | GQ924645 | AB493836 | FJ023635 | D50522 | AB302944 |
| AY167089 | EU939681 | GQ924639 | AB014366 | AF461360 | FJ023636 | FJ023631 | AB302945 |
| EU439024 | AY217362 | EU330992 | AB031267 | AJ627225 | FJ023637 | FJ023632 | AB362933 |
| EU660227 | X98077 | EU306680 | AB302942 | AY167094 | FJ023638 | FJ023633 | AB493828 |
| AY220697 | AJ131133 | AB073833 | EU522067 | AB246343 | AF233236 | GQ377567 | GU168594 |
| AB287323 | EF494382 | DQ993703 | GQ475340 | EU439018 | EU939660 | FJ787475 | |

Genotype C

| FJ562331 | EU439009 | EU916218 | FJ386580 | FJ386617 | FJ386677 | GQ475351 | AB250109 |
| AY781186 | D23684 | EU570067 | EU939547 | EU439015 | AB195947 | AF537372 | AB111117 |
| FJ562282 | FJ023664 | AB300366 | AY373432 | FJ032347 | EU939586 | GQ377640 | GQ924614 |
| GQ377620 | AF411411 | GQ475311 | FJ787464 | EU305540 | GQ227696 | AY330914 | DQ089764 |
| GQ475331 | EU939567 | GQ377600 | FJ787438 | EU916224 | FJ787458 | EU919168 | EU872003 |
| FJ562223 | FJ386637 | EU306722 | DQ089778 | DQ377160 | AB241110 | FJ562243 | AB026815 |
| EU916238 | AY206376 | GQ377536 | AF461043 | EU560440 | GQ377576 | EU564820 | FJ787478 |
| GQ377516 | EU939651 | AB471853 | DQ089785 | EU589339 | AB367417 | EU916204 | AF068756 |
| FJ882612 | DQ089758 | GQ377597 | EU871982 | AF533983 | EU589345 | FJ386657 | FJ787485 |

FIG. 6C

| | | | | | | | |
|---|---|---|---|---|---|---|---|
| EF137802 | EU306691 | AB198077 | AB112063 | EU939611 | AF223956 | DQ089799 | AY217373 |
| EU678475 | FJ787439 | EU916219 | EU939566 | FJ562283 | AY217372 | FJ562242 | DQ975274 |
| AB367394 | FJ787465 | EU306690 | FJ882613 | GQ377621 | DQ089765 | EU919169 | AB241111 |
| EU871983 | AB485810 | EU306723 | GQ377517 | FJ787484 | GQ924615 | EU306671 | AY167099 |
| DQ089784 | EU882000 | FJ562310 | EU439008 | FJ787479 | AB111116 | AB205123 | FJ787459 |
| GQ924655 | AB198076 | EU939650 | EF137803 | AB026814 | GQ924649 | GQ475350 | EU939610 |
| GQ924609 | AB471852 | DQ089759 | FJ562330 | FJ023659 | DQ089798 | GQ377577 | EU916225 |
| DQ089779 | GQ377601 | GQ924629 | DQ536412 | EU872002 | AF223957 | AB367416 | EU589338 |
| FJ386616 | GQ475310 | AF411410 | EU916239 | AB112348 | EU589344 | GQ227697 | EU560441 |
| EU939546 | AB300367 | FJ787445 | GQ475330 | AB367395 | EU916205 | EU939587 | EU410079 |
| FJ386581 | NC_003977 | FJ023665 | AB064314 | EU678474 | EU564821 | AB195946 | DQ377161 |
| FJ032346 | EU939559 | EU306672 | AB241112 | DQ377162 | EU522068 | EU939565 | GQ475333 |
| EU305541 | FJ787487 | AY330916 | EU939579 | FJ562261 | GQ475313 | FJ023666 | FJ562280 |
| GQ377557 | EU872001 | GQ377642 | GQ227694 | EU916226 | EU306693 | FJ787446 | AY781184 |
| DQ089766 | GQ259588 | GQ475353 | EU939584 | FJ787466 | AB471851 | AB247916 | FJ562333 |
| AB111115 | FJ032339 | AF223954 | AB195945 | EU939545 | GQ377534 | AY206389 | D16665 |
| GQ924616 | AB367415 | AB116080 | EU305542 | FJ386649 | AB367409 | AB048704 | FJ032359 |
| FJ386609 | GQ377574 | FJ386629 | GQ377554 | EU871980 | EU660228 | EU939653 | AB367429 |
| AB195939 | GQ377528 | EU939613 | AB367435 | DQ089787 | DQ993181 | AY206374 | GQ377548 |
| AB367396 | EU916206 | GQ924636 | FJ032345 | EU306720 | EU939598 | FJ386635 | EU554538 |
| AY217371 | FJ562241 | AY161139 | EU594383 | FJ562313 | EU939539 | FJ562221 | FJ882610 |
| GQ377514 | AY161138 | GQ475352 | GQ377575 | AB367428 | DQ536410 | FJ787447 | EU306692 |
| DQ377163 | AB195944 | EU306673 | EU939558 | EU796069 | FJ562332 | FJ023667 | AB300365 |
| DQ361534 | EU939585 | EU498227 | AB367397 | AB112408 | AY781185 | AF411412 | GQ475312 |
| EU916227 | GQ227695 | EU916207 | AB195938 | GQ377515 | EU939652 | GU385774 | EU522069 |
| AB300359 | EU939578 | EU589346 | EU872000 | EU554539 | AB048705 | GQ377535 | GQ377603 |
| GQ377555 | EU939612 | AB116081 | FJ787486 | FJ882611 | AY206388 | AB471850 | FJ386614 |
| EU439016 | FJ386689 | AF223955 | AB111114 | GQ377623 | EU939564 | AY220699 | DQ089786 |
| DQ478885 | FJ386674 | AB367414 | DQ089767 | FJ562281 | EU787444 | EU660229 | EU871981 |
| AB367434 | FJ386628 | FJ032338 | AY152726 | GQ475332 | EU939538 | AB367408 | FJ787467 |
| AB241113 | AF537371 | GQ377529 | DQ478899 | FJ562220 | EU939599 | EU306721 | EU939544 |
| AY206392 | EU439010 | GQ475328 | FJ787480 | AB246337 | D23681 | FJ787461 | DQ089780 |
| EU939648 | AB367432 | AB111112 | AB367412 | AF473543 | FJ386632 | AY596107 | AY040627 |
| EU939614 | FJ562328 | DQ089761 | EF688062 | AB116087 | EU939608 | FJ386578 | EU871987 |
| FJ386672 | DQ377165 | FJ386652 | GQ475308 | EU562219 | EU939654 | EU939542 | FJ562314 |
| EU414133 | EU594384 | FJ386599 | GQ377619 | FJ562308 | GQ475334 | FJ386585 | DQ377159 |
| AF411408 | EU410080 | AY217376 | GQ475354 | EU939562 | FJ562287 | AB037927 | EU306727 |
| EU939583 | EU916221 | EU678470 | EU306675 | AB176643 | FJ562226 | AB112066 | EU306694 |
| AB195942 | FJ562266 | AB111946 | EU306688 | AB241109 | FJ562334 | FJ386612 | EU916241 |
| GQ227693 | EF494377 | EU872006 | EU589340 | FJ023661 | AB113878 | DQ683578 | GQ205441 |
| GQ377553 | AB493837 | AB485808 | EU560439 | FJ787441 | FJ882617 | EU881999 | AB300363 |
| GQ475348 | GQ377618 | FJ386598 | EU717218 | FJ032343 | AY206393 | FJ386613 | FJ882616 |
| GQ377605 | GQ475355 | FJ787481 | DQ377164 | EU796072 | GQ377593 | EU871986 | FJ562227 |
| GQ475314 | GQ475309 | AB485809 | FJ562329 | EU439011 | DQ980547 | DQ089781 | GQ377624 |
| GQ377533 | EU562218 | AB026811 | GQ475329 | AF411409 | EU554542 | GQ924650 | FJ562286 |
| AP011108 | EU560438 | EU872007 | EF494376 | GQ227692 | EU306726 | FJ787460 | GQ475335 |

FIG. 6D

| | | | | | | | |
|---|---|---|---|---|---|---|---|
| AB112472 | EU589341 | DQ089760 | FJ562267 | AB195943 | FJ562315 | EU882005 | FJ562335 |
| EU306689 | AB367413 | AB111113 | EU916220 | EU939582 | GQ475315 | EU939543 | AB074756 |
| FJ562247 | GQ377572 | FJ386653 | AB288026 | FJ386673 | GQ475349 | FJ386579 | AF462041 |
| EU306674 | EU678471 | EU594385 | GQ377552 | EU939615 | AB300362 | AB113879 | Y18858 |
| EF536065 | AY217377 | EU410081 | AB367433 | EU939649 | EU916240 | AF384371 | EU939655 |
| EU939609 | AB300361 | DQ089782 | AP011099 | GQ377571 | EF536066 | EU872004 | EU916223 |
| AB202072 | FJ562258 | EU871978 | D23683 | AB471848 | GQ475356 | AB367393 | EU594386 |
| FJ386633 | EU306725 | AY707087 | FJ023663 | U87742 | AB205125 | EU678472 | EU306719 |
| AB176642 | GQ377531 | FJ562336 | AY123424 | FJ032360 | EU522071 | AB367430 | GQ924633 |
| EU939563 | EU554541 | AB074755 | FJ787443 | AB367410 | FJ386650 | FJ032340 | FJ386670 |
| D23680 | FJ386587 | FJ562278 | EU939560 | AB116078 | DQ089763 | EU439012 | EU939616 |
| FJ787440 | EU939540 | FJ562285 | EU939656 | EU589342 | GQ924613 | GQ377551 | DQ975272 |
| FJ023660 | FJ787463 | GQ475336 | EU579442 | FJ562244 | EU871999 | FJ562299 | AB195940 |
| GQ475316 | EU882006 | AF384372 | AB202071 | FJ562218 | FJ787482 | FJ562238 | EU939581 |
| GQ377607 | EU871985 | FJ882615 | FJ386630 | AB222714 | AB026812 | FJ562264 | FJ386631 |
| EU579443 | AB205118 | FJ787462 | AB195941 | EU306718 | AY217375 | AB116084 | EU939591 |
| EU939657 | FJ562225 | AB112471 | DQ975273 | EU594387 | EU678473 | EU522070 | AB195950 |
| FJ787442 | FJ562279 | GQ377530 | EU939617 | EU796070 | AB367392 | AB205124 | EU939606 |
| D23682 | EU871979 | EU554540 | FJ386671 | FJ032341 | FJ386651 | GQ475357 | Y18857 |
| EU939561 | DQ089783 | GQ377591 | EU916222 | AB367431 | EU871998 | AB222715 | AB111120 |
| FJ882614 | EU871984 | AB300360 | AY057947 | EU872005 | GQ924612 | FJ562245 | GQ924623 |
| AP011098 | FJ386611 | GQ475317 | FJ562265 | D28880 | EU670263 | AB471849 | AF223961 |
| FJ562337 | AB112065 | FJ562317 | FJ562239 | AB026813 | DQ089762 | GQ377570 | FJ562228 |
| GQ475337 | EU939541 | EU306724 | FJ562298 | FJ787483 | AB116079 | AB367411 | FJ562274 |
| FJ562284 | FJ386586 | EU939580 | AB182589 | AB115417 | EU589343 | FJ032361 | EU916233 |
| GQ377541 | DQ089773 | AP011106 | EU155828 | DQ922651 | GQ872210 | GQ377580 | AB367401 |
| DQ246215 | AB368297 | AB198081 | AY641558 | FJ562268 | DQ089792 | AB116089 | AB198080 |
| FJ032350 | EU871974 | FJ386620 | DQ315783 | EU717217 | FJ904423 | EU562217 | GQ377560 |
| AB299858 | FJ386640 | EU547558 | GQ184325 | EU306715 | EU872008 | FJ562306 | DQ980549 |
| AY220702 | EU939626 | EU939646 | FJ562295 | AB246345 | FJ787473 | FJ562248 | AP011107 |
| AB113876 | GQ475346 | FM209514 | GQ377637 | FJ562326 | AB195930 | EU306686 | AY123041 |
| AB367420 | EU916213 | EU939570 | EF494379 | AB074047 | FJ386597 | GQ475306 | FJ562255 |
| FJ386576 | EU306729 | FJ023673 | AB493839 | GU357843 | AY217378 | GQ377617 | EU916212 |
| EU872014 | AB049609 | FJ787453 | GQ475326 | GQ924643 | EU939550 | EU919163 | AF286594 |
| EU871989 | AB367400 | AJ309369 | AJ344115 | EU871995 | GQ377521 | DQ089804 | GQ475347 |
| EU306728 | EU872015 | FJ562275 | AB246338 | DQ890381 | FJ349225 | DQ922650 | AY641559 |
| EU871975 | GQ377540 | FJ562229 | FJ562307 | GQ377581 | AB195931 | GQ475327 | DQ315782 |
| AB368296 | FJ882618 | FJ386661 | AB231908 | GQ377520 | FJ386601 | AB493838 | FJ518813 |
| EU881996 | AB367421 | Y18856 | EU562216 | FJ032331 | GQ872211 | EF494378 | EU939571 |
| DQ089772 | AB113877 | AY206381 | AB116088 | FJ787472 | DQ089793 | FJ562294 | FM209515 |
| EU871988 | FJ032351 | EU939607 | AB493844 | EU872009 | EU871994 | GQ377636 | EU155829 |
| FJ386641 | AF223960 | GQ924622 | GQ377616 | DQ986375 | GQ924642 | FJ562327 | AY167092 |
| AB037928 | FJ562288 | AB111121 | GQ475307 | AB365451 | EU871969 | AB246344 | FJ787452 |
| FJ386577 | EU916232 | AB195951 | EU306687 | EU939551 | FJ562235 | EU306714 | FJ023672 |
| AY596108 | AY247032 | EU939590 | FJ562249 | FJ386596 | FJ562269 | EU717216 | EU939647 |
| EU547559 | FJ562304 | FJ787471 | GQ475324 | FJ518810 | DQ478900 | EU881995 | GQ377543 |

FIG. 6E

| | | | | | | | |
|---|---|---|---|---|---|---|---|
| FJ386621 | EU562215 | DQ986376 | GQ377635 | EU939572 | AP011104 | DQ089771 | DQ993688 |
| FJ032332 | D50489 | AB365452 | FJ562297 | FJ562318 | AB367402 | AF498266 | AB195952 |
| GQ377523 | DQ089790 | DQ315781 | EU939618 | FJ562256 | FJ787490 | GQ475338 | EU939593 |
| AB206817 | EU871997 | AB042284 | EU939644 | EU916211 | EU872016 | EU916231 | AB111122 |
| AB300373 | FJ386602 | FJ562324 | FJ386622 | GQ475318 | FJ386574 | AY247031 | AF458664 |
| GQ377615 | EU939552 | EU594388 | AB033557 | GQ377609 | AF182802 | FJ562276 | FJ386662 |
| AB493847 | FJ386595 | EU306717 | AY167091 | GQ475344 | FJ386589 | AB367422 | AY206382 |
| EU570072 | AB115418 | EU717215 | FJ023671 | GQ377563 | EU939624 | AY220700 | Y18855 |
| AB116076 | AB195932 | AY057948 | FJ787451 | AB198083 | EU871976 | AP011097 | EU939658 |
| EU939604 | EU306716 | EU871996 | AB206816 | AB195953 | GQ377628 | AM180624 | GQ475319 |
| FJ787450 | AB246346 | DQ089791 | GQ377522 | DQ993689 | FJ562339 | FJ386575 | EU916210 |
| FJ023670 | FJ562325 | FJ386603 | GQ377583 | GQ372968 | FJ386643 | AP011105 | EU717212 |
| AY167090 | AB042285 | EU570073 | GQ924620 | AY220701 | EU939625 | DQ478901 | EU589337 |
| EU939573 | GQ475325 | EU306685 | AB111123 | AB113875 | DQ089770 | AB198082 | FJ562323 |
| FJ386623 | GQ184326 | GQ475305 | AF458665 | AB367423 | EU871977 | GQ377562 | AB042283 |
| EU939645 | FJ386594 | AB300372 | EU939605 | FJ562277 | EU872017 | AB367403 | GQ475323 |
| EU939619 | EU939553 | FJ562305 | EU939659 | AY247030 | AY077736 | FJ562319 | GQ377632 |
| AB033556 | FJ787470 | AB116077 | FJ386663 | EU916230 | FJ386588 | GQ377608 | FJ562290 |
| EU717214 | AJ748098 | FJ032333 | EU939592 | GQ475339 | AF182803 | GQ475345 | FJ386679 |
| FJ386625 | AB367419 | AB111119 | EU439007 | DQ089756 | AP011103 | EU939549 | EU939554 |
| EU939643 | GQ377524 | EU871990 | AB367425 | EU939603 | GQ377599 | AF182805 | AB426467 |
| AB033550 | GQ377578 | DQ089797 | GQ377518 | AY206385 | AB198079 | EU547561 | DQ089796 |
| FJ787456 | GQ377585 | FJ386605 | GQ377544 | FJ386639 | AB198084 | FJ386645 | EU871991 |
| AY167096 | DQ980551 | FJ386659 | AB195955 | FJ386665 | GQ377538 | FJ386619 | AB111118 |
| EU939575 | AB493840 | EU939555 | EU939594 | AY206378 | AB367405 | EU939623 | FJ386604 |
| DQ993693 | EU919166 | FJ386592 | FJ349241 | AB300368 | AY641561 | AY306136 | EU919167 |
| EU939588 | AB298721 | FJ562271 | EU939569 | GQ475343 | DQ089800 | DQ089776 | AB493841 |
| AB195949 | AB049610 | EU916236 | AJ309370 | EU916216 | FJ787436 | EU871971 | EU570074 |
| FJ032335 | AF223958 | FJ032355 | AB111125 | FJ562251 | EU872011 | FJ386593 | AF223959 |
| FJ562302 | AF182804 | FJ787468 | FJ787489 | EU939597 | AB493843 | AB014385 | FJ023643 |
| AB298720 | EU939548 | EU871973 | EU939557 | EU939536 | GQ377611 | AB014389 | FJ023644 |
| AB367418 | AB198078 | GQ924658 | AB195937 | AB367406 | EU919165 | AB014391 | FJ023645 |
| FJ032334 | GQ377598 | GQ924604 | AB367398 | AY641562 | GQ377527 | AB014392 | FJ023646 |
| GQ377584 | AP011102 | DQ089774 | D12980 | DQ089803 | GQ377586 | AB014393 | FJ023647 |
| DQ980550 | DQ089801 | DQ089789 | GQ377526 | AP011100 | FJ032336 | AB014394 | FJ023648 |
| GQ377579 | EU660225 | EU939621 | FJ032337 | EU916215 | FJ787488 | AB014396 | FJ023649 |
| FJ787457 | AY641560 | AB106895 | FJ562301 | FJ562252 | AB367399 | AB014399 | FJ023650 |
| AB195948 | AB367404 | FJ386647 | EU919164 | AY066028 | AB195936 | AB031262 | FJ023653 |
| EU939589 | EU570068 | EU916214 | AF536524 | FJ562340 | EU939556 | AB031265 | FJ023654 |
| DQ993692 | FJ562250 | GQ475341 | AB493842 | DQ089788 | FJ386591 | AB076678 | FJ023656 |
| EU939574 | EU916217 | DQ089802 | EU916208 | DQ089775 | FJ386606 | AB076679 | FJ023657 |
| EU939642 | GQ475342 | EU660226 | AB033552 | EU871972 | GU357845 | AB105172 | FJ023658 |
| FJ386685 | AB300369 | EU439025 | EU939641 | FJ386646 | GQ924619 | AB105173 | FJ023668 |
| FJ386624 | DQ089757 | AY641563 | FJ386686 | EU547562 | DQ089769 | AB105174 | FJ023674 |
| FJ386678 | AB111124 | AB367407 | FJ386627 | EU939620 | EU871993 | AB116085 | FJ023675 |
| AB033551 | AY206379 | AP011101 | DQ993691 | FJ787469 | DQ089794 | AB362931 | FJ023676 |

FIG. 6F

| AB042282 | FJ386664 | FJ787448 | EU939577 | EU872012 | AB014360 | AB362932 | L08805 |
|---|---|---|---|---|---|---|---|
| EU589336 | FJ386638 | EU939537 | FJ787454 | GQ475320 | AB014362 | AB367800 | L13994 |
| M38636 | AY206384 | EU939596 | FJ562233 | FJ562293 | AB014363 | AB367803 | M38454 |
| EU717213 | EU939602 | AB195957 | EU916228 | GQ377631 | AB014364 | AB367804 | S75184 |
| FJ562230 | EU939568 | FJ386667 | FJ562292 | EU916229 | AB014365 | AF461357 | V00867 |
| GQ377633 | EU939595 | EU939601 | GQ377630 | FJ562232 | AB014367 | AF461358 | X01587 |
| FJ562291 | AB195954 | AF363962 | GQ475321 | EU717211 | AB014369 | AF461359 | X02763 |
| GQ475322 | AJ309371 | EU916234 | AB205152 | EU306713 | AB014370 | AF461361 | X04615 |
| AB050018 | AB367424 | FJ562273 | EU554537 | FJ562320 | AB014371 | AF461363 | X14193 |
| GQ377559 | EU439006 | EU554536 | FJ032356 | EU939576 | AB014372 | AJ012207 | X52939 |
| FJ032348 | EU554535 | GQ377546 | AF241410 | AF330110 | AB014374 | D00630 | X70185 |
| EU939622 | GQ377545 | AB367427 | AB367426 | DQ993690 | AB014376 | D16666 | X75656 |
| FJ386618 | AB117758 | AF241411 | AF363963 | FJ787455 | AB014377 | D16667 | X75665 |
| EU547560 | DQ922649 | EU439005 | FJ562272 | AY167095 | AB014378 | D50517 | Z35717 |
| FJ386644 | EU916237 | FJ386607 | EU916235 | AB033553 | AB014379 | D50518 | Z72478 |
| EU871970 | FJ562270 | DQ089795 | EU939600 | FJ386626 | AB014380 | D50519 | Z72479 |
| DQ089777 | AF363961 | EU871992 | AY206386 | FJ386687 | AB014381 | D50520 | FJ023642 |
| EU872010 | AY148342 | DQ089768 | FJ787449 | EU939640 | AB014382 | FJ023639 | AB014384 |
| FJ787437 | X51970 | GQ924618 | FJ023669 | FJ562300 | AB014383 | FJ023641 | EU916209 |
| AM180623 | EU872013 | FJ787474 | AB195956 | | | | |

Genotype D

| AY721606 | AF121240 | GU456638 | FJ349214 | EU594409 | EU594389 | GU456672 | AB330369 |
|---|---|---|---|---|---|---|---|
| FJ904397 | GQ377589 | AY161162 | EU787440 | FJ904403 | AJ344116 | M32138 | AB330370 |
| FJ904414 | EU919197 | AB270543 | GQ167302 | AY741797 | AY721612 | FJ904447 | AF280817 |
| EU787447 | AB222711 | AY236163 | AB048701 | AY721611 | DQ315780 | FJ904398 | AJ627215 |
| FJ349213 | EU594400 | GU456644 | DQ111987 | EU414141 | AY741794 | AY721609 | AJ627216 |
| GU456680 | GU456663 | GQ205382 | EU594425 | AY902770 | AY233293 | X59795 | AJ627217 |
| X97848 | EU921418 | EU594427 | GQ205380 | AB119256 | FJ904420 | EU787437 | AJ627218 |
| AJ131956 | DQ315777 | DQ486024 | GU456646 | AB493845 | EU414142 | FJ904438 | AJ627219 |
| FJ349233 | L27106 | AB188245 | FJ349228 | X80925 | AY902773 | AY161157 | AJ627220 |
| AB270546 | AB270544 | AB205127 | AB270541 | AY862864 | GU456649 | GU456651 | AJ627221 |
| FJ562263 | AY236164 | EU787442 | AF121239 | GU456657 | AB119255 | AB090269 | AJ627222 |
| EU414136 | FJ904436 | FJ349216 | AY236161 | EU594434 | AB493846 | EU594432 | AJ627223 |
| GU456661 | AY161159 | AF418687 | GU456666 | AY161151 | GU456675 | EU939680 | AJ627224 |
| AB210821 | AY373430 | GU456678 | AB033559 | AB270550 | EU594416 | EF103276 | DQ336674 |
| EU594402 | EU787439 | AB048703 | EU594405 | EU594397 | FJ904440 | AY796030 | DQ336675 |
| FJ904408 | FJ349231 | EU594398 | FJ349208 | GQ477455 | GQ922000 | AM494716 | DQ336676 |
| AF121242 | EF103285 | FJ904431 | AY161160 | GQ922002 | GQ477457 | FJ904418 | DQ336677 |
| DQ304548 | AY661793 | GU456658 | DQ111986 | GU456677 | EU594436 | FJ904444 | DQ336678 |
| AB222713 | DQ329357 | AB210818 | AF418684 | FJ904442 | GU456655 | GU456671 | DQ336679 |
| EU594422 | FJ349211 | AB471856 | FJ904412 | AF418688 | AY161153 | GQ477453 | DQ336680 |
| AY945307 | EU787445 | DQ304551 | AF418679 | FJ349219 | AB109476 | AY902777 | DQ336681 |
| GU456641 | FJ904416 | AB205126 | EU787441 | AB205128 | AY233295 | FJ904424 | DQ336682 |
| GQ205387 | AF418680 | FJ562309 | FJ349215 | FJ904422 | AB270548 | FJ386590 | DQ336683 |

FIG. 6G

| | | | | | | | |
|---|---|---|---|---|---|---|---|
| FJ904428 | GU456682 | DQ486025 | AF043594 | EU594428 | EU414138 | AB119251 | DQ336684 |
| AY161147 | FJ904395 | AB188244 | GQ477459 | EU414140 | FJ904406 | AY090453 | DQ336685 |
| DQ486021 | EU594382 | GQ205383 | GQ924652 | AY721610 | AF418690 | FJ904404 | DQ336686 |
| Y07587 | DQ315776 | GU456645 | FJ349235 | AY233291 | AB119253 | AF418692 | DQ336687 |
| FJ349232 | AB270545 | EU594426 | FJ904432 | AY741796 | GQ205389 | DQ315779 | DQ336688 |
| FJ904435 | EU921419 | AY236162 | AB109478 | FJ349205 | GU357846 | GQ184322 | DQ336689 |
| X97849 | EU594401 | AY741798 | AB110075 | FJ904402 | FJ349221 | GQ477452 | DQ336690 |
| GU456681 | EU414135 | AB270542 | AB222709 | GU456637 | FJ904426 | GQ922005 | DQ336692 |
| FJ904415 | GU456662 | AY161163 | EF103281 | EU594408 | AY161149 | GU456670 | DQ464164 |
| FJ349212 | AB210822 | AB267090 | FJ349209 | AB119254 | AY721608 | FJ904445 | DQ464165 |
| EU787446 | AB222710 | EU594406 | AY161161 | GU456648 | FJ904399 | EU155893 | DQ464166 |
| AB116266 | AB270539 | GU456639 | AB033558 | AY902772 | FJ904446 | FJ904419 | DQ464167 |
| FJ904396 | AF121241 | GU456665 | GU456667 | EU414143 | GU456673 | DQ991753 | DQ464168 |
| AF043593 | AB078033 | AB471857 | EU594404 | AB090270 | EU594410 | AY796031 | DQ464169 |
| AY721607 | DQ486022 | GQ377532 | AY236160 | FJ904421 | AY796032 | EF103277 | DQ464170 |
| AB188241 | AB188243 | DQ304550 | AB246348 | AY741795 | AY161155 | GU456650 | DQ464172 |
| FJ904429 | GQ205379 | AB210819 | AB270540 | AY233292 | EU594430 | EU594433 | DQ464173 |
| AB078031 | GU456642 | GU456659 | FJ349229 | AJ132335 | GU456653 | AB090268 | DQ464174 |
| EU594423 | GQ205384 | FJ904430 | EU594424 | AB246347 | AY902769 | EU787436 | DQ464175 |
| GQ205386 | EU594421 | EU594399 | GU456647 | AJ344117 | FJ349220 | AY161156 | DQ464178 |
| GU456640 | FJ904394 | GU456684 | GQ205381 | DQ399006 | AY161148 | FJ904439 | DQ464181 |
| AY341335 | AY721605 | GU456679 | AB493848 | GU456668 | FJ904427 | AB126581 | DQ464182 |
| AB222712 | GU456683 | GQ167301 | AF418689 | FJ904401 | AY902774 | AY233296 | GQ922004 |
| DQ304549 | FJ349210 | AB048702 | FJ904443 | FJ349206 | GQ205388 | DQ315778 | X02496 |
| FJ904409 | AF418681 | FJ349217 | FJ349218 | AB109477 | AB119252 | FJ904405 | X65257 |
| AB210820 | FJ904417 | EU787443 | EU594415 | X80926 | DQ304547 | AY090452 | X65258 |
| GU456660 | EF103279 | AF418686 | GU456676 | AY161152 | AF418691 | AB270537 | X65259 |
| EU414137 | AY661792 | FJ904410 | GQ477454 | GU456654 | FJ904407 | FJ904425 | X68292 |
| EU594403 | DQ329356 | EF103280 | EU594396 | GQ922001 | EU414139 | AY902776 | X72702 |
| AB270547 | AY373431 | AB109479 | GQ922003 | FJ562338 | AB270549 | GQ205377 | X85254 |
| GQ205385 | AY161158 | AM422939 | AY161150 | GQ477456 | U95551 | AB104709 | Z35716 |
| GU456643 | FJ904437 | FJ349234 | GU456656 | FJ904441 | AY233294 | AB104710 | V01460 |
| GQ205378 | FJ349230 | FJ904433 | EU594435 | GU456674 | EU594431 | AB104711 | AB330368 |
| DQ486023 | EU787438 | GQ477458 | AF151735 | FJ904400 | AY902768 | AB104712 | EF103275 |
| AB078032 | EU594407 | GQ377627 | X80924 | FJ349207 | GU456652 | AB330366 | GU456635 |
| AB188242 | AB120308 | FJ904413 | AB109475 | GU456669 | AY161154 | AB330367 | GU456636 |
| AB270538 | GU456664 | AF418685 | | | | | |

FIG. 6H

Table 7. Comparision of knockdown efficacies and coverage of HBV genomes for single dsRNAs and combinations thereof.

| SEQ ID NO pair | dsRNA 1 1nM [%] rem. Rluc | dsRNA 1 1nM rank | dsRNA 1 % coverage (of 2754 genomes) | SEQ ID NO pair | dsRNA2 1nM [%] rem. Rluc | dsRNA2 1nM rank | dsRNA2 % coverage (of 2754 genomes) | 10 nM [%] rem. Rluc | Combination of dsRNA 1+2 1 nM [%] rem. Rluc | 1 nM rank | % coverage (of 2754 genomes) | Genomes not matched |
|---|---|---|---|---|---|---|---|---|---|---|---|---|
| 322/486 | 14 | 1 | 96.4 | 333/497 | 21 | 7 | 93.5 | 5 | 25 | 1 | 99.67 | 9 |
| 322/486 | 14 | 1 | 96.4 | 346/510 | 35 | 13 | 94.3 | 7 | 26 | 2 | 99.82 | 5 |
| 322/486 | 14 | 1 | 96.4 | 330/494 | 20 | 5 | 92.2 | 6 | 28 | 3 | 99.67 | 9 |
| 322/486 | 14 | 1 | 96.4 | 324/488 | 15 | 2 | 95.8 | 5 | 29 | 4 | 99.85 | 4 |
| 327/491 | 19 | 4 | 92.6 | 322/486 | 14 | 1 | 96.4 | 5 | 30 | 5 | 99.64 | 10 |
| 327/491 | 19 | 4 | 92.6 | 326/490 | 17 | 3 | 93.3 | 4 | 30 | 6 | 99.35 | 18 |
| 326/490 | 17 | 3 | 93.3 | 333/497 | 21 | 7 | 93.5 | 4 | 30 | 7 | 99.71 | 8 |
| 336/500 | 23 | 8 | 90.2 | 322/486 | 14 | 1 | 96.4 | 5 | 31 | 8 | 99.64 | 10 |
| 324/488 | 15 | 2 | 95.8 | 333/497 | 21 | 7 | 93.5 | 3 | 31 | 9 | 99.56 | 12 |
| 324/488 | 15 | 2 | 95.8 | 339/503 | 25 | 10 | 92.6 | 5 | 31 | 10 | 99.75 | 7 |
| 326/490 | 17 | 3 | 93.3 | 347/511 | 36 | 14 | 96.5 | 6 | 31 | 11 | 99.82 | 5 |
| 326/490 | 17 | 3 | 93.3 | 322/486 | 14 | 1 | 96.4 | 5 | 32 | 12 | 99.85 | 4 |
| 326/490 | 17 | 3 | 93.3 | 322/486 | 14 | 1 | 96.4 | 6 | 32 | 13 | 99.85 | 4 |
| 332/496 | 21 | 6 | 94.0 | 324/488 | 15 | 2 | 95.8 | 4 | 32 | 14 | 99.31 | 19 |
| 332/496 | 21 | 6 | 94.0 | 332/496 | 21 | 6 | 94.0 | 5 | 32 | 15 | 99.38 | 17 |
| 327/491 | 19 | 4 | 92.6 | 347/511 | 36 | 14 | 96.5 | 4 | 32 | 16 | 99.89 | 3 |
| 332/496 | 21 | 6 | 94.0 | 324/488 | 15 | 2 | 95.8 | 5 | 33 | 17 | 99.78 | 6 |
| 327/491 | 19 | 4 | 92.6 | 324/488 | 15 | 2 | 95.8 | 4 | 33 | 18 | 99.49 | 14 |
| 336/500 | 23 | 8 | 90.2 | 333/497 | 21 | 7 | 93.5 | 3 | 34 | 19 | 99.71 | 8 |
| 332/496 | 21 | 6 | 94.0 | 347/511 | 36 | 14 | 96.5 | 5 | 34 | 20 | 99.85 | 4 |
| 324/488 | 15 | 2 | 95.8 | 330/494 | 20 | 5 | 92.2 | 4 | 37 | 21 | 99.24 | 21 |
| 332/496 | 21 | 6 | 94.0 | 322/486 | 14 | 1 | 96.4 | 6 | 42 | 22 | 99.82 | 5 |
| 337/501 | 24 | 9 | 95.2 | 347/511 | 36 | 14 | 96.5 | 6 | 42 | 23 | 99.89 | 3 |

FIG. 7A

| | | | | | | | | | | |
|---|---|---|---|---|---|---|---|---|---|---|
| 337/501 | 24 | 9 | 95.2 | 324/488 | 15 | 2 | 95.8 | 5 | 43 | 24 | 99.60 | 11 |
| 337/501 | 24 | 9 | 95.2 | 333/497 | 21 | 7 | 93.5 | 6 | 44 | 25 | 99.71 | 8 |
| 337/501 | 24 | 9 | 95.2 | 336/500 | 23 | 8 | 90.2 | 7 | 47 | 26 | 99.71 | 8 |
| 341/505 | 31 | 11 | 91.5 | 322/486 | 14 | 1 | 96.4 | 5 | 50 | 27 | 99.85 | 4 |
| 341/505 | 31 | 11 | 91.5 | 324/488 | 15 | 2 | 95.8 | 5 | 57 | 28 | 99.67 | 9 |
| 351/515 | 38 | 15 | 97.7 | 337/501 | 24 | 9 | 95.2 | 6 | 60 | 29 | 99.75 | 7 |
| 351/515 | 38 | 15 | 97.7 | 342/506 | 32 | 12 | 93.2 | 8 | 60 | 30 | 99.93 | 2 |

FIG. 7B

Table 8. Sequences of the negative control ds RNAs used in the psiCHECK™-2 screening assay.

| strand | Sequence | gene |
|---|---|---|
| sense | 5'-cuuAcGcuGAGuAcuucGATsT-3', SEQ ID No. 789 | LUC(GL3) |
| antisense | 5'-UCGAAGuACUcAGCGuAAGTsT-3', SEQ ID No. 790 | LUC(GL3) |
| sense | 5'-CcAcAuGAAGcAGcACGACusU-3', SEQ ID No. 791 | GFP |
| antisense | 5'-AAGUCGUGCUGCUUCAUGUGgsusC -3', SEQ ID No. 792 | GFP |

FIG. 8

COMPOSITIONS AND METHODS FOR INHIBITING GENE EXPRESSION OF HEPATITIS B VIRUS

BACKGROUND OF THE INVENTION

This invention relates to double-stranded ribonucleic acids (dsRNAs), and their use in mediating RNA interference to inhibit the expression of genes, necessary for replication and pathogenesis of Hepatitis B Virus, in particular in the inhibition of viral polymerase, surface antigen, e-antigen and the X protein. Furthermore, the use of said dsRNAs to treat or prevent chronic liver diseases/disorders, inflammations, fibrotic conditions and proliferative disorders, like cancers, as consequence of Hepatitis B Virus infection, is part of this invention.

The Hepatitis B Virus is a strict hepatotrophic, double-stranded DNA containing virus. Although DNA is the genetic material, the replication cycle involves a reverse transcription step to copy a pregenomic RNA into DNA. In order to accomplish this essential step, the viral-encoded polymerase possesses reverse transcriptase activity. Hepatitis B virus is classified as one member of the Hepadnaviruses and belongs to the family of Hepadnaviridae. The primary infection of adult humans with Hepatitis B Virus causes an acute hepatitis with symptoms of organ inflammation, fever, jaundice and increased liver transaminases in blood. About 95% of acute hepatitis resolve without treatment. Those patients, that are not able to overcome the virus infection, suffer a chronic disease progression over many years with increased risk of developing cirrhotic liver or liver cancer. Perinatal transmission from Hepatitis B virus-infected mothers to newborns also leads to chronic hepatitis. The treatment options for chronic Hepatitis B Virus infection are limited and lead only in some cases to complete and lasting remission. Additional clinical and therapeutical complications arise in Hepatitis B Virus patients co-infected with Hepatitis C, Hepatitis D or Human Immunodeficiency Virus.

The Hepatitis B Virus is transmitted via blood or blood products, sperm, vaginal secrets, or saliva. Drug abuse and sexual intercourse are dangerous activities and support spreading the virus. Contact of damaged, mucoid epithelia with contaminated body fluids may be sufficient for infection. Incubation time is between 40 to 200 days. The risk for infection is proportional to the number of transmitted Hepatitis B Virus particles. Babies are often infected perinatally by their Hepatitis B Virus carrying mother, a major health problem in endemic areas.

About 2 billion people are infected with Hepatitis B Virus and 400 million are chronic carriers. Areas with high prevalence are Africa and South-East Asia, with local accumulation of 20-80% infected persons.

Based on sequence homology, Hepatitis B Viruses are classified into genotypes A-H, with genotypes A-D being the most important ones. Genotype A is frequent in North-Western Europe, USA, South and Central America. Genotype B and C are dominant in China, Japan, Indonesia and other countries in East Asia. Genotype D is found in Southern Europe, Northern Africa and South Africa. Disease progression and response to pharmaceutical treatment differ among genotypes.

Infectious Hepatitis B Virus particles have a diameter of about 42 nm. The outer membrane bilayer contains the large, middle and small surface protein. The cognate hepatocellular receptor for virus surface protein binding and internalization is unknown. Many copies of core protein form a spherical nucleocapsid structure inside the virus particle. Each nucleocapsid carries partial double-stranded DNA as genetic material, together with viral polymerase.

Upon uptake by hepatocytes, the nucleocapsid is transferred to the nucleus and DNA is released. There, the DNA strand synthesis is completed and gaps repaired to give the covalently closed circular (ccc) supercoiled DNA of 3.2 kb. The cccDNA serves as template for transcription of four major viral mRNAs, which are 3.5, 2.4, 2.1 and 0.7 kb long. All mRNAs are 5'-capped and polyadenylated at the 3'-end. There is sequence overlap at the 3'-end between all four mRNAs.

The 3.5 kb mRNA serves as template for core protein and polymerase production. In addition, the same transcript serves as a pre-genomic replication intermediate and allows the viral polymerase to initiate the reverse transcription into DNA. Core protein is needed for nucleocapsid formation. In addition, sequential processing activities transforms some core protein into the secretable e-antigen. The abundance of e-antigen in blood correlates with Hepatitis B Virus replication in liver and serves as important diagnostic marker for monitoring the disease progression.

The 2.4 and 2.1 kb mRNAs carry the open reading frames pre-S1, pre-S2 and S2 for expression of viral large, medium and small surface antigen. The s-antigen is associated with infectious, complete particles. In addition, blood of infected patients also contain non-infectious particles derived from s-antigen alone, free of genomic DNA or polymerase. The function of these particles is not fully understood. The complete and lasting depletion of detectable s-antigen in blood is considered as reliable indicator for Hepatitis B Virus clearance and thus, successful cure.

The 0.7 kb mRNA encodes the X protein. This gene product is important for efficient transcription of viral genes and also acts as a transactivator on host gene expression. The latter activity seems to be important for hepatocyte transformation during development of liver cancer.

Recombinant Hepatitis B Virus s-antigen is used for vaccination. The injection of three doses of formulated s-antigen at day 1, at 4 weeks and at 6 months usually induces a sufficient titer of neutralizing antibodies. Vaccinated patients are protected for 10 years or longer. However, the vaccines are no substitute for therapy.

Patients with acute Hepatitis B Virus infection are not treated due to the high, natural remission rate. However, those patients with detectable s-antigen, e-antigen or viral DNA in the blood for more than 6 months are considered chronically infected. Nucleoside analogs as inhibitors of reverse transcriptase activity are the first treatment option for many patients. Lamivudine, Tenofovir, or Entecavir suppress Hepatitis B Virus replication, sometimes to undetectable levels. Improvement of liver function and reduction of liver inflammation are the most important benefits. However, only few patients achieve complete and lasting remission after the end of treatment. Furthermore, the Hepatitis B Virus develops drug resistance with increasing duration of treatment. This is especially difficult for patients co-infected with Hepatitis B and Human Immunodeficiency Virus. Both viruses are susceptible to nucleoside analogue drugs and may co-develop resistance.

The second treatment option is the administration of interferon-alpha. Here, patients receive high doses of interferon-alpha over a period of 6 months. Depending on the virus genotype, up to 50% of chronic infection are curable. However, the Asian genotype B gives very poor response rates. Co-infection with Hepatitis D or Human Immunodeficiency Virus renders interferon-alpha therapy completely ineffective. Patients with strong liver damage and heavy fibrotic conditions are not qualified for interferon-alpha therapy.

Despite significant advances in the field of Hepatitis B Virus treatment, there remains a need for an agent that can selectively and efficiently silence the gene expression of the virus, blocks replication and subsequently reduces viral burden in chronically infected patients.

Double-stranded RNA molecules (dsRNA) have been shown to block gene expression in a highly conserved regulatory mechanism known as RNA interference (RNAi). The invention provides double-stranded ribonucleic acid molecules (dsRNAs), as well as compositions and methods for inhibiting the expression of the Hepatitis B Virus gene, in particular the expression of the Hepatitis B Virus gene, in a cell, tissue or mammal using such dsRNA. The invention also provides compositions and methods for treating or preventing pathological conditions and diseases caused by the infection of the Hepatitis B Virus such as in chronic liver diseases/disorders, inflammations, fibrotic conditions and proliferative disorders, like cancers.

SUMMARY OF THE INVENTION

The invention provides double-stranded ribonucleic acid (dsRNA) molecules able to selectively and efficiently decrease the expression of Hepatitis B Virus gene. The use of Hepatitis B Virus RNAi provides a method for the therapeutic and/or prophylactic treatment of diseases/disorders which are associated with chronic liver diseases/disorders, inflammations, fibrotic conditions and proliferative disorders, like cancers, such method comprises administration of dsRNA targeting Hepatitis B Virus to a human being or animal. In one preferred embodiment the described dsRNA molecule is capable of inhibiting the expression of a Hepatitis B Virus gene by at least 60%, preferably by at least 70%, most preferably by at least 80%.

In one embodiment, the invention provides double-stranded ribonucleic acid (dsRNA) molecules for inhibiting the expression of a Hepatitis B Virus gene, in particular the expression of the genes related to replication or pathogenesis of Hepatitis B Virus. The dsRNA comprises at least two sequences that are complementary to each other. The dsRNA comprises a sense strand comprising a first sequence and an antisense strand comprising a second sequence, see sequences provided in the sequence listing and also the specific dsRNA pairs in the appended Table 1 and Table 2. In one embodiment the sense strand comprises a sequence which has an identity of at least 90% to at least a portion of an Hepatitis B Virus mRNA. Said sequence is located in a region of complementarity of the sense strand to the antisense strand, preferably within nucleotides 2-7 of the 5' terminus of the antisense strand. In one preferred embodiment the dsRNA specifically targets the Hepatitis B Virus gene that encodes core protein, viral polymerase, surface antigen, e-antigen or the X protein. Furthermore, it is preferred that the dsRNA specifically targets a consensus sequence which has a highly conserved nucleic acid sequence among the Hepatitis B Virus genomic sequences of genotype A, B, C and D. Preferably, the consensus sequence is at least 13 contiguous nucleotides in length, more preferably at least 17 contiguous nucleotides, and most preferably at least 19 contiguous nucleotides. Preferred highly conserved nucleic acid sequences are listed in Table 5.

In one embodiment, the antisense strand comprises a nucleotide sequence which is substantially complementary to at least part of an mRNA encoding said Hepatitis B Virus gene, and the region of complementarity is most preferably less than 30 nucleotides in length. Furthermore, it is preferred that the length of the herein described inventive dsRNA molecules (duplex length) is in the range of about 16 to 30 nucleotides, in particular in the range of about 18 to 28 nucleotides. Particularly useful in context of this invention are duplex lengths of about 19, 20, 21, 22, 23 or 24 nucleotides. Most preferred are duplex stretches of 19, 21 or 23 nucleotides. The dsRNA, upon delivery to a cell infected by a Hepatitis B Virus, inhibits the expression of a Hepatitis B Virus gene in vitro by at least 60%, preferably by at least 70%, and most preferably by 80%.

BRIEF DESCRIPTION OF THE DRAWINGS

FIG. 1. Table 1. Core sequences of dsRNAs targeting Hepatitis B Virus gene. Letters in capitals represent RNA nucleotides.

FIG. 2. Table 2. Characterization of dsRNAs targeting Hepatitis B Virus: Activity testing with single dose. Letters in capitals represent RNA nucleotides, lower case letters "c", "g", "a" and "u" represent 2' O-methyl-modified nucleotides, "s" represents phosphorothioate, "dT" represents deoxythymidine, upper case letters A, C, G, U followed by "f" indicates a 2'-fluoro nucleotide. Lower case "p" indicates a 5'-phosphate. (invdT) represents an inverted deoxythimidine (3'-3'-linked).

FIG. 3. Table 3. Characterization of dsRNAs targeting Hepatitis B Virus: Stability. t½: half-life of a strand as defined in examples.

FIG. 4. Table 4. Core sequences of dsRNAs targeting Hepatitis B Virus gene and their modified counterparts. Letters in capitals represent RNA nucleotides, lower case letters "c", "g", "a" and "u" represent 2' O-methyl-modified nucleotides, "s" represents phosphorothioate, "dT" represents deoxythymidine, upper case letters A, C, G, U followed by "t" indicates a 2'-fluoro nucleotide. Lower case "p" indicates a 5'-phosphate. (invdT) represents an inverted deoxythimidine (3'-3'-linked).

FIG. 5. Table 5. Target site sequences of dsRNAs targeting Hepatitis B Virus and their coverage rate with respect to Hepatitis B Virus genotypes A, B, C and D. n=number of available HBV sequences of each genotype FIG. 6. Table 6. NCBI Genbank accession Nos. of Hepatitis B Virus genomic sequences.

FIG. 7. Table 7. Comparison of knockdown efficacies and coverage of HBV genomes for single dsRNAs and combinations thereof. Activity testing for combinations of two dsRNAs was done at final concentrations of 10 nM and at 1 nM with the best performing dsRNAs according to Table 2 and compared with respective data.

FIG. 8. Table 8. Sequences of the negative control ds RNAs used in the psiCHECK™-2 screening assay.

DETAILED DESCRIPTION OF THE INVENTION

Appended Table 1 relates to preferred molecules to be used as dsRNA in accordance with this invention. Also modified dsRNA molecules are provided herein and are in particular disclosed in appended Table 2, providing illustrative examples of modified dsRNA molecules of the present invention. As pointed out herein above, Table 2 provides for illustrative examples of modified dsRNAs of this invention (whereby the corresponding sense strand and antisense strand is provided in this Table). The relation of the unmodified preferred molecules shown in Table 1 to the modified dsRNAs of Table 2 is illustrated in Table 4. Yet, the illustrative modifications of these constituents of the inventive dsRNAs are provided herein as examples of modifications.

Table 3 provides for selective biological, clinical and pharmaceutical relevant parameters of certain dsRNA molecules of this invention.

Some of the preferred dsRNA molecules are provided in the appended Table 1 and, inter alia and preferably, wherein the sense strand is selected from the group consisting of the nucleic acid sequences depicted in SEQ ID NOs: 1, 2, 3, 4, 5, 6, 7, and 26. The antisense strand is selected from the group consisting of the nucleic acid sequences depicted in SEQ ID NOs: 157, 158, 160, 161, 162, 163, 164, and 186. Accordingly, the inventive dsRNA molecule may, inter alia, comprise the sequence pairs selected from the group consisting of SEQ ID NOs: 1/157, 2/158, 3/160, 4/161, 5/162, 6/163, 7/164, and 26/186. In the context of specific dsRNA molecules provided herein, pairs of SEQ ID NOs relate to corresponding sense and antisense strands sequences (5' to 3') as also shown in the Tables.

In one embodiment the dsRNA molecules comprise an antisense strand with a 3' overhang of 1-5 nucleotides in length, preferably 1-2 nucleotides in length. Preferably said overhang of the antisense strand comprises uracil or nucleotides which are complementary to the mRNA encoding a protein necessary for replication or pathogenesis of Hepatitis B Virus, in particular core protein, viral polymerase, surface antigen, e-antigen and X protein. In another preferred embodiment, said dsRNA molecules comprise a sense strand with a 3' overhang of 1-5 nucleotides in length, preferably 1-2 nucleotides in length. Preferably said overhang of the sense strand comprises uracil or nucleotides which are identical to the mRNA encoding a protein necessary for replication or (pathogenesis of Hepatitis B Virus.

In another preferred embodiment, the dsRNA molecules comprise a sense strand with a 3' overhang of 1-5 nucleotides in length, preferably 1-2 nucleotides in length, and an antisense strand with a 3' overhang of 1-5 nucleotides in length, preferably 1-2 nucleotides in length. Preferably said overhang of the sense strand comprises uracil or nucleotides which are at least 90% identical to the pregenomic RNA and/or the mRNA encoding the protein necessary for replication or pathogenesis of Hepatitis B Virus and said overhang of the antisense strand comprises uracil or nucleotides which are at least 90% complementary to the mRNA encoding the protein necessary for replication or pathogenesis of Hepatitis B Virus.

The dsRNA molecules of the invention may be comprised of naturally occurring nucleotides or may be comprised of at least one modified nucleotide, such as a 2'-O-methyl modified nucleotide, inverted deoxythymidine, a nucleotide comprising a 5'-phosphorothioate group, and a terminal nucleotide linked to a cholesteryl derivative or dodecanoic acid bisdecylamide group. 2' modified nucleotides may have the additional advantage that certain immunostimulatory factors or cytokines are suppressed when the inventive dsRNA molecules are employed in vivo, for example in a medical setting. Alternatively and non-limiting, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one preferred embodiment the dsRNA molecules comprises at least one of the following modified nucleotides: a 2'-β-methyl modified nucleotide, a nucleotide comprising a 5'-phosphorothioate group and a deoxythymidine. Preferred dsRNA molecules comprising modified nucleotides are given in Table 2. In another preferred embodiment one of those deoxythymidine nucleotides at the 3' of both strand is an inverted deoxythymidine.

In a preferred embodiment the inventive dsRNA molecules comprise modified nucleotides as detailed in the sequences given in Table 2. In one preferred embodiment the inventive dsRNA molecule comprises sequence pairs selected from the group consisting of SEQ ID NOs: 1/157, 2/158, 3/160, 4/161, 5/162, 6/163, 7/164, and 26/186, and comprises overhangs at the antisense and/or sense strand of 1-2 deoxythymidines. In one preferred embodiment the inventive dsRNA molecule comprises sequence pairs selected from the group consisting of SEQ ID NOs: 1/157, 2/158, 3/160, 4/161, 5/162, 6/163, 7/164, and 26/186, and comprise modifications as detailed in Table 2. Preferred dsRNA molecules comprising modified nucleotides are listed in Table 2-4, with the most preferred dsRNA molecules depicted in SEQ ID Nos: 321/485, 322/486, 324/488, 325/489, 326/490, 327/491, 328/492, and 350/514.

In another embodiment, the inventive dsRNAs comprise modified nucleotides on positions different from those disclosed in Table 2. In one preferred embodiment two deoxythymidine nucleotides are found at the 3' of both strands of the dsRNA molecule. Preferably said deoxythymidine nucleotides form an overhang.

In one embodiment the dsRNA molecules of the invention comprise a sense and an antisense strand wherein both strands have a half-life of at least 0.9 h. In one preferred embodiment the dsRNA molecules of the invention comprise a sense and an antisense strand wherein both strands have a half-life of at least 48 h, preferably in human serum.

In another embodiment, a nucleic acid sequence encoding a sense strand and/or an antisense strand comprised in the dsRNAs as defined herein are provided.

The invention also provides for cells comprising at least one of the dsRNAs of the invention. The cell is preferably a mammalian cell, such as a human cell. Furthermore, tissues and/or non-human organisms comprising the herein defined dsRNA molecules are an embodiment of this invention, whereby said non-human organisms are particularly useful for research purposes or as research tools, for example in drug testing.

Furthermore, the invention relates to a method for inhibiting the expression of a Hepatitis B Virus gene, in particular a Hepatitis B Virus gene that encodes core protein, viral polymerase, surface antigen, e-antigen or the X protein, in a cell, tissue or organism comprising the following steps:

(a) introducing into the cell, tissue or organism a double-stranded ribonucleic acid (dsRNA) as defined herein; and (b) maintaining said cell, tissue or organism produced in step (a) for a time sufficient to obtain degradation of the mRNA transcript of a Hepatitis B Virus gene, thereby inhibiting expression of a Hepatitis B Virus gene in a given cell.

The invention also relates to pharmaceutical compositions comprising at least one kind of the inventive dsRNAs. These pharmaceutical compositions are particularly useful in the inhibition of the expression of a Hepatitis B Virus gene in a cell, a tissue or an organism.

Preferably said at least one kind of the inventive double-stranded ribonucleic acid molecules target the region of a pregenomic RNA and/or a mRNA encoding a protein necessary for replication or pathogenesis of Hepatitis B Virus gene. More preferably said target region of the inventive double-stranded ribonucleic acid molecules comprises a consensus sequence which is highly conserved among the Hepatitis B Virus genomic sequences of genotype A, B, C and D, and said consensus sequence is at least 13 contiguous nucleotides in length, preferably at least 17 contiguous nucleotides, most preferably at least 19 contiguous nucleotides. Preferred highly conserved nucleic acid sequences are listed in Table 5. The pharmaceutical compositions may be used to treat patients who are infected with any genotype of Hepatitis B Virus or co-infected with different genotypes of Hepatitis B Virus.

In case the pharmaceutical composition comprises at least two kinds of inventive double-stranded ribonucleic acid molecules, it is preferable that the targets of said double-stranded ribonucleic acid molecules are different from each other. The inventive pharmaceutical compositions may be used to treat the patients and to prevent the Hepatitis B Virus from developing resistance to the pharmaceutical compositions. In a preferred embodiment the inventive pharmaceutical compositions comprise the combination of dsRNA molecules as detailed in the sequences given in Table 7. In one preferred embodiment the inventive pharmaceutical compositions comprise combinations of dsRNA pairs selected from the group consisting of SEQ ID NOs: 322/486 and 333/497, 322/486 and 346/510, 322/486 and 330/494, and, 322/486 and 324/488.

The pharmaceutical compositions described above may also comprise (a) pharmaceutically acceptable carrier(s), diluent(s) and/or excipient(s).

In another embodiment, the invention provides methods for treating, preventing or managing chronic liver diseases/disorders, inflammations, fibrotic conditions and/or proliferative disorders like cancers which are associated with Hepatitis B Virus, said method comprising administering to a subject in need of such treatment, prevention or management a therapeutically or prophylactically effective amount of one or more of the dsRNAs of the invention. Preferably, said subject is a mammal, most preferably a human patient.

In one embodiment, the invention provides a method for treating a subject having a pathological condition mediated by the infection of a Hepatitis B Virus. Such conditions comprise disorders associated with chronic liver diseases/disorders, inflammations, fibrotic conditions and/or proliferative disorders like cancers, as described above. In this embodiment, the dsRNA acts as a therapeutic agent for controlling the expression of a Hepatitis B Virus gene. The method comprises administering a pharmaceutical composition of the invention to the patient (e.g., human), such that expression of a Hepatitis B Virus gene is silenced. Because of their high specificity, the dsRNAs of the invention specifically target mRNAs of a Hepatitis B Virus gene. In one preferred embodiment the described dsRNAs specifically decrease Hepatitis B Virus mRNA levels and do not directly affect the expression and/or mRNA levels of off-target genes in the cell.

In one preferred embodiment the described dsRNA decrease Hepatitis B Virus mRNA levels in the liver by at least 60%, preferably by at least 70%, most preferably by at least 80% in vivo. in another embodiment the described dsRNAs decrease Hepatitis B Virus mRNA levels in vivo for at least 4 days. In another preferred embodiment, the dsRNAs of the invention are used for the preparation of a pharmaceutical composition for the treatment of chronic liver diseases/disorders, inflammations, fibrotic conditions and proliferative disorders like cancers. Such diseases to be treated with said pharmaceutical composition comprise but are not limited to: chronic hepatitis (CH), hepatic cirrhosis (HC) and hepatocellular carcinoma (HCC).

In another embodiment, the invention provides vectors for inhibiting the expression of a Hepatitis B Virus gene in a cell, in particular a Hepatitis B Virus gene comprising a regulatory sequence operably linked to a nucleotide sequence that encodes at least one strand of the dsRNA molecules of the invention.

In another embodiment, the invention provides a cell comprising a vector for inhibiting the expression of a Hepatitis B Virus gene in a cell. Said vector comprises a regulatory sequence operably linked to a nucleotide sequence that encodes at least one strand of the dsRNA molecule of the invention. Yet, it is preferred that said vector comprises, besides said regulatory sequence a sequence that encodes at least one "sense strand" of the inventive dsRNA and at least one "antisense strand" of said dsRNA. It is also envisaged that the claimed cell comprises two or more vectors comprising, besides said regulatory sequences, the herein defined sequence(s) that encode(s) at least one strand of the dsRNA molecules of the invention.

In one embodiment, the method comprises administering a composition comprising a dsRNA, wherein the dsRNA comprises a nucleotide sequence which is complementary to at least a part of an RNA transcript of a Hepatitis B Virus gene of the mammal to be treated. As pointed out above, also vectors and cells comprising nucleic acid molecules that encode for at least one strand of the herein defined dsRNA molecules can be used as pharmaceutical compositions and may, therefore, also be employed in the herein disclosed methods of treating a subject in need of medical intervention. It is also of note that these embodiments relating to pharmaceutical compositions and to corresponding methods of treating a (human) subject also relate to approaches like gene therapy approaches.

Hepatitis B Virus specific dsRNA molecules as provided herein or nucleic acid molecules encoding individual strands of these inventive dsRNA molecules may also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. *Proc. Natl. Acad. Sci.* USA (1994) 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In another aspect of the invention, Hepatitis B Virus specific dsRNA molecules that modulate Hepatitis B Virus gene expression activity are expressed from transcription units inserted into DNA or RNA vectors (see, e.g., Skillern A et al., International PCT Publication No. WO 00/22113). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., *Proc. Natl. Acad. Sci.* USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka et al., *Curr. Topics Micro. Immunol.* (1992) 158:97-129); adenovirus (see, for example, Berkner et al., *BioTechniques* (1998) 6:616; Rosenfeld et al. *Science* (1991) 252:431-434; and Rosenfeld et al. *Cell* (1992) 68:143-155); or alphavirus as well as others known in the art. Retroviruses have been used to introduce a variety of genes into many different cell types, including epithelial cells, in vitro and/or in vivo (see, e.g., Danos and Mulligan, *Proc. Natl. Acad. Sci.* USA (1998) 85:6460-6464). Recombinant retroviral vectors capable of transducing and expressing genes inserted into the genome of a cell can be produced by transfecting the recombinant retroviral genome into suitable packaging cell lines such as PA317 and Psi-CRIP (Comette et al., *Human Gene Therapy* (1991) 2:5-10; Cone et al., *Proc. Natl. Acad. Sci.* USA (1984) 81:6349). Recombinant adenoviral vectors can be used to infect a wide variety of cells and tissues in susceptible hosts (e.g., rat, hamster, dog, and chimpanzee) (Hsu et al., *J. Infectious Disease*, (1992) 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., *Proc. Natl. Acad. Sci.* USA (1986) 83:2511-2515).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., *FASEB J.* (1994) 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Hepatitis B Virus gene or multiple Hepatitis B Virus genes over a period of a week or more are also contemplated by the invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The following detailed description discloses how to make and use the dsRNA and compositions containing dsRNA to inhibit the expression of a target Hepatitis B Virus gene, as well as compositions and methods for treating diseases and disorders caused by the infection of said Hepatitis B Virus.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A", "U" and "T" or "dT" respectively, each generally stand for a nucleotide that contains guanine, cytosine, adenine, uracil and deoxythymidine as a base, respectively. However, the term "ribonucleotide" or "nucleotide" can also refer to a modified nucleotide, as further detailed below, or a surrogate replacement moiety. Sequences comprising such replacement moieties are embodiments of the invention. As detailed below, the herein described dsRNA molecules may also comprise "overhangs", i.e. unpaired, overhanging nucleotides which are not directly involved in the RNA double helical structure normally formed by the herein defined pair of "sense strand" and "antisense strand". Often, such an overhanging stretch comprises the deoxythymidine nucleotide, in most embodiments, two deoxythymidines in the 3' end. Such overhangs will be described and illustrated below.

The term "Hepatitis B Virus gene" as used herein relates to the genes necessary for replication and pathogenesis of Hepatitis B Virus, in particular to the genes that encode core protein, viral polymerase, surface antigen, e-antigen and the X protein and the genes that encode the functional fragments of the same. The term "Hepatitis B Virus gene/sequence" does not only relate to (the) wild-type sequence(s) but also to mutations and alterations which may be comprised in said gene/sequence. Accordingly, the present invention is not limited to the specific dsRNA molecules provided herein. The invention also relates to dsRNA molecules that comprise an antisense strand that is at least 85% complementary to the corresponding nucleotide stretch of an RNA transcript of a Hepatitis B Virus gene that comprises such mutations/alterations.

As used herein, the term "consensus sequence" refers to at least 13 contiguous nucleotides, preferably at least 17 contiguous nucleotides, most preferably at least 19 contiguous nucleotides, which is highly conserved among the Hepatitis B Virus genomic sequences of genotype A, B, C and D.

As used herein, "target sequence" refers to a contiguous portion of the nucleotide sequence of an mRNA molecule formed during the transcription of a Hepatitis B Virus gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature. However, as detailed herein, such a "strand comprising a sequence" may also comprise modifications, like modified nucleotides.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence. "Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

Sequences referred to as "fully complementary" comprise base-pairing of the oligonucleotide or polynucleotide comprising the first nucleotide sequence to the oligonucleotide or polynucleotide comprising the second nucleotide sequence over the entire length of the first and second nucleotide sequence.

However, where a first sequence is referred to as "substantially complementary" with respect to a second sequence herein, the two sequences can be fully complementary, or they may form one or more, but preferably not more than 13 mismatched base pairs upon hybridization.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

The term "double-stranded RNA", "dsRNA molecule", or "dsRNA", as used herein, refers to a ribonucleic acid molecule, or complex of ribonucleic acid molecules, having a duplex structure comprising two anti-parallel and substantially complementary nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. In addition to the duplex structure, a dsRNA may comprise one or more nucleotide overhangs. The nucleotides in said "overhangs" may comprise between 0 and 5 nucleotides, whereby "0" means no additional nucleotide(s) that form(s) an "overhang" and whereas "5" means five additional nucleotides on the individual strands of the dsRNA duplex. These optional "overhangs" are located in the 3' end of the individual strands. As will be detailed below, also dsRNA molecules which comprise only an "overhang" in one of the two strands may be useful and even advantageous in context of this invention. The "overhang" comprises preferably between 0 and 2 nucleotides. Most preferably two "dT" (deoxythymidine) nucleotides are found at the 3' end of both strands of the dsRNA. Also two "U" (uracil) nucleotides can be used as overhangs at the 3' end of both strands of the dsRNA. Accordingly, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. For example the antisense strand comprises 23 nucleotides and the sense strand comprises 21 nucleotides, forming a two nucleotide overhang at the 3' end of the antisense strand. Preferably, the two nucleotide overhang is fully complementary to the mRNA of the target gene. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence. Where the region of complementarity is not fully complementary to the target sequence, the mismatches are most tolerated outside nucleotides 2-7 of the 5' terminus of the antisense strand The term "sense strand," as used herein, refers to the strand of a dsRNA that includes a region that is substantially complementary to a region of the antisense strand. "Substantially complementary" means preferably at least 85% of the overlapping nucleotides in sense and antisense strand are complementary.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. It is, for example envisaged that the dsRNA molecules of this invention be administered to a subject in need of medical intervention. Such an administration may comprise the injection of the dsRNA, the vector or a cell of this invention into a diseased site in said subject, for example into liver tissue/cells or into cancerous tissues/cells, like liver cancer tissue. In addition, the injection is preferably in close proximity to the diseased tissue envisaged. In vitro introduction into a cell includes methods known in the art such as electroporation and lipofection.

As used herein, "chronic liver diseases/disorders" refers to the functional abnormality of liver lasting more than six months which can be caused by the infection of virus. One example of the chronic liver diseases/disorders is chronic hepatitis (CH).

The term "inflammation" as used herein refers to the biologic response of body tissue to injury, irritation, or disease which can be caused by harmful stimuli, for example, pathogens, damaged cells, or irritants. Inflammation is typically characterized by pain and swelling. Inflammation is intended to encompass both acute responses, in which inflammatory processes are active (e.g., neutrophils and leukocytes), and chronic responses, which are marked by slow progress, a shift in the type of cell present at the site of inflammation, and the formation of connective tissue. One example of an inflammation-caused disease is fibrosis.

The term "fibrotic conditions" as used herein refers to the functional problem of organs which can be caused by growth of fibrous tissue. One such example of such kind of disease is hepatic cirrhosis (HC).

The term "proliferating" and "proliferation" as used herein refer to cells undergoing mitosis. Throughout this application, the term "proliferative disorder" refers to any disease/disorder marked by unwanted or aberrant proliferation of tissue. As used herein, the term "proliferative disorder" also refers to conditions in which the unregulated and/or abnormal growth of cells can lead to the development of an unwanted condition or disease, which can be cancerous or non-cancerous.

Cancers to be treated comprise, but are again not limited to liver cancer, whereby said liver cancer may, inter alia, be selected from the group consisting of hepatocellular carcinoma (HCC), hepatoblastoma, a mixed liver cancer, a cancer derived from mesenchymal tissue, a liver sarcoma or a cholangiocarcinoma.

The terms "silence", "inhibit the expression of" and "knock down", in as far as they refer to a Hepatitis B Virus gene, herein refer to the at least partial suppression of the expression of a Hepatitis B Virus gene, as manifested by a reduction of the amount of mRNA transcribed from a Hepatitis B Virus gene which may be isolated from a first cell or group of cells in which a Hepatitis B Virus gene is transcribed and which has or have been treated such that the expression of a Hepatitis B Virus gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \times 100\%$$

Alternatively, the degree of inhibition may be given in terms of a reduction of a parameter that is functionally linked to the Hepatitis B Virus gene transcription, e.g. the amount of protein encoded by a Hepatitis B Virus gene which is secreted by a cell, or the number of cells displaying a certain phenotype.

As illustrated in the appended examples and in the appended Tables provided herein, the inventive dsRNA molecules are capable of inhibiting the expression of a Hepatitis B Virus by at least about 60%, preferably by at least 70%, most preferably by at least 80% in in vitro assays, i.e. in vitro. The term "in vitro" as used herein includes but is not limited to cell culture assays. The person skilled in the art can readily determine such an inhibition rate and related effects, in particular in light of the assays provided herein.

The term "off target" as used herein refers to all non-target mRNAs of the transcriptome that are predicted by in silico methods to hybridize to the described dsRNAs based on sequence complementarity. The dsRNAs of the present invention preferably do specifically inhibit the expression of Hepatitis B Virus gene, i.e. do not inhibit the expression of any off-target.

The term "half-life" as used herein is a measure of stability of a compound or molecule and can be assessed by methods known to a person skilled in the art, especially in light of the assays provided herein.

The term "non-immunostimulatory" as used herein refers to the absence of any induction of an immune response by the invented dsRNA molecules. Methods to determine immune responses are well known to a person skilled in the art, for example by assessing the release of cytokines, as described in the examples section.

The terms "treat", "treatment", and the like, mean in context of this invention the relief from or alleviation of a disorder related to Hepatitis B Virus infection, like chronic liver diseases/disorders, inflammations, fibrotic conditions and proliferative disorders, like cancers.

As used herein, a "pharmaceutical composition" comprises a pharmacologically effective amount of at least one kind of dsRNAs and a pharmaceutically acceptable carrier. However, such a "pharmaceutical composition" may also comprise individual strands of such dsRNA molecules or the herein described vector(s) comprising a regulatory sequence operably linked to a nucleotide sequence that encodes at least one strand of a sense or an antisense strand comprised in the dsRNAs of this invention. It is also envisaged that cells, tissues or isolated organs that express or comprise the herein defined dsRNAs may be used as "pharmaceutical compositions". As used herein, "pharmacologically effective amount," "therapeutically effective amount," or simply "effective amount" refers to that amount of an RNA effective to produce the intended pharmacological, therapeutic or preventive result.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives as known to persons skilled in the art.

It is in particular envisaged that the pharmaceutically acceptable carrier allows for the systemic administration of the dsRNAs, vectors or cells of this invention. Whereas also the enteric administration is envisaged the parenteral administration and also transdermal or transmucosal (e.g. insufflation, buccal, vaginal, anal) administration as well as inhalation of the drug are feasible ways of administering to a patient in need of medical intervention the compounds of this invention. When parenteral administration is employed, this can comprise the direct injection of the compounds of this invention into the diseased tissue or at least in close proximity. However, also intravenous, intraarterial, subcutaneous, intramuscular, intraperitoneal, intradermal, intrathecal and other administrations of the compounds of this invention are within the skill of the artisan, for example the attending physician.

For intramuscular, subcutaneous and intravenous use, the pharmaceutical compositions of the invention will generally be provided in sterile aqueous solutions or suspensions, buffered to an appropriate pH and isotonicity. In a preferred embodiment, the carrier consists exclusively of an aqueous buffer. In this context, "exclusively" means no auxiliary agents or encapsulating substances are present which might affect or mediate uptake of dsRNA in the cells that express a Hepatitis B Virus gene. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions and bi-specific antibodies can also be used as pharmaceutically acceptable carriers. These can be prepared according to methods known to those skilled in the art, for example, as described in PCT publication WO91/06309 and WO2011/003780 which is incorporated by reference herein.

As used herein, a "transformed cell" is a cell into which at least one vector has been introduced from which a dsRNA molecule or at least one strand of such a dsRNA molecule may be expressed. Such a vector is preferably a vector comprising a regulatory sequence operably linked to nucleotide sequence that encodes at least one sense strand or antisense strand of a dsRNA of the present invention.

It can be reasonably expected that shorter dsRNAs comprising one of the sequences in Table 1 and 4 minus only a few nucleotides on one or both ends may be similarly effective as compared to the dsRNAs described above.

In one preferred embodiment the inventive dsRNA molecules comprise nucleotides 1-19 of the sequences given in Table 1.

As pointed out above, in most embodiments of this invention, the dsRNA molecules provided herein comprise a duplex length (i.e. without "overhangs") of about 16 to about 30 nucleotides. Particular useful dsRNA duplex lengths are about 19 to about 25 nucleotides. Most preferred are duplex structures with a length of 19 nucleotides. In the inventive dsRNA molecules, the antisense strand is at least partially complementary to the sense strand.

The dsRNA of the invention can contain one or more mismatches to the target sequence. In a preferred embodiment, the dsRNA of the invention contains no more than 13 mismatches. If the antisense strand of the dsRNA contains mismatches to a target sequence, it is preferable that the area of mismatch not be located within nucleotides 2-7 of the 5' terminus of the antisense strand. In another embodiment it is preferable that the area of mismatch not be located within nucleotides 2-9 of the 5' terminus of the antisense strand.

As mentioned above, at least one end/strand of the dsRNA may have a single-stranded nucleotide overhang of 1 to 5, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in viva, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

The dsRNA of the present invention may also be chemically modified to enhance stability. The nucleic acids of the invention may be synthesized and/or modified by methods well established in the art. Chemical modifications may include, but are not limited to 2' modifications, introduction of non-natural bases, covalent attachment to a ligand, and replacement of phosphate linkages with thiophosphate linkages, inverted deoxythymidines. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl) cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams D J and Hall K B, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1,3-propandiol) and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, for example certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:111.6-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose the 4'-carbon of ribose. Introduction of a locked nucleotide into an oligonucleotide improves the affinity for complementary sequences and increases the melting temperature by several degrees.

Modifications of dsRNA molecules provided herein may positively influence their stability in vivo as well as in vitro and also improve their delivery to the (diseased) target side. Furthermore, such structural and chemical modifications may positively influence physiological reactions towards the dsRNA molecules upon administration, e.g. the cytokine release which is preferably suppressed. Such chemical and structural modifications are known in the art and are, inter alia, illustrated in Nawrot *Current Topics in Med Chem*, (2006) 6:913-925.

Conjugating a ligand to a dsRNA can enhance its cellular absorption as well as targeting to a particular tissue. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs (See Manoharan M, *Antisense & Nucleic Acid Drug Development* (2002) 12:103). Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Attachment of folic acid to the 3'-terminus of an oligonucleotide results in increased cellular uptake of the oligonucleotide (Li S, Deshmukh H M, and Huang L, *Pharm. Res.* (1998) 15:1540). Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See Manoharan M, *Antisense & Nucleic Acid Drug Development* (2002) 12:103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, a dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. No. 5,218,105, drawn to polyamine conjugated oligonucleotides; U.S. Pat. No. 5,541,307, drawn to oligonucleotides having modified backbones; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. No. 5,587,361 drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,608,046, both drawn to conjugated 4'-desmethyl nucleoside analogs; U.S. Pat. No. 5,610,289, drawn to backbone-modified oligonucleotide analogs; U.S. Pat. No. 6,262,241 drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable oligonucleotide synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to commercially available phosphoramidites.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-β-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxynucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Protecting groups in general and hydroxyl protecting groups in particular are well known in the art (Greene and Wuts, *Protective Groups in Organic Synthesis*, Chapter 2, 2d ed., John Wiley & Sons, New York, 1991). Amino-protecting groups stable to acid treatment are selectively removed with base treatment, and are used to make reactive amino groups selectively available for substitution. Examples of such groups are the Fmoc and various substituted sulfonylethyl carbamates exemplified by the Nsc group.

Additional amino-protecting groups include, but are not limited to, carbamate protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenyl-methyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support, well known in the art, allows for the preparation of oligonucleotides having unusual or modified nucleotides located at the 3-terminus of the oligonucleotide. In addition, it has been reported that the oligonucleotide can be cleaved from the universal support under milder reaction conditions when the oligonucleotide is bonded to the solid support via a syn-1,2-acetoxyphosphate group which more readily undergoes basic hydrolysis. See Guzaev A I, and Manoharan M J. *Am. Chem. Soc.* (2003) 125:2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 4,469,863, 5,023,243, 5,264,423, 5,321,131, 5,399,676, 5,405,939, 5,453,496, 5,455,33, and 5,466,677, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506, 5,214,134, 5,216,141, 5,264,562, 5,466,677, 5,470,967, 5,489,677, 5,602,240, and 5,663,312, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Teaching of PNA compounds can be found for example in U.S. Pat. No. 5,539,082.

Some preferred embodiments of the invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, or otherwise known in the art or commercially available. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 5,134,066, 5,459,255, 5,552,540, 5,594,121, and 5,596,091 all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term ". . . sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)m, wherein m is 1 to about 10. Preferred among these polyethers are linear and cyclic polyethylene glycols (PEGs), and (PEG)-containing groups, such as crown ethers and, inter alia, those which are disclosed by Delgardo et. al. (*Critical Reviews in Therapeutic Drug Carrier Systems* (1992) 9:249). Further sugar modifications are disclosed by Cook (*Anti-fibrosis Drug Design*, (1991) 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-$NR_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, (1997) 62:3415-3420). 2'-NR nucleosides are disclosed by Thomson J B, *J. Org. Chem.*, (1996) 61:6273-6281; and Polushin et al., *Tetrahedron Lett.*, (1996) 37:3227-3230. Further representative 2'-substituent groups amenable to the invention include those having one of formula I or II:

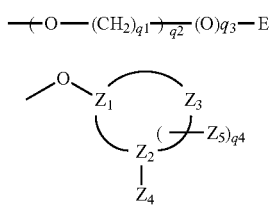

wherein

E is $C_1$-$C_{10}$ alkyl, N(Q3)(Q4) or N=C(Q3)(Q4); each Q3 and Q4 is, independently, H, $C_1$-$C_{10}$ alkyl, dialkylaminoalkyl, a nitrogen protecting group, a tethered or untethered conjugate group, a linker to a solid support; or Q3 and Q4, together, form a nitrogen protecting group or a ring structure optionally including at least one additional heteroatom selected from N and O;

q1 is an integer from 1 to 10;
q2 is an integer from 1 to 10;
q3 is 0 or 1;
q4 is 0, 1 or 2;

each Z1, Z2, and Z3 is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

Z4 is OM1, SM1, or N(M1)$_2$; each M1 is, independently, H, $C_1$-$C_8$ alkyl, $C_1$-$C_8$ haloalkyl, C(=NH)N(H)M2, C(=O)N(H)M2 or OC(=O)N(H)M2; M2 is H or $C_1$-$C_8$ alkyl; and Z5 is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, N(Q3)(Q4), OQ3, halo, SQ3 or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 5,359,044, 5,466,786, 5,519,134, 5,591,722, 5,597,909, 5,646,265, and 5,700,920, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci.* USA, (1989) 86:6553), cholic acid (Manoharan et al., *Bioorg. Med. Chem. Lett.*, (1994) 4:1053), a thioether, e.g., hexyl-S-tylthiol (Manoharan et al., *Ann, N.Y. Acad. Sci.*, (1992) 660:306; Manoharan et al., *Bioorg. Med. Chem. Let.*, (1993) 3:2765), a thiocholesterol (Oberhauser et al., *Nucl. Acids Res*, (1992) 20:533), an aliphatic chain, e.g., dodecandiol or undecyl residues (Saison-Behmoaras et al., *EMBO J.*, (1991) 10:111; Kabanov et al., *FEBS Lett.*, (1990) 259:327; Svinarchuk et al., *Biochimie*, (1993) 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, (1995) 36:3651; Shea et al., *Nucl. Acids Res.*, (1990) 18:3777), a polyamine or a polyethylene glycol chain (Manoharan et al., *Nucleosides & Nucleotides*, (1995) 14:969), or adamantane acetic acid (Manoharan et al., *Tetrahedron Lett.*, (1995) 36:3651), a palmityl moiety (Mishra et al., *Biochim. Biophys. Acta*, (1995) 1264:229), or an octadecylamine or hexylamino-carbonyl-oxycholesterol moiety (Crooke et al., *J. Pharmacol. Exp. Ther.*, (1996) 277:923).

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, (1989, 86:6553), cholic acid (Manoharan et al., *Bioorg. Med. Chem. Lett.*, (1994, 4:1053), a thioether, e.g., hexyl-S-tritylthiol (Manoharan et al., *Ann. N.Y. Acad. Sci.*, (1992, 660:306; Manoharan et al., Bioorg. Med. Chem. Let., (1993, 3:2765), a thiocholesterol (Oberhauser et al., *Nucl. Acids Res.*, (1992, 20:533), an aliphatic chain, e.g., dodecandiol or undecyl residues (Saison-Behmoaras et al., *EMBO J.*, (1991) 10:111; Kabanov et al., *FEBS Lett.*, (1990) 259:327; Svinarchuk et al., *Biochimie*, (1993) 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, (1995) 36:3651; Shea et al., *Nucl. Acids Res.*, (1990) 18:3777), a polyamine or a polyethylene glycol chain (Manoharan et al., *Nucleosides & Nucleotides*, (1995) 14:969), or adamantane acetic acid (Manoharan et al., *Tetrahedron Lett.*, (1995) 36:3651), a palmityl moiety (Mishra et al., *Biochim. Biophys. Acta*, (1995) 1264:229), or an octadecylamine or hexylamino-carbonyl-oxycholesterol moiety (Crooke et al., *J. Pharmacol. Exp. Ther.*, (1996) 277:923). Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphorylated.

Importantly, each of these approaches may be used for the synthesis of ligand conjugated oligonucleotides. Amino linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

The person skilled in the art is readily aware of methods to introduce the molecules of this invention into cells, tissues or organisms. Corresponding examples have also been provided in the detailed description of the invention above. For example, the nucleic acid molecules or the vectors of this invention, encoding for at least one strand of the inventive dsRNAs may be introduced into cells or tissues by methods known in the art, like transfections etc.

Also for the introduction of dsRNA molecules, means and methods have been provided. For example, targeted delivery by glycosylated and folate-modified molecules, including the use of polymeric carriers with ligands, such as galactose and lactose or the attachment of folic acid to various macromolecules allows the binding of molecules to be delivered to folate receptors. Targeted delivery by peptides and proteins other than antibodies, for example, including RGD-modified nanoparticles to deliver siRNA in vivo or multicomponent (nonviral) delivery systems including short cyclodextrins, adamantine-PEG are known. Yet, also the targeted delivery using antibodies or antibody fragments, including (monovalent) Fab-fragments of an antibody (or other fragments of such an antibody) or single-chain antibodies are envisaged. Injection approaches for target directed delivery comprise, inter alia, hydrodynamic i.v. injection. Also cholesterol conjugates of dsRNA may be used for targeted delivery, whereby the conjugation to lipohilic groups enhances cell uptake and improve pharmacokinetics and tissue biodistribution of oligonucleotides. Also cationic delivery systems are known, whereby synthetic vectors with net positive (cationic) charge to facilitate the complex formation with the polyanionic nucleic acid and interaction with the negatively charged cell membrane. Such cationic delivery systems comprise also cationic liposomal delivery systems, cationic polymer and peptide delivery systems. Other delivery systems for the cellular uptake of dsRNA/siRNA are aptamer-ds/siRNA. Also gene therapy approaches can be used to deliver the inventive dsRNA molecules or nucleic acid molecules encoding the same. Such systems comprise the use of non-pathogenic virus, modified viral vectors, as well as deliveries with nanoparticles or liposomes. Other delivery methods for the cellular uptake of dsRNA are extracorporeal, for example ex vivo treatments of cells, organs or tissues. Certain of these technologies are described and summarized in publications, like Akhtar, *Journal of Clinical Investigation* (2007) 117:3623-3632, Nguyen et al., *Current Opinion in Molecular Therapeutics* (2008) 10:158-167, Zamboni, *Clin Cancer Res* (2005) 11:8230-8234 or Ikeda et al., *Pharmaceutical Research* (2006) 23:1631-1640.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, and patents are incorporated by reference in their entirety. In case of conflict, the present specification, including definitions, will control. In addition, the materials, methods, and examples are illustrative only and not intended to be limiting.

The above provided embodiments and items of the present invention are now illustrated with the following, non-limiting examples.

EXAMPLES

Identification of dsRNAs for therapeutic use. dsRNA design was carried out to identify dsRNAs specifically targeting Hepatitis B Virus genotypes A, B, C and D for therapeutic use. First, the known Hepatitis B Virus genomic sequences were downloaded from NCBI Genbank (accessions listed in Table. 6). The genotype information was either extracted form NCBI Genbank files or determined by computer aided comparison with reference genomes (accessions listed in Table. 6).

The Hepatitis B Virus genomic sequences of genotype A-D were examined by computer analysis to identify optimal target regions for RNAi agents, namely highly conserved 17 nucleotide long sequence stretches that were identical in at least 90% of all sequences.

In identifying RNAi agents, the selection was limited to 17mer sequences having at least two mismatches to any sequence in the human RefSeq database (release 41), which we assumed to represent the comprehensive human transcriptome, by using a proprietary algorithm.

All 17mer sequences containing four or more consecutive G's (poly-G sequences) were further excluded from the synthesis.

Sequences of 19 nucleotides length were defined that harbor the selected 17mers in position 2 to 18.

These 19mer sequences yield RNA interference (RNAi) agents cross-reactive to Hepatitis B Virus genomic sequences of genotype A-D and formed the basis for the synthesis of the RNAi agents in appended Tables 1 and 2.

dsRNA synthesis. Oligoribonucleotides were synthesized according to the phosphoramidite technology on solid phase. Depending on the scale either an ABI 394 synthesizer (Applied Biosystems) or an AKTA oligopilot 100 (GE Healthcare, Freiburg, Germany) was used. Syntheses were performed on a solid support made of controlled pore glass (CPG, 520 Å, with a loading of 75 μmol/g, obtained from Prime Synthesis, Aston, Pa., USA). All 2'-modified RNA phosphoramidites as well as ancillary reagents were purchased from SAFC (Hamburg, Germany). Specifically, the following 2'-O-Methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O—dimethoxytrityl-$N^4$-(acetyl)-2'-O-methyl-cytidine-3'-O-(2-cyanoethyl-N,N-diisopropylamino) phosphoramidite, (5'-O-dimethoxytrityl-$N^2$-(isobutyryl)-2'-O-methyl-guanosine-3'-O-(2-cyanoethyl-N,N-diisopropylamino)phosphoramidite, and 5'-O-dimethoxy-trityl-2'-O-methyl-uridine-3'-O-(2-cyanoethyl-N,N-diisopropylamino) phosphoramidite. The 2'-Deoxy-2'-fluoro-phosphoramidites carried the same protecting groups as the 2'-O-methyl RNA amidites. All amidites were dissolved in anhydrous acetonitrile (100 mM) and molecular sieves (3 Å) were added. To generate the 5'-phosphate the 2-[2-(4,4'-Dimethoxytrityloxy)ethylsulfonyl]ethyl-(2-cyanoethyl)-(N,N-diisopropyl)-phosphoramidite from Glen Research (Sterling, Va., USA) was used. In order to introduce the C-6 aminolinker at the 5'-end of the oligomers the 6-(Trifluoroacetylamino)-hexyl-(2-cyanoethyl)-(N,N-diisopropyl)-phosphoramidite from Thermo Fisher Scientific (Milwaukee, Wis., USA) was employed. The 5'-modifications were introduced without any modification of the synthesis cycle. 5-Ethyl thiotetrazole (ETT, 500 mM in acetonitrile) was used as activator solution. Coupling times were 6 min. In order to introduce phosphorothioate linkages, a 50 mM solution of 3-((Dimethylamino-methylidene)amino)-3H-1,2,4-dithiazole-3-thione (DDTT, obtained from AM Chemicals, Oceanside, Calif., USA) in anhydrous Acetonitrile/pyridine (1:1 v/v) was employed.

Cleavage and deprotection of support bound oligomer. After finalization of the solid phase synthesis, cyanoethyl protecting groups were removed by a 30 min treatment with 20% Diethyl amine in ACN without cleaving the oligonucleotides from the support. Subsequently, the dried solid support was transferred to a 15 mL tube and treated with concentrated aqueous ammonia (Aldrich) for 18 h at 40° C. After centrifugation the supernatant was transferred to a new tube and the CPG was washed with aqueous ammonia. The combined solutions were evaporated and the solid residue was reconstituted in buffer A (see below).

Purification of oligoribonucleotides. Crude oligomers were purified by anionic exchange HPLC using a column packed with Source Q15 (GE Helthcare) and an AKTA Explorer system (GE Helthcare). Buffer A was 10 mM sodium perchlorate, 20 mM Tris, 1 mM EDTA, pH 7.4 (Fluka, Buchs, Switzerland) and contained 20% Acetonitrile and buffer B was the same as buffer A with the exception of 500 mM sodium perchlorate. A gradient of 22% B to 42% B within 32 column volumes (CV) was employed. UV traces at 280 nm were recorded Appropriate fractions were pooled and precipitated with 3M NaOAc, pH=5.2 and 70% Ethanol. Finally, the pellet was washed with 70% Ethanol. Alternatively, desalting was carried out using Sephadex HiTrap columns (GE Helthcare) according to the manufacturer's recommendation.

Annealing of oligoribonucleotides to generate siRNA. Complementary strands were mixed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 80° C. which was cooled to RT within 3 h.

In Vitro screening of HBV mRNA-targeting dsRNA. The psiCHECK™-2 vector (Promega) contains two reporter genes for monitoring RNAi activity: a synthetic version of the *renilla* luciferase (hRluc) gene and a synthetic firefly luciferase gene (hluc+). Measurement of firefly luciferase activity permits determination of changes unrelated to the RNAi activity of tested dsRNA. *Renilla* and firefly luciferase activities were measured using the Dual-Glo® Luciferase Assay System (Promega). HBV target sites of interest were inserted into the psiCHECK™-2 vector, after cloning into the multiple cloning region located 3' of the synthetic *renilla* luciferase gene's translational stop codon and the polyA tail. Cell line COS-7 was transfected with the vector, and subsequently treated with dsRNA-lipofectamine 2000 lipoplexes targeting the HBV sequences. The RNAi effect conferred by the dsRNA towards the cloned HBV target site was determined by measuring activity of the *renilla* luciferase fusion gene.

Generation of psiCHECK Vectors Containing Target Sequences. In order to test the activity of the HBV dsRNAs, a Dual-Luciferase HBV reporter was constructed. Regions 84 to 805, 1075 to 1992, 2165 to 2530, and 2718 to 2940 of Hepatitis B Virus genomic sequence accession number EU554538.1 (genotype C) were joined in silico. Two mutations were inserted intentionally (128 A→T, 598 T→C, positions relative to EU554538.1). One was needed to remove an internal XhoI site. The second mutation led to removal of a single mismatch to a dsRNA. This HBV target construct was extended by adding restriction sites at both the 5' and 3' end. The artificial DNA sequence was chemically synthesized by Geneart (Regensburg, Germany) and cloned into the XhoI/NotI site of psiCHECK™-2 Dual-Luciferase vector.

Transfection and Luciferase Quantification. Cos-7 cells (DSMZ. Braunschweig, Germany, cat. No. ACC-60) were seeded at a density of $2.25 \times 10^4$ cells/well in 96-well plates. Plasmid transfection was carried out at a concentration of 50 ng/well with 0.5 µL/well Lipofectamine 2000 (invitrogen GmbH, Karlsruhe, Germany, cat. No. 11668-019) as described by the manufacturer. 4 h after vector transfection, the medium was discarded and fresh medium was added. After this period, the dsRNAs were added to the cells in a concentration of 10 nM or 1 nM using Lipofectamine 2000 as described above. In order to optimize the HBV genotype coverage and to minimize development of resistance against dsRNAs, two different dsRNAs can be used simultaneously in combination. For demonstrating the feasibility of such approach, pairs of two different dsRNAs were selected among the most efficient dsRNAs with additional bias towards optimized genotype coverage.

The dsRNAs were added to the cells in a concentration of 5 nM or 0.5 nM for each dsRNA, resulting in 10 nM or 1 nM total dsRNA concentration, using Lipofectamine 2000 as described above. The cells were lysed 48 hours later using luciferase reagents as described by the manufacturer. *Renilla* luciferase protein levels were normalized to firefly luciferase levels to consider transfection efficiency. For each dsRNA four individual data points were collected. At least one dsRNA unrelated to all target sites was used as a control to determine the relative *renilla* luciferase protein levels in cells treated with dsRNA (Table 8). For comparison of silencing activity under full-match conditions, dsRNAs with full match to the *renilla* open reading frame were synthesized and tested in parallel to the HBV dsRNAs.

Inhibition data are given in appended Table 2.

Stability of dsRNAs. Stability of dsRNAs targeting human Hepatitis B Virus was determined in in vitro assays with any one of human, cynomolgous monkey or mouse serum by measuring the half-life of each single strand.

Measurements were carried out in triplicates for each time point, using 3 µL 50 µM dsRNA sample mixed with 30 µL human serum (Sigma), cynomolgous monkey serum (Sigma) or mouse serum (Sigma). Mixtures were incubated for either 0 min, 30 min, 1 h, 3 h, 6 h, 24 h, or 48 h at 37° C. As control for unspecific degradation dsRNA was incubated with 30 µL 1×PBS pH 6.8 for 48 h. Reactions were stopped by the addition of 4 µL proteinase K (20 mg/ml), 25 µL of "Tissue and Cell Lysis Solution" (Epicentre) and 38 µL Millipore water for 30 min at 65° C. Samples were afterwards spin filtered through a 0.2 µm 96 well filter plate at 1400 rpm for 8 min, washed with 55 µL Millipore water twice and spin filtered again.

For separation of single strands and analysis of remaining full length product (FLP), samples were run through an ion exchange Dionex Summit HPLC under denaturing conditions using as eluent A 20 mM $Na_3PO^4$ in 10% ACN pH=11 and for eluent B 1M NaBr in eluent A.

The following gradient was applied:

| Time (min) | % A | % B |
|---|---|---|
| -1.0 | 75 | 25 |
| 1.00 | 75 | 25 |
| 19.0 | 38 | 62 |
| 19.5 | 0 | 100 |
| 21.5 | 0 | 100 |
| 22.0 | 75 | 25 |
| 24.0 | 75 | 25 |

For every injection, the chromatograms were integrated automatically by the Dionex Chromeleon 6.60 HPLC software, and were adjusted manually if necessary. All peak areas were corrected to the internal standard (IS) peak and normalized to the incubation at t=0 min. The area under the peak and resulting remaining FLP was calculated for each single strand and triplicate separately. Half-life (t½) of a strand was defined by the average time point (h) for triplicates at which half of the FLP was degraded. Results are given in appended Table 3.

The invention claimed is:

1. A double-stranded ribonucleic acid molecule capable of inhibiting the expression of a Hepatitis B Virus gene in vitro wherein said double-stranded ribonucleic acid molecule comprises a sense strand comprising in order nucleotides 1-19 of SEQ ID 2, or 6 and an antisense strand at least partially complementary to the sense strand, wherein said sense strand and said antisense strand are each less than 30 nucleotides in length.

2. The double-stranded ribonucleic acid molecule of claim 1, wherein said antisense strand comprises in order nucleotides 1-19 of SEQ ID 158 or 163.

3. The double-stranded ribonucleic acid molecule of claim 2, wherein said double-stranded ribonucleic acid molecule comprises sequence pairs selected from the group consisting of SEQ ID NOs: 2/158 and 6/163.

4. The double-stranded ribonucleic acid molecule of claim 1, wherein the sense strand or the antisense strand further comprises a 3' overhang of 1-5 nucleotides in length.

5. The double-stranded ribonucleic acid molecule of claim 4, wherein the 3' overhang of the antisense strand comprises uracil or nucleotides which are complementary to the pregenomic RNA and/or the mRNA encoding the protein necessary for replication or pathogenesis of Hepatitis B Virus.

6. The double-stranded ribonucleic acid molecule of claim 4 wherein the 3' overhang of the sense strand comprises uracil or nucleotides which are identical to the pregenomic RNA and/or the mRNA encoding the protein necessary for replication or pathogenesis of Hepatitis B Virus.

7. The double-stranded ribonucleic acid molecule of claim 1, wherein said double-stranded ribonucleic acid molecule comprises at least one modified nucleotide selected from the group consisting of: 2'-O-methyl modified nucleotide, nucleotide comprising a 5'-phosphorothioate group, terminal nucleotide linked to a cholesteryl derivative, terminal nucleotide linked to a dodecanoic acid bisdecylamide group, 2'-deoxy- 2'-fluoro modified nucleotide, 2-deoxy-nucleotide, locked nucleotide, abasic nucleotide, deoxythymidine, inverted deoxythymidine, 2'-amino-modified nucleotide, 2'-alkyl-modified nucleotide, morpholino nucleotide, phosphoramidate, and non-natural base comprising nucleotide.

8. The double-stranded ribonucleic acid molecule of claim 7, wherein said double-stranded ribonucleic acid molecule contains a 2'-O-methyl modified nucleotide, a nucleotide comprising a 5'-phosphomthioate group, and a deoxythymidine.

9. The double-stranded ribonucleic acid molecule of claim 8, wherein said sense strand or said antisense strand comprises an overhang of 1-2 deoxythymidines.

10. The double-stranded ribonucleic acid molecule of claim 9, wherein said double-stranded ribonucleic acid molecule comprises the sequence pairs selected from the group consisting of SEQ ID NOs: 322/486 and 327/491.

11. The double-stranded ribonucleic acid molecule of claim 1 wherein said double-stranded ribonucleic acid molecule comprises a nucleic acid sequence encoding said sense strand or said antisense strand.

12. A pharmaceutical composition comprising:
   a) first and second double-stranded ribonucleic acid molecules each as defined in claim 1;
   b) at least one nucleic acid sequence encoding sense strands or antisense strands comprising first and second double-stranded ribonucleic acid molecules each as defined in claim 1; or,
   c) a cell, tissue or non-human organism comprising first and second double-stranded ribonucleic acid molecules each as defined in claim 1.

13. The pharmaceutical composition of claim 12 wherein:
   a) said first double stranded ribonucleic acid has a sense strand comprising in order nucleotides 1-19 of SEQ ID 2 and said second double-stranded ribonucleic acid has a sense strand comprising in order nucleotides 1-19 of SEQ ID 4 or 6 or
   b) said first double stranded ribonucleic acid has a sense strand comprising in order nucleotides 1-19 of SEQ ID 6 and said second double-stranded ribonucleic acid has a sense strand comprising in order nucleotides 1-19 of SEQ ID 2 or 7.

14. The pharmaceutical composition of claim 12 further comprising a pharmaceutically acceptable carrier, stabilizer and/or diluent.

15. A method for inhibiting the expression of Hepatitis B Virus gene in a cell, a tissue, or an organism comprising:
   a) introducing into the cell, tissue, or organism the double-stranded ribonucleic acid molecule as defined in claim 1; and
   b) maintaining the cell, tissue or organism produced in step a) for a time sufficient to obtain degradation of the mRNA transcript of a Hepatitis B Virus gene, thereby inhibiting expression of a Hepatitis B Virus gene in the cell.

16. The method of claim 15 wherein inhibiting expression of Hepatitis B Virus gene in an organism treats or manages a pathological condition or disease caused by infection with the Hepatitis B Virus.

17. The method claim 16 wherein the pathological condition and disease caused by the infection with the Hepatitis B Virus is selected from the group consisting of: chronic liver disorder, inflammation, fibrotic condition, and proliferative disorder.

* * * * *

```
                              SEQUENCE LISTING

<160> NUMBER OF SEQ ID NOS: 648

<210> SEQ ID NO 1
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 1
caagguaugu ugcccguuu                                                   19

<210> SEQ ID NO 2
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 2
cuguaggcau aaauuggua                                                   19

<210> SEQ ID NO 3
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 3
ucugcggcgu uuuaucaua                                                   19

<210> SEQ ID NO 4
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 4
```
accucugccu aaucaucuc                                              19

<210> SEQ ID NO 5
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 5
uuuacuagug ccauuugua                                              19

<210> SEQ ID NO 6
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 6
accucugccu aaucaucua                                              19

<210> SEQ ID NO 7
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 7
cuguaggcau aaauugguc                                              19

<210> SEQ ID NO 8
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 8
ugucugcggc guuuuauca                                              19

<210> SEQ ID NO 9
<211> LENGTH: 19
<212> TYPE: RNA
<213> ORGANISM: Artificial sequence -continued

```
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 9
uacuagugcc auuuguuca                                                      19

<210> SEQ ID NO 10
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 10
caacuuuuuc accucugca                                                      19

<210> SEQ ID NO 11
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 11
ccauuuguuc agugguucg                                                      19

<210> SEQ ID NO 12
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 12
ccaaguguuu gcugacgca                                                      19

<210> SEQ ID NO 13
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
``` group"

<400> SEQUENCE: 13
ccauuuguuc agugguuca                                                      19

<210> SEQ ID NO 14
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 14
uuuacuagug ccauuguu                                                       19

<210> SEQ ID NO 15
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 15
caccucugcc uaaucauca                                                      19

<210> SEQ ID NO 16
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 16
cuggcucagu uuacuagug                                                      19

<210> SEQ ID NO 17
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 17
caagguaugu ugcccguua                                                      19

```
<210> SEQ ID NO 18
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 18
cuggcucagu uuacuagua                                                19

<210> SEQ ID NO 19
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 19
gaggcuguag gcauaaauu                                                19

<210> SEQ ID NO 20
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 20
caguuuacua gugccauuu                                                19

<210> SEQ ID NO 21
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 21
agguauguug cccguuugu                                                19

<210> SEQ ID NO 22
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 22
uauguugccc guuugucca                                                   19

<210> SEQ ID NO 23
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 23
gaggcuguag gcauaaaua                                                   19

<210> SEQ ID NO 24
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 24
gucugcggcg uuuuaucau                                                   19

<210> SEQ ID NO 25
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 25
caacuuuuuc accucugcc                                                   19

<210> SEQ ID NO 26
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 26
```
ccgugugcac uucgcuuca                                                      19

<210> SEQ ID NO 27
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 27
ucaagguaug uugcccgua                                                      19

<210> SEQ ID NO 28
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 28
caguuuacua gugccauua                                                      19

<210> SEQ ID NO 29
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 29
ugguggacuu cucucaauu                                                      19

<210> SEQ ID NO 30
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 30
agguauguug cccguuuga                                                      19

<210> SEQ ID NO 31
<211> LENGTH: 19
<212> TYPE: RNA

```
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 31
cugcucgugu uacaggcgg                                                19

<210> SEQ ID NO 32
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 32
uauguugccc guuuguccu                                                19

<210> SEQ ID NO 33
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 33
ucaagguaug uugcccguu                                                19

<210> SEQ ID NO 34
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 34
ucuuaucaac acuuccgga                                                19

<210> SEQ ID NO 35
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
```

```
<223> OTHER INFORMATION: /mod_base = "nucleoside: lacks 5'-phosphate
      group"

<400> SEQUENCE: 35
caccucugcc uaaucaucu                                                    19

<210> SEQ ID NO 36
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 36
auaagaggac ucuuggacu                                                    19

<210> SEQ ID NO 37
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 37
gucugcggcg uuuuaucaa                                                    19

<210> SEQ ID NO 38
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 38
ggcgcugaau cccgcggac                                                    19

<210> SEQ ID NO 39
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 39
cgcgucgcag aagaucuca                                                    19
```

```
<210> SEQ ID NO 40
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 40
aaugucaacg accgaccuu                                                  19

<210> SEQ ID NO 41
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 41
gcucaguuua cuagugcca                                                  19

<210> SEQ ID NO 42
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 42
ugguggacuu cucucaaua                                                  19

<210> SEQ ID NO 43
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 43
aucgccgcgu cgcagaaga                                                  19

<210> SEQ ID NO 44
<211> LENGTH: 19
<212> TYPE: RNA
<213> ORGANISM: Artificial sequence
<220> FEATURE:
<223> OTHER INFORMATION: Description of the artificial sequence: sense
```

```
           strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 44
gccauuuguu cagugguuc                                                  19

<210> SEQ ID NO 45
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 45
cgauccauac ugcggaacu                                                  19

<210> SEQ ID NO 46
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 46
ucaccucugc cuaaucauc                                                  19

<210> SEQ ID NO 47
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 47
guggacuucu cucaauuuu                                                  19

<210> SEQ ID NO 48
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

```
<400> SEQUENCE: 48
gggucaccau auucuuggg                                                19

<210> SEQ ID NO 49
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 49
gccgcgucgc agaagaucu                                                19

<210> SEQ ID NO 50
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 50
ucaaucgccg cgucgcaga                                                19

<210> SEQ ID NO 51
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 51
uggauguguc ugcggcguu                                                19

<210> SEQ ID NO 52
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 52
uacuguucaa gccuccaag                                                19

<210> SEQ ID NO 53
<211> LENGTH: 19
```

```
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 53
guuuacuagu gccauuugu                                                  19

<210> SEQ ID NO 54
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 54
acuagugcca uuuguucag                                                  19

<210> SEQ ID NO 55
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 55
ccgcgucgca gaagaucuc                                                  19

<210> SEQ ID NO 56
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 56
uaucuuauca acacuuccg                                                  19

<210> SEQ ID NO 57
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
```

```
<222> LOCATION: 1
<223> OTHER INFORMATION: /mod_base = "nucleoside: lacks 5'-phosphate
      group"

<400> SEQUENCE: 57
ggccaaaauu cgcaguccc                                               19

<210> SEQ ID NO 58
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 58
uucaccucug ccuaaucau                                               19

<210> SEQ ID NO 59
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 59
cucaguuuac uagugccau                                               19

<210> SEQ ID NO 60
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 60
uguugcccgu uuguccucu                                               19

<210> SEQ ID NO 61
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 61
uagugccauu uguucagug                                               19
```

```
<210> SEQ ID NO 62
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 62
aggcuguagg cauaaauug                                                19

<210> SEQ ID NO 63
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 63
augugucugc ggcguuuua                                                19

<210> SEQ ID NO 64
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 64
acuucgcuuc accucugca                                                19

<210> SEQ ID NO 65
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 65
cgugugcacu ucgcuucac                                                19

<210> SEQ ID NO 66
<211> LENGTH: 19
<212> TYPE: RNA
<213> ORGANISM: Artificial sequence
<220> FEATURE:
```

```
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 66
gugguggacu ucucucaau                                                 19

<210> SEQ ID NO 67
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 67
ugugucugcg gcguuuuau                                                 19

<210> SEQ ID NO 68
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 68
aagguauguu gcccguuug                                                 19

<210> SEQ ID NO 69
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 69
ucaacgaccg accuugagg                                                 19

<210> SEQ ID NO 70
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

```
<400> SEQUENCE: 70
cauaagagga cucuuggac                                              19

<210> SEQ ID NO 71
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 71
gucaacgacc gaccuugag                                              19

<210> SEQ ID NO 72
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 72
auauucuugg gaacaagag                                              19

<210> SEQ ID NO 73
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 73
ugcucguguu acaggcggg                                              19

<210> SEQ ID NO 74
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 74
caaucgccgc gucgcagaa                                              19

<210> SEQ ID NO 75
```

```
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 75
acuguucaag ccuccaagc                                            19

<210> SEQ ID NO 76
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 76
cgccgcgucg cagaagauc                                            19

<210> SEQ ID NO 77
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 77
cauuuguuca gugguucgu                                            19

<210> SEQ ID NO 78
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 78
cgcugaaucc cgcggacga                                            19

<210> SEQ ID NO 79
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
```

-continued

```
<221> NAME/KEY: modified_base
<222> LOCATION: 1
<223> OTHER INFORMATION: /mod_base = "nucleoside: lacks 5'-phosphate
      group"

<400> SEQUENCE: 79
ugggucacca uauucuugg                                                     19

<210> SEQ ID NO 80
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 80
uccucugccg auccauacu                                                     19

<210> SEQ ID NO 81
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 81
augucaacga ccgaccuug                                                     19

<210> SEQ ID NO 82
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 82
ccucugccua aucaucuca                                                     19

<210> SEQ ID NO 83
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 83
```
accgugugca cuucgcuuc                                                19

<210> SEQ ID NO 84
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 84
ugccgaucca uacugcgga                                                19

<210> SEQ ID NO 85
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 85
cagagucuag acucguggu                                                19

<210> SEQ ID NO 86
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 86
cuguucaagc cuccaagcu                                                19

<210> SEQ ID NO 87
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 87
ggaggcugua ggcauaaau                                                19

<210> SEQ ID NO 88
<211> LENGTH: 19
<212> TYPE: RNA
<213> ORGANISM: Artificial sequence -continued

```
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 88
aggaggcugu aggcauaaa                                                   19

<210> SEQ ID NO 89
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 89
gguggacuuc ucucaauuu                                                   19

<210> SEQ ID NO 90
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 90
gcaacuuuuu caccucugc                                                   19

<210> SEQ ID NO 91
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 91
cugcucgugu uacaggcga                                                   19

<210> SEQ ID NO 92
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
```

-continued group"

<400> SEQUENCE: 92
cuagugccau uuguucagu                                        19

<210> SEQ ID NO 93
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 93
cugccgaucc auacugcgg                                        19

<210> SEQ ID NO 94
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 94
gugugcacuu cgcuucacc                                        19

<210> SEQ ID NO 95
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 95
gcucguguua caggcgggc                                        19

<210> SEQ ID NO 96
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 96
ccuaucuuau caacacuuc                                        19

```
<210> SEQ ID NO 97
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 97
ucucaaucgc cgcgucgca                                              19

<210> SEQ ID NO 98
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 98
gcccgucugu gccuucuca                                              19

<210> SEQ ID NO 99
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 99
cuaucuuauc aacacuucc                                              19

<210> SEQ ID NO 100
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 100
auguugcccg uuuguccuc                                              19

<210> SEQ ID NO 101
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 101
guauguugcc cguuugucc                                                    19

<210> SEQ ID NO 102
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 102
cuucgcuuca ccucugcac                                                    19

<210> SEQ ID NO 103
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 103
ugugcacuuc gcuucaccu                                                    19

<210> SEQ ID NO 104
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 104
gccaaaauuc gcagucccg                                                    19

<210> SEQ ID NO 105
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 105
```
ccugcucgug uuacaggcg                                                  19

<210> SEQ ID NO 106
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 106
uggagugugg auucgcacu                                                  19

<210> SEQ ID NO 107
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 107
aacgaccgac cuugaggca                                                  19

<210> SEQ ID NO 108
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 108
acagagucua gacucgugg                                                  19

<210> SEQ ID NO 109
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 109
aaucgccgcg ucgcagaag                                                  19

<210> SEQ ID NO 110
<211> LENGTH: 19
<212> TYPE: RNA

```
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 110
gguauguugc ccguuuguc                                                  19

<210> SEQ ID NO 111
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 111
gccgauccau acugcggaa                                                  19

<210> SEQ ID NO 112
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 112
gcccuaucuu aucaacacu                                                  19

<210> SEQ ID NO 113
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 113
aguuuacuag ugccauuug                                                  19

<210> SEQ ID NO 114
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
```

-continued

```
<223> OTHER INFORMATION: /mod_base = "nucleoside: lacks 5'-phosphate
      group"

<400> SEQUENCE: 114
ugucaacgac cgaccuuga                                                19

<210> SEQ ID NO 115
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 115
acuucucuca auuuucuag                                                19

<210> SEQ ID NO 116
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 116
gcgcgggacg uccuuuguc                                                19

<210> SEQ ID NO 117
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 117
ucuagacucg ugguggacu                                                19

<210> SEQ ID NO 118
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 118
gauccauacu gcggaacuc                                                19
```

```
<210> SEQ ID NO 119
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 119
cucugccgau ccauacugc                                              19

<210> SEQ ID NO 120
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 120
ucugccgauc cauacugcg                                              19

<210> SEQ ID NO 121
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 121
ccucugccga uccauacug                                              19

<210> SEQ ID NO 122
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 122
gcaccucucu uuacgcggu                                              19

<210> SEQ ID NO 123
<211> LENGTH: 19
<212> TYPE: RNA
<213> ORGANISM: Artificial sequence
<220> FEATURE:
<223> OTHER INFORMATION: Description of the artificial sequence: sense
``` strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 123
aagaacuccc ucgccucgc                                                19

<210> SEQ ID NO 124
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 124
gaacucccuc gccucgcag                                                19

<210> SEQ ID NO 125
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 125
ucucucaauu uucuagggc                                                19

<210> SEQ ID NO 126
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 126
gggcgcaccu cucuuuacg                                                19

<210> SEQ ID NO 127
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 127
ccgauccaua cugcggaac                                                    19

<210> SEQ ID NO 128
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 128
aacucccucg ccucgcaga                                                    19

<210> SEQ ID NO 129
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 129
cuccucugcc gauccauac                                                    19

<210> SEQ ID NO 130
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 130
ggagugugga uucgcacuc                                                    19

<210> SEQ ID NO 131
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 131
cgggcgcacc ucucuuuac                                                    19

<210> SEQ ID NO 132
<211> LENGTH: 19

-continued

```
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 132
gucucaaucg ccgcgucgc                                              19

<210> SEQ ID NO 133
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 133
auccauacug cggaacucc                                              19

<210> SEQ ID NO 134
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 134
cgcaccucuc uuuacgcgg                                              19

<210> SEQ ID NO 135
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 135
caacgaccga ccuugaggc                                              19

<210> SEQ ID NO 136
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
```

```
<222> LOCATION: 1
<223> OTHER INFORMATION: /mod_base = "nucleoside: lacks 5'-phosphate
      group"

<400> SEQUENCE: 136
ccauacugcg gaacuccua                                                   19

<210> SEQ ID NO 137
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 137 ugaauccgc ggacgaccc                                                    19

<210> SEQ ID NO 138
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 138
agaacucccu cgccucgca                                                   19

<210> SEQ ID NO 139
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 139
ggcgcaccuc ucuuuacgc                                                   19

<210> SEQ ID NO 140
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 140
gcgcaccucu cuuuacgcg                                                   19
```

```
<210> SEQ ID NO 141
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 141
gcugaauccc gcggacgac                                               19

<210> SEQ ID NO 142
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 142
cacuucgcuu caccucugc                                               19

<210> SEQ ID NO 143
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 143
cucaaucgcc gcgucgcag                                               19

<210> SEQ ID NO 144
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 144
ucccgucggc gcugaaucc                                               19

<210> SEQ ID NO 145
<211> LENGTH: 19
<212> TYPE: RNA
<213> ORGANISM: Artificial sequence
<220> FEATURE:
```

<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 145
cugaaucccg cggacgacc                                              19

<210> SEQ ID NO 146
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 146
agagucuaga cucguggug                                              19

<210> SEQ ID NO 147
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 147
uccauacugc ggaacuccu                                              19

<210> SEQ ID NO 148
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 148
gcgcugaauc ccgcggacg                                              19

<210> SEQ ID NO 149
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 149
aguguggauu cgcacuccu					19

<210> SEQ ID NO 150
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 150
cccugcucgu guuacaggc					19

<210> SEQ ID NO 151
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 151
gaaucccgcg gacgacccg					19

<210> SEQ ID NO 152
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 152
aagcugugcc uugggguggc					19

<210> SEQ ID NO 153
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 153
gcccugcucg uguuacagg					19

<210> SEQ ID NO 154

```
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 154
gucccgucgg cgcugaauc                                               19

<210> SEQ ID NO 155
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 155
aucuuaucaa cacuuccgg                                               19

<210> SEQ ID NO 156
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 156
cuuaucaaca cuuccggaa                                               19

<210> SEQ ID NO 157
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 157
aaacgggcaa cauaccuug                                               19

<210> SEQ ID NO 158
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
```

```
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 158
taccaauuua ugccuacag                                              19

<210> SEQ ID NO 159
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 159
uaugauaaaa cgccgcaga                                              19

<210> SEQ ID NO 160
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 160
taugauaaaa cgccgcaga                                              19

<210> SEQ ID NO 161
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 161
gagaugauua ggcagaggu                                              19

<210> SEQ ID NO 162
<211> LENGTH: 19
<212> TYPE: DNA
<213> ORGANISM: Artificial sequence
<220> FEATURE:
```

-continued

```
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 162
tacaaauggc acuaguaaa                                                19

<210> SEQ ID NO 163
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 163
tagaugauua ggcagaggu                                                19

<210> SEQ ID NO 164
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 164
gaccaauuua ugccuacag                                                19

<210> SEQ ID NO 165
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 165
ugauaaaacg ccgcagaca                                                19

<210> SEQ ID NO 166
<211> LENGTH: 19
```

```
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 166
tgauaaaacg ccgcagaca                                              19

<210> SEQ ID NO 167
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 167
ugaacaaaug gcacuagua                                              19

<210> SEQ ID NO 168
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 168
tgaacaaaug gcacuagua                                              19

<210> SEQ ID NO 169
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"
```

<400> SEQUENCE: 169
tgcagaggug aaaaaguug                                                    19

<210> SEQ ID NO 170
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 170
cgaaccacug aacaaaugg                                                    19

<210> SEQ ID NO 171
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 171
ugcgucagca aacacuugg                                                    19

<210> SEQ ID NO 172
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 172
tgcgucagca aacacuugg                                                    19

<210> SEQ ID NO 173
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base

```
<222> LOCATION: 2..19
<223> OTHER INFORMATION: /mod_base = "2'-hydroxy corresponding
      nucleoside"

<400> SEQUENCE: 173
tgaaccacug aacaaaugg                                                  19

<210> SEQ ID NO 174
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 174
aacaaauggc acuaguaaa                                                  19

<210> SEQ ID NO 175
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 175
tgaugauuag gcagaggug                                                  19

<210> SEQ ID NO 176
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 176
cacuaguaaa cugagccag                                                  19

<210> SEQ ID NO 177
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
```

```
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 177
taacgggcaa cauaccuug                                                    19

<210> SEQ ID NO 178
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 178
tacuaguaaa cugagccag                                                    19

<210> SEQ ID NO 179
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 179
aauuuaugcc uacagccuc                                                    19

<210> SEQ ID NO 180
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 180
aaauggcacu aguaaacug                                                    19

<210> SEQ ID NO 181
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
```

```
<221> NAME/KEY: modified_base
<222> LOCATION: 1
<223> OTHER INFORMATION: /mod_base = "nucleoside: lacks 5'-phosphate
      group"

<400> SEQUENCE: 181
acaaacgggc aacauaccu                                                      19

<210> SEQ ID NO 182
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 182
uggacaaacg ggcaacaua                                                      19

<210> SEQ ID NO 183
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 183
tauuuaugcc uacagccuc                                                      19

<210> SEQ ID NO 184
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 184
augauaaaac gccgcagac                                                      19

<210> SEQ ID NO 185
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
```

```
<223> OTHER INFORMATION: /mod_base = "nucleoside: lacks 5'-phosphate
      group"

<400> SEQUENCE: 185
ggcagaggug aaaaaguug                                                    19

<210> SEQ ID NO 186
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 186
ugaagcgaag ugcacacgg                                                    19

<210> SEQ ID NO 187
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 187
tgaagcgaag ugcacacgg                                                    19

<210> SEQ ID NO 188
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 188
tacgggcaac auaccuuga                                                    19

<210> SEQ ID NO 189
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 189
taauggcacu aguaaacug                                                    19

<210> SEQ ID NO 190
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 190
aauugagaga aguccacca                                                    19

<210> SEQ ID NO 191
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 191
tcaaacgggc aacauaccu                                                    19

<210> SEQ ID NO 192
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 192
ccgccuguaa cacgagcag                                                    19

<210> SEQ ID NO 193
<211> LENGTH: 19
<212> TYPE: RNA
<213> ORGANISM: Artificial sequence
```

```
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 193
aggacaaacg ggcaacaua                                                19

<210> SEQ ID NO 194
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 194
aacgggcaac auaccuuga                                                19

<210> SEQ ID NO 195
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 195
uccggaagug uugauaaga                                                19

<210> SEQ ID NO 196
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 196
tccggaagug uugauaaga                                                19

<210> SEQ ID NO 197
<211> LENGTH: 19
<212> TYPE: RNA
<213> ORGANISM: Artificial sequence
<220> FEATURE:
<223> OTHER INFORMATION: Description of the artificial sequence:
```

```
    antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 197
agaugauuag gcagaggug                                                    19

<210> SEQ ID NO 198
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 198
aguccaagag uccucuuau                                                    19

<210> SEQ ID NO 199
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 199
tugauaaaac gccgcagac                                                    19

<210> SEQ ID NO 200
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 200
guccgcggga uucagcgcc                                                    19

<210> SEQ ID NO 201
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
```

```
<221> NAME/KEY: modified_base
<222> LOCATION: 1
<223> OTHER INFORMATION: /mod_base = "nucleoside: lacks 5'-phosphate
      group"

<400> SEQUENCE: 201
ugagaucuuc ugcgacgcg                                                   19

<210> SEQ ID NO 202
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 202
aaggucgguc guugacauu                                                   19

<210> SEQ ID NO 203
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 203
uggcacuagu aaacugagc                                                   19

<210> SEQ ID NO 204
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 204
tauugagaga aguccacca                                                   19

<210> SEQ ID NO 205
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
```

```
<223> OTHER INFORMATION: /mod_base = "nucleoside: lacks 5'-phosphate
      group"

<400> SEQUENCE: 205
ucuucugcga cgcggcgau                                                  19

<210> SEQ ID NO 206
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 206
gaaccacuga acaaauggc                                                  19

<210> SEQ ID NO 207
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 207
aguuccgcag uauggaucg                                                  19

<210> SEQ ID NO 208
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 208
gaugauuagg cagagguga                                                  19

<210> SEQ ID NO 209
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 209
aaaauugaga gaaguccac                                                  19
```

```
<210> SEQ ID NO 210
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 210
cccaagaaua uggugaccc                                                   19

<210> SEQ ID NO 211
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 211
agaucuucug cgacgcggc                                                   19

<210> SEQ ID NO 212
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 212
ucugcgacgc ggcgauuga                                                   19

<210> SEQ ID NO 213
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 213
aacgccgcag acacaucca                                                   19

<210> SEQ ID NO 214
<211> LENGTH: 19
<212> TYPE: RNA
<213> ORGANISM: Artificial sequence
<220> FEATURE:
<223> OTHER INFORMATION: Description of the artificial sequence:
```

```
            antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 214
cuuggaggcu ugaacagua                                                    19

<210> SEQ ID NO 215
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 215
acaaauggca cuaguaaac                                                    19

<210> SEQ ID NO 216
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 216
cugaacaaau ggcacuagu                                                    19

<210> SEQ ID NO 217
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 217
gagaucuucu gcgacgcgg                                                    19

<210> SEQ ID NO 218
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

-continued

<400> SEQUENCE: 218
cggaaguguu gauaagaua                        19

<210> SEQ ID NO 219
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 219
gggacugcga auuuuggcc                        19

<210> SEQ ID NO 220
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 220
augauuaggc agaggugaa                        19

<210> SEQ ID NO 221
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 221
auggcacuag uaaacugag                        19

<210> SEQ ID NO 222
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 222
agaggacaaa cgggcaaca                        19

<210> SEQ ID NO 223
<211> LENGTH: 19

```
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 223
cacugaacaa auggcacua                                                 19

<210> SEQ ID NO 224
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 224
caauuuaugc cuacagccu                                                 19

<210> SEQ ID NO 225
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 225
uaaaacgccg cagacacau                                                 19

<210> SEQ ID NO 226
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 226
taaaacgccg cagacacau                                                 19

<210> SEQ ID NO 227
<211> LENGTH: 19
<212> TYPE: RNA
<213> ORGANISM: Artificial sequence
```

```
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 227
ugcagaggug aagcgaagu                                                    19

<210> SEQ ID NO 228
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 228
gugaagcgaa gugcacacg                                                    19

<210> SEQ ID NO 229
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 229
auugagagaa guccaccac                                                    19

<210> SEQ ID NO 230
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 230
auaaaacgcc gcagacaca                                                    19

<210> SEQ ID NO 231
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
``` group"

<400> SEQUENCE: 231
caaacgggca acauaccuu                                                19

<210> SEQ ID NO 232
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 232
ccucaagguc ggucguuga                                                19

<210> SEQ ID NO 233
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 233
guccaagagu ccucuuaug                                                19

<210> SEQ ID NO 234
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 234
cucaaggucg gucguugac                                                19

<210> SEQ ID NO 235
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 235
cucuuguucc caagaauau                                                19

```
<210> SEQ ID NO 236
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 236
cccgccugua acacgagca                                               19

<210> SEQ ID NO 237
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 237
uucugcgacg cggcgauug                                               19

<210> SEQ ID NO 238
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 238
gcuuggaggc uugaacagu                                               19

<210> SEQ ID NO 239
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 239
gaucuucugc gacgcggcg                                               19

<210> SEQ ID NO 240
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 240
acgaaccacu gaacaaaug                                                    19

<210> SEQ ID NO 241
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 241
ucguccgcgg gauucagcg                                                    19

<210> SEQ ID NO 242
<211> LENGTH: 19
<212> TYPE: RNA
<213> ORGANISM: Artificial sequence
<220> FEATURE:
<223> OTHER INFORMATION: Description of the artificial sequence
      : antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 242
ccaagaauau ggugaccca                                                    19

<210> SEQ ID NO 243
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 243
aguauggauc ggcagagga                                                    19

<210> SEQ ID NO 244
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 244
```
caaggucggu cguugacau					19

<210> SEQ ID NO 245
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 245
ugagaugauu aggcagagg					19

<210> SEQ ID NO 246
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 246
gaagcgaagu gcacacggu					19

<210> SEQ ID NO 247
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 247
uccgcaguau ggaucggca					19

<210> SEQ ID NO 248
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 248
accacgaguc uagacucug					19

<210> SEQ ID NO 249
<211> LENGTH: 19
<212> TYPE: RNA

```
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 249
agcuuggagg cuugaacag                                              19

<210> SEQ ID NO 250
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 250
auuuaugccu acagccucc                                              19

<210> SEQ ID NO 251
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 251
uuuaugccua cagccuccu                                              19

<210> SEQ ID NO 252
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 252
aaauugagag aaguccacc                                              19

<210> SEQ ID NO 253
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
```

-continued

```
<223> OTHER INFORMATION: /mod_base = "nucleoside: lacks 5'-phosphate
      group"

<400> SEQUENCE: 253
gcagagguga aaaaguugc                                                      19

<210> SEQ ID NO 254
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 254
tcgccuguaa cacgagcag                                                      19

<210> SEQ ID NO 255
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 255
acugaacaaa uggcacuag                                                      19

<210> SEQ ID NO 256
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 256
ccgcaguaug gaucggcag                                                      19

<210> SEQ ID NO 257
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

<400> SEQUENCE: 257
ggugaagcga agugcacac                                                    19

<210> SEQ ID NO 258
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 258
gcccgccugu aacacgagc                                                    19

<210> SEQ ID NO 259
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 259
gaaguguuga uaagauagg                                                    19

<210> SEQ ID NO 260
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 260
ugcgacgcgg cgauugaga                                                    19

<210> SEQ ID NO 261
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 261
ugagaaggca cagacgggc                                                    19

<210> SEQ ID NO 262

```
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 262
ggaaguguug auaagauag                                                    19

<210> SEQ ID NO 263
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 263
gaggacaaac gggcaacau                                                    19

<210> SEQ ID NO 264
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 264
ggacaaacgg gcaacauac                                                    19

<210> SEQ ID NO 265
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 265
gugcagaggu gaagcgaag                                                    19

<210> SEQ ID NO 266
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
```

<221> NAME/KEY: modified_base
<222> LOCATION: 1
<223> OTHER INFORMATION: /mod_base = "nucleoside: lacks 5'-phosphate
      group"

<400> SEQUENCE: 266
aggugaagcg aagugcaca                                            19

<210> SEQ ID NO 267
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 267
cgggacugcg aauuuuggc                                            19

<210> SEQ ID NO 268
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 268
cgccuguaac acgagcagg                                            19

<210> SEQ ID NO 269
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 269
agugcgaauc cacacucca                                            19

<210> SEQ ID NO 270
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 270
ugccucaagg ucggucguu                    19

<210> SEQ ID NO 271
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 271
ccacgagucu agacucugu                    19

<210> SEQ ID NO 272
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 272
cuucugcgac gcggcgauu                    19

<210> SEQ ID NO 273
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 273
gacaaacggg caacauacc                    19

<210> SEQ ID NO 274
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 274
uuccgcagua uggaucggc                    19

<210> SEQ ID NO 275
<211> LENGTH: 19
<212> TYPE: RNA
<213> ORGANISM: Artificial sequence

```
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 275
aguguugaua agauagggc                                                 19

<210> SEQ ID NO 276
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 276
caaauggcac uaguaaacu                                                 19

<210> SEQ ID NO 277
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 277
ucaaggucgg ucguugaca                                                 19

<210> SEQ ID NO 278
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 278
cuagaaaauu gagagaagu                                                 19

<210> SEQ ID NO 279
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
```

-continued

```
    group"

<400> SEQUENCE: 279
gacaaaggac gucccgcgc                                                  19

<210> SEQ ID NO 280
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 280
aguccaccac gagucuaga                                                  19

<210> SEQ ID NO 281
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 281
gaguuccgca guauggauc                                                  19

<210> SEQ ID NO 282
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 282
gcaguaugga ucggcagag                                                  19

<210> SEQ ID NO 283
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 283
cgcaguaugg aucggcaga                                                  19
```

-continued

```
<210> SEQ ID NO 284
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 284
caguauggau cggcagagg                                                19

<210> SEQ ID NO 285
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 285
accgcguaaa gagaggugc                                                19

<210> SEQ ID NO 286
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 286
gcgaggcgag ggaguucuu                                                19

<210> SEQ ID NO 287
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 287
cugcgaggcg agggaguuc                                                19

<210> SEQ ID NO 288
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 288
gcccuagaaa auugagaga                                               19

<210> SEQ ID NO 289
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 289
cguaaagaga ggugcgccc                                               19

<210> SEQ ID NO 290
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 290
guuccgcagu auggaucgg                                               19

<210> SEQ ID NO 291
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 291
ucugcgaggc gagggaguu                                               19

<210> SEQ ID NO 292
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 292
```

-continued guauggaucg gcagaggag                                    19

<210> SEQ ID NO 293
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 293
gagugcgaau ccacacucc                                    19

<210> SEQ ID NO 294
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 294
guaaagagag gugcgcccg                                    19

<210> SEQ ID NO 295
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 295
gcgacgcggc gauugagac                                    19

<210> SEQ ID NO 296
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 296
ggaguuccgc aguauggau                                    19

<210> SEQ ID NO 297
<211> LENGTH: 19
<212> TYPE: RNA

```
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 297
ccgcguaaag agaggugcg                                                  19

<210> SEQ ID NO 298
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 298
gccucaaggu cggucguug                                                  19

<210> SEQ ID NO 299
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 299
uaggaguucc gcaguaugg                                                  19

<210> SEQ ID NO 300
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 300
gggucguccg cgggauuca                                                  19

<210> SEQ ID NO 301
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
```

```
<223> OTHER INFORMATION: /mod_base = "nucleoside: lacks 5'-phosphate
      group"

<400> SEQUENCE: 301
ugcgaggcga gggaguucu                                                     19

<210> SEQ ID NO 302
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 302
gcguaaagag aggugcgcc                                                     19

<210> SEQ ID NO 303
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 303
cgcguaaaga gaggugcgc                                                     19

<210> SEQ ID NO 304
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 304
gucguccgcg ggauucagc                                                     19

<210> SEQ ID NO 305
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 305
gcagagguga agcgaagug                                                     19
```

```
<210> SEQ ID NO 306
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 306
cugcgacgcg gcgauugag                                                19

<210> SEQ ID NO 307
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 307
ggauucagcg ccgacggga                                                19

<210> SEQ ID NO 308
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 308
ggucguccgc gggauucag                                                19

<210> SEQ ID NO 309
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 309
caccacgagu cuagacucu                                                19

<210> SEQ ID NO 310
<211> LENGTH: 19
<212> TYPE: RNA
<213> ORGANISM: Artificial sequence
<220> FEATURE:
<223> OTHER INFORMATION: Description of the artificial sequence:
``` antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 310
aggaguuccg caguaugga                                                    19

<210> SEQ ID NO 311
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 311
cguccgcggg auucagcgc                                                    19

<210> SEQ ID NO 312
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 312
aggagugcga auccacacu                                                    19

<210> SEQ ID NO 313
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 313
gccuguaaca cgagcaggg                                                    19

<210> SEQ ID NO 314
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

```
<400> SEQUENCE: 314
cgggucgucc gcgggauuc                                                19

<210> SEQ ID NO 315
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 315
gccacccaag gcacagcuu                                                19

<210> SEQ ID NO 316
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 316
ccuguaacac gagcagggc                                                19

<210> SEQ ID NO 317
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 317
gauucagcgc cgacgggac                                                19

<210> SEQ ID NO 318
<211> LENGTH: 19
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 318
ccggaagugu ugauaagau                                                19

<210> SEQ ID NO 319
<211> LENGTH: 19
```

```
<212> TYPE: RNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 319
uuccggaagu guugauaag                                                19

<210> SEQ ID NO 320
<211> LENGTH: 19
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2..19
<223> OTHER INFORMATION: /mod_base = "2'-hydroxy corresponding
      nucleoside"

<400> SEQUENCE: 320
tuccggaagu guugauaag                                                19

<210> SEQ ID NO 321
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 8, 10, 11, 13, 14, 15, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 9, 12, 16
<223> OTHER INFORMATION: /mod_base = "2'-hydroxy corresponding
      nucleoside"

<400> SEQUENCE: 321
caagguaugu ugcccguuut t                                             21

<210> SEQ ID NO 322
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
```

```
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 322
cuguaggcau aaauugguat                                                    20

<210> SEQ ID NO 323
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 8, 10, 11, 12, 13, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 7, 9, 14, 17, 19
<223> OTHER INFORMATION: /mod_base = "2'-hydroxy corresponding
      nucleoside"

<400> SEQUENCE: 323
ucugcggcgu uuuaucauat t                                                  21

<210> SEQ ID NO 324
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
```

```
<221> NAME/KEY: modified_base
<222> LOCATION: 20
<223> OTHER INFORMATION: /mod_base = "3'-3'-linked desoxythymidine"

<400> SEQUENCE: 324
ucugcggcgu uuuaucauat                                                    20

<210> SEQ ID NO 325
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 8, 9, 10, 13, 14, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 11, 12, 15
<223> OTHER INFORMATION: /mod_base = "2'-hydroxy corresponding
      nucleoside"

<400> SEQUENCE: 325
accucugccu aaucaucuct t                                                  21

<210> SEQ ID NO 326
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 326
uuuacuagug ccauuuguat                                                    20

<210> SEQ ID NO 327
<211> LENGTH: 20
<212> TYPE: DNA
<213> ORGANISM: Artificial sequence
<220> FEATURE:
<223> OTHER INFORMATION: Description of the artificial sequence: sense
``` strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
       nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
       nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 327
accucugccu aaucaucuat                                                    20

<210> SEQ ID NO 328
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 1, 2, 4, 8, 10, 14, 15, 18, 19
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 9, 11, 12, 13, 16, 17
<223> OTHER INFORMATION: /mod_base = "2'-hydroxy corresponding
       nucleoside"

<400> SEQUENCE: 328
cuguaggcau aaauuggyct t                                                  21

<210> SEQ ID NO 329
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 1, 2, 3, 4, 5, 7, 10, 12, 13, 14, 15, 17, 18
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"

```
<220> FEATURE:
<221> NAME/KEY: modified_base
<222> LOCATION: 6, 8, 9, 11, 16, 19
<223> OTHER INFORMATION: /mod_base = "2'-hydroxy corresponding
      nucleoside"

<400> SEQUENCE: 329
ugucugcggc guuuuaucat t                                              21

<210> SEQ ID NO 330
<211> LENGTH: 20
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 330
ugucugcggc guuuuaucat                                                20

<210> SEQ ID NO 331
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 7, 9, 10, 12, 13, 14, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 8, 11, 15, 19
<223> OTHER INFORMATION: /mod_base = "2'-hydroxy corresponding
      nucleoside"

<400> SEQUENCE: 331
uacuagugcc auuuguucat t                                              21

<210> SEQ ID NO 332
<211> LENGTH: 20
<212> TYPE: DNA
<213> ORGANISM: Artificial sequence
```

```
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 332
uacuagugcc auuuguucat                                                    20

<210> SEQ ID NO 333
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 333
caacuuuuuc accucugcat                                                    20

<210> SEQ ID NO 334
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 8, 9, 10, 13, 16, 17, 18
<223> OTHER INFORMATION: /mod_base = "2'-O-methyl corresponding
      nucleoside"
<220> FEATURE:
<221> NAME/KEY: modified_base
```

```
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 11, 12, 14, 15, 19
<223> OTHER INFORMATION: /mod_base = "2'-hydroxy corresponding
      nucleoside"

<400> SEQUENCE: 334
ccauuuguuc agugguucgt t                                             21

<210> SEQ ID NO 335
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 8, 9, 10, 12, 13, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 11, 14, 15, 17, 19
<223> OTHER INFORMATION: /mod_base = "2'-hydroxy corresponding
      nucleoside"

<400> SEQUENCE: 335
ccaaguguuu gcugacgcat t                                             21

<210> SEQ ID NO 336
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 336
ccaaguguuu gcugacgcat                                               20

<210> SEQ ID NO 337
<211> LENGTH: 20
```

```
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 337
ccauuuguuc agugguucat                                                   20

<210> SEQ ID NO 338
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 9, 11, 12, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 10, 13, 17
<223> OTHER INFORMATION: /mod_base = "2'-hydroxy corresponding
      nucleoside"

<400> SEQUENCE: 338
uuuacuagug ccauuuguut t                                                 21

<210> SEQ ID NO 339
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
```

```
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 339
caccucugcc uaaucaucat                                                       20

<210> SEQ ID NO 340
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 7, 10, 11, 12, 14, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 8, 9, 13, 16, 17, 19
<223> OTHER INFORMATION: /mod_base = "2'-hydroxy corresponding
      nucleoside"

<400> SEQUENCE: 340
cuggcucagu uuacuagugt t                                                     21

<210> SEQ ID NO 341
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 341
caagguaugu ugcccguuat                                                       20
```

```
<210> SEQ ID NO 342
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 342
cuggcucagu uuacuaguat                                              20

<210> SEQ ID NO 343
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 8, 12, 14, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 9, 10, 11, 13, 15, 16, 17
<223> OTHER INFORMATION: /mod_base = "2'-hydroxy corresponding
      nucleoside"

<400> SEQUENCE: 343
gaggcuguag gcauaaauut t                                            21

<210> SEQ ID NO 344
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 8, 9, 12, 14, 15, 17, 18, 19
```

-continued

```
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 10, 11, 13, 16
<223> OTHER INFORMATION: /mod_base = "2'-hydroxy corresponding
      nucleoside"

<400> SEQUENCE: 344
caguuuacua gugccauuut t                                              21

<210> SEQ ID NO 345
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 8, 9, 11, 12, 13, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 10, 14, 18
<223> OTHER INFORMATION: /mod_base = "2'-hydroxy corresponding
      nucleoside"

<400> SEQUENCE: 345
agguauguug cccguuugut t                                              21

<210> SEQ ID NO 346
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 346
uauguugccc guuuguccat                                                20
```

```
<210> SEQ ID NO 347
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 347
gaggcuguag gcauaaauat                                                  20

<210> SEQ ID NO 348
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 9, 11, 12, 13, 14, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 8, 10, 15, 18
<223> OTHER INFORMATION: /mod_base = "2'-hydroxy corresponding
      nucleoside"

<400> SEQUENCE: 348
gucugcggcg uuuuaucaut t                                                21

<210> SEQ ID NO 349
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
```

```
<221> NAME/KEY: modified_base
<222> LOCATION: 1, 2, 4, 5, 6, 7, 8, 9, 10, 12, 13, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 11, 17
<223> OTHER INFORMATION: /mod_base = "2'-hydroxy corresponding
      nucleoside"

<400> SEQUENCE: 349
caacuuuuuc accucugcct t                                              21

<210> SEQ ID NO 350
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 8, 10, 11, 12, 13, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 9, 14, 19
<223> OTHER INFORMATION: /mod_base = "2'-hydroxy corresponding
      nucleoside"

<400> SEQUENCE: 350
ccgugugcac uucgcuucat t                                              21

<210> SEQ ID NO 351
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 351
```
ccgugugcac uucgcuucat 20

<210> SEQ ID NO 352
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 352
ucaagguaug uugcccguat 20

<210> SEQ ID NO 353
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 353
caguuuacua gugccauuat 20

<210> SEQ ID NO 354
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate

```
            group"
<220> FEATURE:
<221> NAME/KEY: modified_base
<222> LOCATION: 1, 2, 4, 8, 9, 10, 11, 12, 13, 14, 15, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 16, 17
<223> OTHER INFORMATION: /mod_base = "2'-hydroxy corresponding
      nucleoside"

<400> SEQUENCE: 354
ugguggacuu cucucaauut t                                           21

<210> SEQ ID NO 355
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 355
agguauguug cccguuugat                                             20

<210> SEQ ID NO 356
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 8, 10, 11, 13, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 9, 12, 14, 15, 16, 18, 19
<223> OTHER INFORMATION: /mod_base = "2'-hydroxy corresponding
      nucleoside"
```

-continued

<400> SEQUENCE: 356
cugcucgugu uacaggcggt t                                          21

<210> SEQ ID NO 357
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 8, 9, 10, 12, 13, 14, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 11, 15
<223> OTHER INFORMATION: /mod_base = "2'-hydroxy corresponding
      nucleoside"

<400> SEQUENCE: 357
uauguugccc guuuguccut t                                          21

<210> SEQ ID NO 358
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 7, 9, 11, 12, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 8, 10, 13, 17
<223> OTHER INFORMATION: /mod_base = "2'-hydroxy corresponding
      nucleoside"

<400> SEQUENCE: 358
ucaagguaug uugcccguut t                                          21

<210> SEQ ID NO 359
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base

```
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 10, 12, 13, 14, 15, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 17, 18, 19
<223> OTHER INFORMATION: /mod_base = "2'-hydroxy corresponding
      nucleoside"

<400> SEQUENCE: 359
ucuuaucaac acuuccggat t                                              21

<210> SEQ ID NO 360
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 360
ucuuaucaac acuuccggat                                                20

<210> SEQ ID NO 361
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 7, 9, 10, 11, 14, 15, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 8, 12, 13, 16
```

<223> OTHER INFORMATION: /mod_base = "2'-hydroxy corresponding
       nucleoside"

<400> SEQUENCE: 361
caccucugcc uaaucaucut t          21

<210> SEQ ID NO 362
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 1, 2, 10, 11, 12, 13, 14, 18, 19
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 7, 8, 9, 15, 16, 17
<223> OTHER INFORMATION: /mod_base = "2'-hydroxy corresponding
       nucleoside"

<400> SEQUENCE: 362
auaagaggac ucuuggacut t          21

<210> SEQ ID NO 363
<211> LENGTH: 20
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
       nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
       nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 363
gucugcggcg uuuuaucaat          20

<210> SEQ ID NO 364
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA

```
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 10, 11, 12, 13, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 9, 14, 16, 17, 18
<223> OTHER INFORMATION: /mod_base = "2'-hydroxy corresponding
      nucleoside"

<400> SEQUENCE: 364
ggcgcugaau cccgcggact t                                              21

<210> SEQ ID NO 365
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 8, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 9, 10, 11, 12, 13, 14, 19
<223> OTHER INFORMATION: /mod_base = "2'-hydroxy corresponding
      nucleoside"

<400> SEQUENCE: 365
cgcgucgcag aagaucucat t                                              21

<210> SEQ ID NO 366
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 9, 12, 13, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
```

```
<221> NAME/KEY: modified_base
<222> LOCATION: 4, 7, 8, 10, 11, 14, 15
<223> OTHER INFORMATION: /mod_base = "2'-hydroxy corresponding
      nucleoside"

<400> SEQUENCE: 366
aaugucaacg accgaccuut t                                              21

<210> SEQ ID NO 367
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 7, 8, 9, 11, 12, 15, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 10, 13, 14, 16, 19
<223> OTHER INFORMATION: /mod_base = "2'-hydroxy corresponding
      nucleoside"

<400> SEQUENCE: 367
gcucaguuua cuagugccat t                                              21

<210> SEQ ID NO 368
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 368
ugguggacuu cucucaauat                                                20

<210> SEQ ID NO 369
<211> LENGTH: 21
<212> TYPE: DNA
<213> ORGANISM: Artificial sequence
<220> FEATURE:
```

<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 8, 10, 11, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 9, 12, 14, 15, 16, 17, 18, 19
<223> OTHER INFORMATION: /mod_base = "2'-hydroxy corresponding
      nucleoside"

<400> SEQUENCE: 369
aucgccgcgu cgcagaagat t                                            21

<210> SEQ ID NO 370
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 9, 10, 11, 14, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 12, 13, 15, 16
<223> OTHER INFORMATION: /mod_base = "2'-hydroxy corresponding
      nucleoside"

<400> SEQUENCE: 370
gccauuuguu cguggguuct t                                            21

<210> SEQ ID NO 371
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 8, 10, 11, 13, 18, 19
<223> OTHER INFORMATION: /mod_base = "2'-O-methyl corresponding
      nucleoside"
<220> FEATURE:
<221> NAME/KEY: modified_base
<222> LOCATION: 21

```
<223> OTHER INFORMATION: /mod_base = "5'-phosphorothioate thymidine"
<220> FEATURE:
<221> NAME/KEY: modified_base
<222> LOCATION: 3, 7, 9, 12, 14, 15, 16, 17
<223> OTHER INFORMATION: /mod_base = "2'-hydroxy corresponding
      nucleoside"

<400> SEQUENCE: 371
cgauccauac ugcggaacut t                                              21

<210> SEQ ID NO 372
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 8, 10, 11, 12, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 9, 13, 14, 17
<223> OTHER INFORMATION: /mod_base = "2'-hydroxy corresponding
      nucleoside"

<400> SEQUENCE: 372
ucaccucugc cuaaucauct t                                              21

<210> SEQ ID NO 373
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 7, 8, 9, 10, 11, 12, 13, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 14, 15
<223> OTHER INFORMATION: /mod_base = "2'-hydroxy corresponding
      nucleoside"

<400> SEQUENCE: 373
guggacuucu cucaauuuut t                                              21

<210> SEQ ID NO 374
<211> LENGTH: 21
<212> TYPE: DNA
```

```
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 7, 8, 10, 12, 13, 14, 15, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 9, 11, 17, 18, 19
<223> OTHER INFORMATION: /mod_base = "2'-hydroxy corresponding
      nucleoside"

<400> SEQUENCE: 374
gggucaccau auucuugggt t                                           21

<210> SEQ ID NO 375
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 8, 10, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 11, 12, 13, 14, 15, 16
<223> OTHER INFORMATION: /mod_base = "2'-hydroxy corresponding
      nucleoside"

<400> SEQUENCE: 375
gccgcgucgc agaagaucut t                                           21

<210> SEQ ID NO 376
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 8, 9, 11, 13, 14, 16
<223> OTHER INFORMATION: /mod_base = "2'-O-methyl corresponding
      nucleoside"
<220> FEATURE:
```

```
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 10, 12, 15, 17, 18, 19
<223> OTHER INFORMATION: /mod_base = "2'-hydroxy corresponding
      nucleoside"

<400> SEQUENCE: 376
ucaaucgccg cgucgcagat t                                               21

<210> SEQ ID NO 377
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 7, 9, 10, 11, 13, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 12, 14, 15, 17
<223> OTHER INFORMATION: /mod_base = "2'-hydroxy corresponding
      nucleoside"

<400> SEQUENCE: 377
uggauguguc ugcggcguut t                                               21

<210> SEQ ID NO 378
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 8, 12, 13, 14, 15, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 10, 11, 17, 18, 19
<223> OTHER INFORMATION: /mod_base = "2'-hydroxy corresponding
      nucleoside"

<400> SEQUENCE: 378
uacuguucaa gccuccaagt t                                               21

<210> SEQ ID NO 379
```

```
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 10, 12, 13, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 14, 18
<223> OTHER INFORMATION: /mod_base = "2'-hydroxy corresponding
      nucleoside"

<400> SEQUENCE: 379
guuuacuagu gccauuugut t                                              21

<210> SEQ ID NO 380
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 6, 8, 9, 11, 12, 13, 15, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 7, 10, 14, 18, 19
<223> OTHER INFORMATION: /mod_base = "2'-hydroxy corresponding
      nucleoside"

<400> SEQUENCE: 380
acuagugcca uuuguucagt t                                              21

<210> SEQ ID NO 381
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 7, 9, 16, 17, 18, 19
<223> OTHER INFORMATION: /mod_base = "2'-O-methyl corresponding
``` nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 10, 11, 12, 13, 14, 15
<223> OTHER INFORMATION: /mod_base = "2'-hydroxy corresponding
      nucleoside"

<400> SEQUENCE: 381
ccgcgucgca gaagaucuct t                                              21

<210> SEQ ID NO 382
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 8, 9, 12, 14, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 10, 11, 13, 19
<223> OTHER INFORMATION: /mod_base = "2'-hydroxy corresponding
      nucleoside"

<400> SEQUENCE: 382
uaucuuauca acacuuccgt t                                              21

<210> SEQ ID NO 383
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 9, 10, 11, 13, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 7, 8, 12, 14, 15
<223> OTHER INFORMATION: /mod_base = "2'-hydroxy corresponding
      nucleoside"

<400> SEQUENCE: 383
ggccaaaauu cgcagucccu t                                              21

-continued

```
<210> SEQ ID NO 384
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 8, 9, 11, 12, 13, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 10, 14, 15, 18
<223> OTHER INFORMATION: /mod_base = "2'-hydroxy corresponding
      nucleoside"

<400> SEQUENCE: 384
uucaccucug ccuaaucaut t                                              21

<210> SEQ ID NO 385
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 6, 7, 8, 10, 11, 14, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 9, 12, 13, 15, 18
<223> OTHER INFORMATION: /mod_base = "2'-hydroxy corresponding
      nucleoside"

<400> SEQUENCE: 385
cucaguuuac uagugccaut t                                              21

<210> SEQ ID NO 386
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
```

```
<222> LOCATION: 1, 2, 3, 4, 6, 7, 8, 10, 11, 12, 14, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 13
<223> OTHER INFORMATION: /mod_base = "2'-hydroxy corresponding
      nucleoside"

<400> SEQUENCE: 386
uguugcccgu uuguccucut t                                              21

<210> SEQ ID NO 387
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 7, 9, 10, 11, 13, 14, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 12, 16, 17, 19
<223> OTHER INFORMATION: /mod_base = "2'-hydroxy corresponding
      nucleoside"

<400> SEQUENCE: 387
uagugccauu uguucagugt t                                              21

<210> SEQ ID NO 388
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 7, 11, 13, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 8, 9, 10, 12, 14, 15, 16, 19
<223> OTHER INFORMATION: /mod_base = "2'-hydroxy corresponding
      nucleoside"

<400> SEQUENCE: 388
```
aggcuguagg cauaaauugt t                                            21

<210> SEQ ID NO 389
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 7, 8, 10, 13, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 9, 11, 12, 14, 19
<223> OTHER INFORMATION: /mod_base = "2'-hydroxy corresponding
      nucleoside"

<400> SEQUENCE: 389
augugucugc ggcguuuuat t                                            21

<210> SEQ ID NO 390
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 390
augugucugc ggcguuuuat                                              20

<210> SEQ ID NO 391
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

```
<220> FEATURE:
<221> NAME/KEY: modified_base
<222> LOCATION: 1, 2, 3, 4, 5, 7, 8, 9, 10, 12, 13, 14, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 11, 17, 19
<223> OTHER INFORMATION: /mod_base = "2'-hydroxy corresponding
      nucleoside"

<400> SEQUENCE: 391
acuucgcuuc accucugcat t                                           21

<210> SEQ ID NO 392
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 9, 10, 11, 12, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 8, 13, 18
<223> OTHER INFORMATION: /mod_base = "2'-hydroxy corresponding
      nucleoside"

<400> SEQUENCE: 392
cgugugcacu ucgcuucact t                                           21

<210> SEQ ID NO 393
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 9, 10, 11, 12, 13, 14, 15, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 7, 8, 17, 18
<223> OTHER INFORMATION: /mod_base = "2'-hydroxy corresponding
      nucleoside"
```

<400> SEQUENCE: 393
gugguggacu ucucucaaut t                                                    21

<210> SEQ ID NO 394
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 9, 12, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 10, 11, 13, 18
<223> OTHER INFORMATION: /mod_base = "2'-hydroxy corresponding
      nucleoside"

<400> SEQUENCE: 394
ugugucugcg gcguuuuaut t                                                    21

<210> SEQ ID NO 395
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 7, 9, 10, 12, 13, 14, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 11, 15, 19
<223> OTHER INFORMATION: /mod_base = "2'-hydroxy corresponding
      nucleoside"

<400> SEQUENCE: 395
aagguauguu gcccguuugt t                                                    21

<210> SEQ ID NO 396
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1

```
<223> OTHER INFORMATION: /mod_base = "nucleoside: lacks 5'-phosphate
      group"
<220> FEATURE:
<221> NAME/KEY: modified_base
<222> LOCATION: 1, 2, 5, 8, 9, 12, 13, 14, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 7, 10, 11, 16, 17, 18, 19
<223> OTHER INFORMATION: /mod_base = "2'-hydroxy corresponding
      nucleoside"

<400> SEQUENCE: 396
ucaacgaccg accuugaggt t                                              21

<210> SEQ ID NO 397
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 11, 12, 13, 14, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 7, 8, 9, 10, 16, 17, 18
<223> OTHER INFORMATION: /mod_base = "2'-hydroxy corresponding
      nucleoside"

<400> SEQUENCE: 397
cauaagagga cucuuggact t                                              21

<210> SEQ ID NO 398
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 6, 9, 10, 13, 14, 15, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 7, 8, 11, 12, 17, 18, 19
<223> OTHER INFORMATION: /mod_base = "2'-hydroxy corresponding
```

-continued nucleoside"

<400> SEQUENCE: 398
gucaacgacc gaccuugagt t                                        21

<210> SEQ ID NO 399
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 8, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 9, 10, 11, 12, 13, 15, 16, 17, 18, 19
<223> OTHER INFORMATION: /mod_base = "2'-hydroxy corresponding
      nucleoside"

<400> SEQUENCE: 399
auauucuugg gaacaagagt t                                        21

<210> SEQ ID NO 400
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 9, 10, 12, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 8, 11, 13, 14, 15, 17, 18, 19
<223> OTHER INFORMATION: /mod_base = "2'-hydroxy corresponding
      nucleoside"

<400> SEQUENCE: 400
ugcucguguu acaggcgggt t                                        21

<210> SEQ ID NO 401
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:

```
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 7, 8, 10, 12, 13, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 9, 11, 14, 16, 17, 18, 19
<223> OTHER INFORMATION: /mod_base = "2'-hydroxy corresponding
      nucleoside"

<400> SEQUENCE: 401
caaucgccgc gucgcagaat t                                           21

<210> SEQ ID NO 402
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 11, 12, 13, 14, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 9, 10, 16, 17, 18
<223> OTHER INFORMATION: /mod_base = "2'-hydroxy corresponding
      nucleoside"

<400> SEQUENCE: 402
acuguucaag ccuccaagct t                                           21

<210> SEQ ID NO 403
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 8, 9, 11, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
```

```
<222> LOCATION: 5, 7, 10, 12, 13, 14, 15, 16, 17
<223> OTHER INFORMATION: /mod_base = "2'-hydroxy corresponding
      nucleoside"

<400> SEQUENCE: 403
cgccgcgucg cagaagauct t                                              21

<210> SEQ ID NO 404
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 9, 12, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 11, 13, 14, 18
<223> OTHER INFORMATION: /mod_base = "2'-hydroxy corresponding
      nucleoside"

<400> SEQUENCE: 404
cauuuguuca gugguucgut t                                              21

<210> SEQ ID NO 405
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 8, 9, 10, 11, 13, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 7, 12, 14, 15, 16, 18, 19
<223> OTHER INFORMATION: /mod_base = "2'-hydroxy corresponding
      nucleoside"

<400> SEQUENCE: 405
cgcugaaucc cgcggacgat t                                              21

<210> SEQ ID NO 406
<211> LENGTH: 21
<212> TYPE: DNA
<213> ORGANISM: Artificial sequence
<220> FEATURE:
<223> OTHER INFORMATION: Description of the artificial sequence: sense
```

```
                    strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 8, 9, 11, 13, 14, 15, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 10, 12, 18, 19
<223> OTHER INFORMATION: /mod_base = "2'-hydroxy corresponding
      nucleoside"

<400> SEQUENCE: 406
ugggucacca uauucuuggt t                                              21

<210> SEQ ID NO 407
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 8, 9, 12, 13, 14, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 10, 11, 15, 17
<223> OTHER INFORMATION: /mod_base = "2'-hydroxy corresponding
      nucleoside"

<400> SEQUENCE: 407
uccucugccg auccauacut t                                              21

<210> SEQ ID NO 408
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 8, 11, 12, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
```

```
<220> FEATURE:
<221> NAME/KEY: modified_base
<222> LOCATION: 3, 6, 7, 9, 10, 13, 14, 19
<223> OTHER INFORMATION: /mod_base = "2'-hydroxy corresponding
      nucleoside"

<400> SEQUENCE: 408
augucaacga ccgaccuugt t                                             21

<210> SEQ ID NO 409
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 9, 12, 13, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 11, 14, 19
<223> OTHER INFORMATION: /mod_base = "2'-hydroxy corresponding
      nucleoside"

<400> SEQUENCE: 409
ccucugccua aucaucucat t                                             21

<210> SEQ ID NO 410
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 9, 11, 12, 13, 14, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 8, 10, 15
<223> OTHER INFORMATION: /mod_base = "2'-hydroxy corresponding
      nucleoside"

<400> SEQUENCE: 410
accgugugca cuucgcuuct t                                             21

<210> SEQ ID NO 411
<211> LENGTH: 21
<212> TYPE: DNA
<213> ORGANISM: Artificial sequence
```

-continued

<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 7, 8, 9, 11, 13, 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 10, 12, 15, 17, 18, 19
<223> OTHER INFORMATION: /mod_base = "2'-hydroxy corresponding
      nucleoside"

<400> SEQUENCE: 411
ugccgaucca uacugcggat t                                              21

<210> SEQ ID NO 412
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 7, 8, 12, 13, 14, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 9, 10, 11, 15, 17, 18
<223> OTHER INFORMATION: /mod_base = "2'-hydroxy corresponding
      nucleoside"

<400> SEQUENCE: 412
cagagucuag acucgugggut t                                             21

<210> SEQ ID NO 413
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 10, 11, 12, 13, 14, 18, 19
<223> OTHER INFORMATION: /mod_base = "2'-O-methyl corresponding
      nucleoside"
<220> FEATURE:
<221> NAME/KEY: modified_base

```
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 8, 9, 15, 16, 17
<223> OTHER INFORMATION: /mod_base = "2'-hydroxy corresponding
      nucleoside"

<400> SEQUENCE: 413
cuguucaagc cuccaagcut t                                               21

<210> SEQ ID NO 414
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 7, 9, 13, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 8, 10, 11, 12, 14, 16, 17, 18
<223> OTHER INFORMATION: /mod_base = "2'-hydroxy corresponding
      nucleoside"

<400> SEQUENCE: 414
ggaggcugua ggcauaaaut t                                               21

<210> SEQ ID NO 415
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 7, 8, 10, 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 9, 11, 12, 13, 15, 17, 18, 19
<223> OTHER INFORMATION: /mod_base = "2'-hydroxy corresponding
      nucleoside"

<400> SEQUENCE: 415
aggaggcugu aggcauaaat t                                               21

<210> SEQ ID NO 416
<211> LENGTH: 21
```

```
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 7, 8, 9, 10, 11, 12, 13, 14, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 15, 16
<223> OTHER INFORMATION: /mod_base = "2'-hydroxy corresponding
      nucleoside"

<400> SEQUENCE: 416
gguggacuuc ucucaauuut t                                              21

<210> SEQ ID NO 417
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 7, 8, 9, 10, 11, 13, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 12, 18
<223> OTHER INFORMATION: /mod_base = "2'-hydroxy corresponding
      nucleoside"

<400> SEQUENCE: 417
gcaacuuuuu caccucugct t                                              21

<210> SEQ ID NO 418
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
```

```
-continued

<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 418
cugcucgugu uacaggcgat                                                    20

<210> SEQ ID NO 419
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 7, 8, 10, 11, 12, 14, 15, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 9, 13, 17, 18
<223> OTHER INFORMATION: /mod_base = "2'-hydroxy corresponding
      nucleoside"

<400> SEQUENCE: 419
cuagugccau uuguucagut t                                                  21

<210> SEQ ID NO 420
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 8, 9, 10, 12, 14, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 7, 11, 13, 16, 18, 19
<223> OTHER INFORMATION: /mod_base = "2'-hydroxy corresponding
      nucleoside"

<400> SEQUENCE: 420
cugccgaucc auacugcggt t                                                  21
```

```
<210> SEQ ID NO 421
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 8, 9, 10, 11, 13, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 12, 17
<223> OTHER INFORMATION: /mod_base = "2'-hydroxy corresponding
      nucleoside"

<400> SEQUENCE: 421
gugugcacuu cgcuucacct t                                              21

<210> SEQ ID NO 422
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 8, 9, 11, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 10, 12, 13, 14, 16, 17, 18
<223> OTHER INFORMATION: /mod_base = "2'-hydroxy corresponding
      nucleoside"

<400> SEQUENCE: 422
gcucguguua caggcgggct t                                              21

<210> SEQ ID NO 423
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 8, 10, 11, 14, 16, 17, 18, 19
```

```
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 9, 12, 13, 15
<223> OTHER INFORMATION: /mod_base = "2'-hydroxy corresponding
      nucleoside"

<400> SEQUENCE: 423
ccuaucuuau caacacuuct t                                              21

<210> SEQ ID NO 424
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 7, 8, 10, 11, 13, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 9, 12, 14, 17, 19
<223> OTHER INFORMATION: /mod_base = "2'-hydroxy corresponding
      nucleoside"

<400> SEQUENCE: 424
ucucaaucgc cgcgucgcat t                                              21

<210> SEQ ID NO 425
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 8, 10, 12, 13, 14, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 11, 19
<223> OTHER INFORMATION: /mod_base = "2'-hydroxy corresponding
      nucleoside"

<400> SEQUENCE: 425
gcccgucugu gccuucucat t                                              21
```

<210> SEQ ID NO 426
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 9, 10, 13, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 8, 11, 12, 14
<223> OTHER INFORMATION: /mod_base = "2'-hydroxy corresponding
      nucleoside"

<400> SEQUENCE: 426
cuaucuuauc aacacuucct t                                              21

<210> SEQ ID NO 427
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 7, 8, 9, 11, 12, 13, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 10, 14
<223> OTHER INFORMATION: /mod_base = "2'-hydroxy corresponding
      nucleoside"

<400> SEQUENCE: 427
auguugcccg uuuguccuct t                                              21

<210> SEQ ID NO 428
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:

<221> NAME/KEY: modified_base
<222> LOCATION: 1, 2, 4, 6, 7, 9, 10, 11, 13, 14, 15, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 12, 16
<223> OTHER INFORMATION: /mod_base = "2'-hydroxy corresponding
      nucleoside"

<400> SEQUENCE: 428
guauguugcc cguuugucct t                                            21

<210> SEQ ID NO 429
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 8, 9, 11, 12, 13, 14, 15, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 10, 16, 18
<223> OTHER INFORMATION: /mod_base = "2'-hydroxy corresponding
      nucleoside"

<400> SEQUENCE: 429
cuucgcuuca ccucugcact t                                            21

<210> SEQ ID NO 430
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 8, 9, 10, 12, 13, 14, 15, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 11, 16
<223> OTHER INFORMATION: /mod_base = "2'-hydroxy corresponding
      nucleoside"

<400> SEQUENCE: 430
ugugcacuuc gcuucaccut t                                21

<210> SEQ ID NO 431
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 8, 9, 10, 12, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 7, 11, 13, 14, 19
<223> OTHER INFORMATION: /mod_base = "2'-hydroxy corresponding
      nucleoside"

<400> SEQUENCE: 431
gccaaaauuc gcagucccgt t                                21

<210> SEQ ID NO 432
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 7, 9, 11, 12, 14, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 10, 13, 15, 16, 17, 19
<223> OTHER INFORMATION: /mod_base = "2'-hydroxy corresponding
      nucleoside"

<400> SEQUENCE: 432
ccugcucgug uuacaggcgt t                                21

<210> SEQ ID NO 433
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate

```
       group"
<220> FEATURE:
<221> NAME/KEY: modified_base
<222> LOCATION: 1, 2, 6, 8, 12, 13, 14, 16, 18, 19
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 9, 10, 11, 15, 17
<223> OTHER INFORMATION: /mod_base = "2'-hydroxy corresponding
       nucleoside"

<400> SEQUENCE: 433
uggagugugg auucgcacut t                                              21

<210> SEQ ID NO 434
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 1, 2, 3, 6, 7, 10, 11, 12, 13, 18
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 8, 9, 14, 15, 16, 17, 19
<223> OTHER INFORMATION: /mod_base = "2'-hydroxy corresponding
       nucleoside"

<400> SEQUENCE: 434
aacgaccgac cuugaggcat t                                              21

<210> SEQ ID NO 435
<211> LENGTH: 21
<212> TYPE: DNA
<213> ORGANISM: Artificial sequence
<220> FEATURE:
<223> OTHER INFORMATION: Description of the artificial sequence: sense
       strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 1, 2, 7, 8, 9, 13, 14, 15, 17
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 10, 11, 12, 16, 18, 19
<223> OTHER INFORMATION: /mod_base = "2'-hydroxy corresponding
       nucleoside"
```

-continued

<400> SEQUENCE: 435
acagagucua gacucguggt t                                              21

<210> SEQ ID NO 436
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 9, 11, 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 10, 13, 15, 16, 17, 18, 19
<223> OTHER INFORMATION: /mod_base = "2'-hydroxy corresponding
      nucleoside"

<400> SEQUENCE: 436
aaucgccgcg ucgcagaagt t                                              21

<210> SEQ ID NO 437
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 8, 10, 11, 12, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 13, 17
<223> OTHER INFORMATION: /mod_base = "2'-hydroxy corresponding
      nucleoside"

<400> SEQUENCE: 437
gguauguugc ccguuuguct t                                              21

<210> SEQ ID NO 438
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base

```
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 6, 7, 8, 10, 12, 13, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 9, 11, 14, 16, 17, 18, 19
<223> OTHER INFORMATION: /mod_base = "2'-hydroxy corresponding
      nucleoside"

<400> SEQUENCE: 438
gccgauccau acugcggaat t                                              21

<210> SEQ ID NO 439
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 9, 10, 12, 13, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 11, 14, 15, 17
<223> OTHER INFORMATION: /mod_base = "2'-hydroxy corresponding
      nucleoside"

<400> SEQUENCE: 439
gcccuaucuu aucaacacut t                                              21

<210> SEQ ID NO 440
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 11, 13, 14, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 12, 15, 19
```

```
<223> OTHER INFORMATION: /mod_base = "2'-hydroxy corresponding
      nucleoside"

<400> SEQUENCE: 440
aguuuacuag ugccauuugt t                                              21

<210> SEQ ID NO 441
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 7, 10, 11, 14, 15, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 8, 9, 12, 13, 18, 19
<223> OTHER INFORMATION: /mod_base = "2'-hydroxy corresponding
      nucleoside"

<400> SEQUENCE: 441 ugcaacgac cgaccuugat t                                               21

<210> SEQ ID NO 442
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 7, 8, 9, 12, 13, 14, 15, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 10, 11, 18, 19
<223> OTHER INFORMATION: /mod_base = "2'-hydroxy corresponding
      nucleoside"

<400> SEQUENCE: 442
acuucucuca auuuucuagt t                                              21

<210> SEQ ID NO 443
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 9, 11, 12, 13, 14, 15, 16, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 8, 10, 17
<223> OTHER INFORMATION: /mod_base = "2'-hydroxy corresponding
      nucleoside"

<400> SEQUENCE: 443
gcgcgggacg uccuuuguct t                                              21

<210> SEQ ID NO 444
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 7, 8, 9, 11, 14, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 10, 12, 13, 15, 16, 17
<223> OTHER INFORMATION: /mod_base = "2'-hydroxy corresponding
      nucleoside"

<400> SEQUENCE: 444
ucuagacucg ugguggacut t                                              21

<210> SEQ ID NO 445
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 9, 10, 12, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
```

```
<221> NAME/KEY: modified_base
<222> LOCATION: 6, 8, 11, 13, 14, 15, 16
<223> OTHER INFORMATION: /mod_base = "2'-hydroxy corresponding
      nucleoside"

<400> SEQUENCE: 445
gauccauacu gcggaacuct t                                          21

<210> SEQ ID NO 446
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 10, 11, 12, 14, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 13, 15, 18
<223> OTHER INFORMATION: /mod_base = "2'-hydroxy corresponding
      nucleoside"

<400> SEQUENCE: 446
cucugccgau ccauacugct t                                          21

<210> SEQ ID NO 447
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 9, 10, 11, 13, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 12, 14, 17, 19
<223> OTHER INFORMATION: /mod_base = "2'-hydroxy corresponding
      nucleoside"

<400> SEQUENCE: 447
ucugccgauc cauacugcgt t                                          21

<210> SEQ ID NO 448
<211> LENGTH: 21
<212> TYPE: DNA
<213> ORGANISM: Artificial sequence
<220> FEATURE:
```

```
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 11, 12, 13, 15, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 14, 16, 19
<223> OTHER INFORMATION: /mod_base = "2'-hydroxy corresponding
      nucleoside"

<400> SEQUENCE: 448
ccucugccga uccauacugt t                                              21

<210> SEQ ID NO 449
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 8, 9, 10, 11, 12, 14, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 13, 15, 17, 18
<223> OTHER INFORMATION: /mod_base = "2'-hydroxy corresponding
      nucleoside"

<400> SEQUENCE: 449
gcaccucucu uuacgcggut t                                              21

<210> SEQ ID NO 450
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 7, 8, 9, 10, 11, 12, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
```

-continued

```
<223> OTHER INFORMATION: /mod_base = "5'-phosphorothioate thymidine"
<220> FEATURE:
<221> NAME/KEY: modified_base
<222> LOCATION: 3, 4, 5, 13, 18
<223> OTHER INFORMATION: /mod_base = "2'-hydroxy corresponding
      nucleoside"

<400> SEQUENCE: 450
aagaacuccc ucgccucgct t                                              21

<210> SEQ ID NO 451
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 8, 9, 10, 12, 13, 14, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 11, 16, 18, 19
<223> OTHER INFORMATION: /mod_base = "2'-hydroxy corresponding
      nucleoside"

<400> SEQUENCE: 451
gaacucccuc gccucgcagt t                                              21

<210> SEQ ID NO 452
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 9, 10, 11, 12, 13, 14, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 8, 15, 16, 17, 18
<223> OTHER INFORMATION: /mod_base = "2'-hydroxy corresponding
      nucleoside"

<400> SEQUENCE: 452
ucucucaauu uucuagggct t                                              21

<210> SEQ ID NO 453
<211> LENGTH: 21
<212> TYPE: DNA
```

```
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 8, 9, 10, 11, 12, 13, 14, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 17, 19
<223> OTHER INFORMATION: /mod_base = "2'-hydroxy corresponding
      nucleoside"

<400> SEQUENCE: 453
gggcgcaccu cucuuuacgt t                                              21

<210> SEQ ID NO 454
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 7, 9, 11, 12, 14, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 8, 10, 13, 15, 16, 17, 18
<223> OTHER INFORMATION: /mod_base = "2'-hydroxy corresponding
      nucleoside"

<400> SEQUENCE: 454
ccgauccaua cugcggaact t                                              21

<210> SEQ ID NO 455
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 7, 8, 9, 11, 12, 13, 14, 16
<223> OTHER INFORMATION: /mod_base = "2'-O-methyl corresponding
      nucleoside"
<220> FEATURE:
```

<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 10, 15, 17, 18, 19
<223> OTHER INFORMATION: /mod_base = "2'-hydroxy corresponding nucleoside"

<400> SEQUENCE: 455
aacucccucg ccucgcagat t          21

<210> SEQ ID NO 456
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 6, 7, 9, 10, 13, 14, 15, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 8, 11, 12, 16, 18
<223> OTHER INFORMATION: /mod_base = "2'-hydroxy corresponding nucleoside"

<400> SEQUENCE: 456
cuccucugcc gauccauact t          21

<210> SEQ ID NO 457
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 7, 11, 12, 13, 15, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 9, 10, 14, 16
<223> OTHER INFORMATION: /mod_base = "2'-hydroxy corresponding nucleoside"

<400> SEQUENCE: 457
ggagugugga uucgcacuct t          21

<210> SEQ ID NO 458

```
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 7, 9, 10, 11, 12, 13, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 18
<223> OTHER INFORMATION: /mod_base = "2'-hydroxy corresponding
      nucleoside"

<400> SEQUENCE: 458
cgggcgcacc ucucuuuact t                                           21

<210> SEQ ID NO 459
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 8, 9, 11, 12, 14, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 7, 10, 13, 15, 18
<223> OTHER INFORMATION: /mod_base = "2'-hydroxy corresponding
      nucleoside"

<400> SEQUENCE: 459
gucucaaucg ccgcgucgct t                                           21

<210> SEQ ID NO 460
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 8, 9, 11, 16, 17, 18, 19
<223> OTHER INFORMATION: /mod_base = "2'-O-methyl corresponding
```

```
        nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 10, 12, 13, 14, 15
<223> OTHER INFORMATION: /mod_base = "2'-hydroxy corresponding
        nucleoside"

<400> SEQUENCE: 460
auccauacug cggaacucct t                                              21

<210> SEQ ID NO 461
<211> LENGTH: 21
<212> TYPE: DNA
<213> ORGANISM: Artificial sequence
<220> FEATURE:
<223> OTHER INFORMATION: Description of the artificial sequence: sense
        strand of dsRNA
<220> FEATURE:
<221> NAME/KEY: modified_base
<222> LOCATION: 1
<223> OTHER INFORMATION: /mod_base = "nucleoside: lacks 5'-phosphate
        group"
<220> FEATURE:
<221> NAME/KEY: modified_base
<222> LOCATION: 1, 2, 3, 5, 6, 7, 8, 9, 10, 11, 12, 13, 15, 17
<223> OTHER INFORMATION: /mod_base = "2'-O-methyl corresponding
        nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 14, 16, 18, 19
<223> OTHER INFORMATION: /mod_base = "2'-hydroxy corresponding
        nucleoside"

<400> SEQUENCE: 461
cgcaccucuc uuuacgcggt t                                              21

<210> SEQ ID NO 462
<211> LENGTH: 21
<212> TYPE: DNA
<213> ORGANISM: Artificial sequence
<220> FEATURE:
<223> OTHER INFORMATION: Description of the artificial sequence: sense
        strand of dsRNA
<220> FEATURE:
<221> NAME/KEY: modified_base
<222> LOCATION: 1
<223> OTHER INFORMATION: /mod_base = "nucleoside: lacks 5'-phosphate
        group"
<220> FEATURE:
<221> NAME/KEY: modified_base
<222> LOCATION: 1, 2, 4, 7, 8, 11, 12, 13, 14, 19
<223> OTHER INFORMATION: /mod_base = "2'-O-methyl corresponding
        nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 9, 10, 15, 16, 17, 18
<223> OTHER INFORMATION: /mod_base = "2'-hydroxy corresponding
        nucleoside"

<400> SEQUENCE: 462
caacgaccga ccuugaggct t                                              21
```

-continued

```
<210> SEQ ID NO 463
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 7, 9, 14, 15, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 10, 11, 12, 13, 19
<223> OTHER INFORMATION: /mod_base = "2'-hydroxy corresponding
      nucleoside"

<400> SEQUENCE: 463
ccauacugcg gaacuccuat t                                             21

<210> SEQ ID NO 464
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 7, 8, 10, 14, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 9, 11, 12, 13, 15, 16
<223> OTHER INFORMATION: /mod_base = "2'-hydroxy corresponding
      nucleoside"

<400> SEQUENCE: 464
ugaaucccgc ggacgaccct t                                             21

<210> SEQ ID NO 465
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
```

<222> LOCATION: 1, 2, 5, 6, 7, 8, 9, 10, 11, 13, 14, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 12, 17, 19
<223> OTHER INFORMATION: /mod_base = "2'-hydroxy corresponding
      nucleoside"

<400> SEQUENCE: 465 agaacuccccu cgccucgcat t                                              21

<210> SEQ ID NO 466
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 8, 9, 10, 11, 12, 13, 14, 15, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 16, 18
<223> OTHER INFORMATION: /mod_base = "2'-hydroxy corresponding
      nucleoside"

<400> SEQUENCE: 466
ggcgcaccuc ucuuuacgct t                                               21

<210> SEQ ID NO 467
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 6, 7, 8, 9, 10, 11, 12, 13, 14, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 15, 17, 19
<223> OTHER INFORMATION: /mod_base = "2'-hydroxy corresponding
      nucleoside"

<400> SEQUENCE: 467
gcgcaccucu cuuuacgcgt t          21

<210> SEQ ID NO 468
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 7, 8, 9, 10, 12, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 11, 13, 14, 15, 17, 18
<223> OTHER INFORMATION: /mod_base = "2'-hydroxy corresponding
      nucleoside"

<400> SEQUENCE: 468
gcugaauccc gcggacgact t          21

<210> SEQ ID NO 469
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 8, 9, 10, 11, 13, 14, 15, 16, 17, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 12, 18
<223> OTHER INFORMATION: /mod_base = "2'-hydroxy corresponding
      nucleoside"

<400> SEQUENCE: 469
cacuucgcuu caccucugct t          21

<210> SEQ ID NO 470
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

```
<220> FEATURE:
<221> NAME/KEY: modified_base
<222> LOCATION: 1, 2, 3, 6, 7, 9, 10, 12, 14, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 8, 11, 13, 16, 18, 19
<223> OTHER INFORMATION: /mod_base = "2'-hydroxy corresponding
      nucleoside"

<400> SEQUENCE: 470
cucaaucgcc gcgucgcagt t                                              21

<210> SEQ ID NO 471
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 10, 12, 13, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 14, 15, 16
<223> OTHER INFORMATION: /mod_base = "2'-hydroxy corresponding
      nucleoside"

<400> SEQUENCE: 471
ucccgucggc gcugaaucct t                                              21

<210> SEQ ID NO 472
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 6, 7, 8, 9, 11, 15, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 10, 12, 13, 14, 16, 17
<223> OTHER INFORMATION: /mod_base = "2'-hydroxy corresponding
      nucleoside"
```

-continued

```
<400> SEQUENCE: 472
cugaaucccg cggacgacct t                                              21

<210> SEQ ID NO 473
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 7, 11, 12, 13, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 8, 9, 10, 14, 16, 17, 19
<223> OTHER INFORMATION: /mod_base = "2'-hydroxy corresponding
      nucleoside"

<400> SEQUENCE: 473
agagucuaga cucguggugt t                                              21

<210> SEQ ID NO 474
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 7, 8, 10, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 11, 12, 13, 14
<223> OTHER INFORMATION: /mod_base = "2'-hydroxy corresponding
      nucleoside"

<400> SEQUENCE: 474
uccauacugc ggaacuccut t                                              21

<210> SEQ ID NO 475
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
```

```
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 9, 10, 11, 12, 14, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 7, 8, 13, 15, 16, 17, 19
<223> OTHER INFORMATION: /mod_base = "2'-hydroxy corresponding
      nucleoside"

<400> SEQUENCE: 475
gcgcugaauc ccgcggacgt t                                            21

<210> SEQ ID NO 476
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 9, 10, 11, 13, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 7, 8, 12, 14
<223> OTHER INFORMATION: /mod_base = "2'-hydroxy corresponding
      nucleoside"

<400> SEQUENCE: 476
aguguggauu cgcacuccut t                                            21

<210> SEQ ID NO 477
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 6, 7, 8, 10, 12, 13, 15, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 11, 14, 16, 17, 18
<223> OTHER INFORMATION: /mod_base = "2'-hydroxy corresponding
``` nucleoside"

<400> SEQUENCE: 477
cccugcucgu guuacaggct t                                    21

<210> SEQ ID NO 478
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 6, 7, 9, 13, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 8, 10, 11, 12, 14, 15, 19
<223> OTHER INFORMATION: /mod_base = "2'-hydroxy corresponding
      nucleoside"

<400> SEQUENCE: 478
gaaucccgcg gacgacccgt t                                    21

<210> SEQ ID NO 479
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 5, 7, 9, 10, 11, 12, 16, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 8, 13, 14, 15, 17, 18
<223> OTHER INFORMATION: /mod_base = "2'-hydroxy corresponding
      nucleoside"

<400> SEQUENCE: 479
aagcugugcc uugggguggct t                                   21

<210> SEQ ID NO 480
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:

```
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 9, 11, 13, 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 12, 15, 17, 18, 19
<223> OTHER INFORMATION: /mod_base = "2'-hydroxy corresponding
      nucleoside"

<400> SEQUENCE: 480
gcccugcucg uguuacaggt t                                              21

<210> SEQ ID NO 481
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 11, 13, 14, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 12, 15, 16, 17
<223> OTHER INFORMATION: /mod_base = "2'-hydroxy corresponding
      nucleoside"

<400> SEQUENCE: 481
gucccgucgg cgcugaauct t                                              21

<210> SEQ ID NO 482
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 7, 8, 11, 13, 14, 15, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
```

```
<222> LOCATION: 6, 9, 10, 12, 18, 19
<223> OTHER INFORMATION: /mod_base = "2'-hydroxy corresponding
      nucleoside"

<400> SEQUENCE: 482
aucuuaucaa cacuuccggt t                                              21

<210> SEQ ID NO 483
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 5, 6, 9, 11, 12, 13, 14, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 10, 16, 17, 18, 19
<223> OTHER INFORMATION: /mod_base = "2'-hydroxy corresponding
      nucleoside"

<400> SEQUENCE: 483
cuuaucaaca cuuccggaat t                                              21

<210> SEQ ID NO 484
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 484
cuuaucaaca cuuccggaat                                                20

<210> SEQ ID NO 485
<211> LENGTH: 21
<212> TYPE: DNA
<213> ORGANISM: Artificial sequence
<220> FEATURE:
<223> OTHER INFORMATION: Description of the artificial sequence:
```

```
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 8, 11, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 14, 15, 16, 17, 18, 19
<223> OTHER INFORMATION: /mod_base = "2'-hydroxy corresponding
      nucleoside"

<400> SEQUENCE: 485
aaacgggcaa cauaccuugt t                                              21

<210> SEQ ID NO 486
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 486
taccaauuua ugccuacagt t                                              21

<210> SEQ ID NO 487
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 6, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 7, 8, 9, 10, 11, 12, 13, 14, 15, 17, 18,
      19
<223> OTHER INFORMATION: /mod_base = "2'-hydroxy corresponding
``` nucleoside"

<400> SEQUENCE: 487
uaugauaaaa cgccgcagat t                                              21

<210> SEQ ID NO 488
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 488
taugauaaaa cgccgcagat t                                              21

<210> SEQ ID NO 489
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 14, 15, 16, 17,
      18, 19
<223> OTHER INFORMATION: /mod_base = "2'-hydroxy corresponding
      nucleoside"

<400> SEQUENCE: 489
gagaugauua ggcagaggut t                                              21

<210> SEQ ID NO 490
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"

-continued

```
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 490
tacaaauggc acuaguaaat t                                              21

<210> SEQ ID NO 491
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 491
tagaugauua ggcagaggut t                                              21

<210> SEQ ID NO 492
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4, 9, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 10, 11, 12, 13, 14, 16, 18, 19
<223> OTHER INFORMATION: /mod_base = "2'-hydroxy corresponding
      nucleoside"

<400> SEQUENCE: 492
gaccaauuua ugccuacagt t                                              21

<210> SEQ ID NO 493
<211> LENGTH: 21
<212> TYPE: DNA
<213> ORGANISM: Artificial sequence
<220> FEATURE:
```

```
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4, 14, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 15, 16, 17, 19
<223> OTHER INFORMATION: /mod_base = "2'-hydroxy corresponding
      nucleoside"

<400> SEQUENCE: 493
ugauaaaacg ccgcagacat t                                              21

<210> SEQ ID NO 494
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 494
tgauaaaacg ccgcagacat t                                              21

<210> SEQ ID NO 495
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 12, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 13, 14, 16, 17, 19
<223> OTHER INFORMATION: /mod_base = "2'-hydroxy corresponding
``` nucleoside"

<400> SEQUENCE: 495
ugaacaaaug gcacuaguat t                                              21

<210> SEQ ID NO 496
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 496
tgaacaaaug gcacuaguat t                                              21

<210> SEQ ID NO 497
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 497
tgcagaggug aaaaaguugt t                                              21

<210> SEQ ID NO 498
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 13
<223> OTHER INFORMATION: /mod_base = "2'-O-methyl corresponding
      nucleoside"
<220> FEATURE:

```
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 14, 15, 16, 17,
      18, 19
<223> OTHER INFORMATION: /mod_base = "2'-hydroxy corresponding
      nucleoside"

<400> SEQUENCE: 498
cgaaccacug aacaaauggt t                                              21

<210> SEQ ID NO 499
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 9, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 14, 15, 16, 17,
      18, 19
<223> OTHER INFORMATION: /mod_base = "2'-hydroxy corresponding
      nucleoside"

<400> SEQUENCE: 499
ugcgucagca aacacuuggt t                                              21

<210> SEQ ID NO 500
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 500
tgcgucagca aacacuuggt t                                              21

<210> SEQ ID NO 501
<211> LENGTH: 21
<212> TYPE: DNA
<213> ORGANISM: Artificial sequence
```

```
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 501
tgaaccacug aacaaauggt t                                              21

<210> SEQ ID NO 502
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 10, 13, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 11, 12, 14, 15, 17, 18, 19
<223> OTHER INFORMATION: /mod_base = "2'-hydroxy corresponding
      nucleoside"

<400> SEQUENCE: 502
aacaaauggc acuaguaaat t                                              21

<210> SEQ ID NO 503
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 503
```

```
tgaugauuag gcagaggugt t                                              21
```

<210> SEQ ID NO 504
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 4, 7, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 8, 9, 10, 11, 12, 13, 14, 15, 16, 18, 19
<223> OTHER INFORMATION: /mod_base = "2'-hydroxy corresponding
      nucleoside"

<400> SEQUENCE: 504

```
cacuaguaaa cugagccagt t                                              21
```

<210> SEQ ID NO 505
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 505

```
taacgggcaa cauaccuugt t                                              21
```

<210> SEQ ID NO 506
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"

```
<220> FEATURE:
<221> NAME/KEY: modified_base
<222> LOCATION: 21
<223> OTHER INFORMATION: /mod_base = "5'-phosphorothioate thymidine"

<400> SEQUENCE: 506
tacuaguaaa cugagccagt t                                              21

<210> SEQ ID NO 507
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 11, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 12, 14, 15, 16, 17, 18,
      19
<223> OTHER INFORMATION: /mod_base = "2'-hydroxy corresponding
      nucleoside"

<400> SEQUENCE: 507
aauuuaugcc uacagccuct t                                              21

<210> SEQ ID NO 508
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 10, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 14, 15, 16, 17, 18,
      19
<223> OTHER INFORMATION: /mod_base = "2'-hydroxy corresponding
      nucleoside"

<400> SEQUENCE: 508
aaauggcacu aguaaacugt t                                              21

<210> SEQ ID NO 509
<211> LENGTH: 21
<212> TYPE: DNA
```

```
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 10, 13, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 11, 12, 14, 16, 17, 18, 19
<223> OTHER INFORMATION: /mod_base = "2'-hydroxy corresponding
      nucleoside"

<400> SEQUENCE: 509
acaaacgggc aacauaccut t                                              21

<210> SEQ ID NO 510
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 510
tggacaaacg ggcaacauat t                                              21

<210> SEQ ID NO 511
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 511
```
tauuuaugcc uacagccuct t                                    21

<210> SEQ ID NO 512
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 16, 17,
      18, 19
<223> OTHER INFORMATION: /mod_base = "2'-hydroxy corresponding
      nucleoside"

<400> SEQUENCE: 512
augauaaaac gccgcagact t                                    21

<210> SEQ ID NO 513
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 513
ggcagaggug aaaaaguugt t                                    21

<210> SEQ ID NO 514
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base

```
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 13, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 16, 17, 18,
      19
<223> OTHER INFORMATION: /mod_base = "2'-hydroxy corresponding
      nucleoside"

<400> SEQUENCE: 514
ugaagcgaag ugcacacggt t                                              21

<210> SEQ ID NO 515
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 515
tgaagcgaag ugcacacggt t                                              21

<210> SEQ ID NO 516
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 516
tacgggcaac auaccuugat t                                              21

<210> SEQ ID NO 517
```

```
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 517
taauggcacu aguaaacugt t                                          21

<210> SEQ ID NO 518
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
      19
<223> OTHER INFORMATION: /mod_base = "2'-hydroxy corresponding
      nucleoside"

<400> SEQUENCE: 518
aauugagaga aguccaccat t                                          21

<210> SEQ ID NO 519
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
```

-continued

```
<223> OTHER INFORMATION: /mod_base = "5'-phosphorothioate thymidine"

<400> SEQUENCE: 519
tcaaacgggc aacauaccut t                                              21

<210> SEQ ID NO 520
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 8, 11, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 13, 14, 15, 16, 18,
      19
<223> OTHER INFORMATION: /mod_base = "2'-hydroxy corresponding
      nucleoside"

<400> SEQUENCE: 520
ccgccuguaa cacgagcagt t                                              21

<210> SEQ ID NO 521
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 13, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 14, 15, 17, 19
<223> OTHER INFORMATION: /mod_base = "2'-hydroxy corresponding
      nucleoside"

<400> SEQUENCE: 521
aggacaaacg ggcaacauat t                                              21

<210> SEQ ID NO 522
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
```

```
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 10, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 13, 14, 15, 16, 17, 18, 19
<223> OTHER INFORMATION: /mod_base = "2'-hydroxy corresponding
      nucleoside"

<400> SEQUENCE: 522
aacgggcaac auaccuugat t                                              21

<210> SEQ ID NO 523
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
      18, 19
<223> OTHER INFORMATION: /mod_base = "2'-hydroxy corresponding
      nucleoside"

<400> SEQUENCE: 523
uccggaagug uugauaagat t                                              21

<210> SEQ ID NO 524
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"
```

```
<400> SEQUENCE: 524
tccggaagug uugauaagat t                                              21

<210> SEQ ID NO 525
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 8, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 11, 13, 14, 15, 16, 17,
      18, 19
<223> OTHER INFORMATION: /mod_base = "2'-hydroxy corresponding
      nucleoside"

<400> SEQUENCE: 525
agaugauuag gcagaggugt t                                              21

<210> SEQ ID NO 526
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16,
      18, 19
<223> OTHER INFORMATION: /mod_base = "2'-hydroxy corresponding
      nucleoside"

<400> SEQUENCE: 526
aguccaagag uccucuuaut t                                              21

<210> SEQ ID NO 527
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
```

```
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 527
tugauaaaac gccgcagact t                                            21

<210> SEQ ID NO 528
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 15, 16, 17,
      18, 19
<223> OTHER INFORMATION: /mod_base = "2'-hydroxy corresponding
      nucleoside"

<400> SEQUENCE: 528
guccgcggga uucagcgcct t                                            21

<210> SEQ ID NO 529
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 529
ugagaucuuc ugcgacgcgt t                                            21
```

```
<210> SEQ ID NO 530
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 530
aaggucgguc guugacauut t                                               21

<210> SEQ ID NO 531
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4, 7, 10
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 8, 9, 11, 12, 13, 14, 15, 16, 17, 18,
      19
<223> OTHER INFORMATION: /mod_base = "2'-hydroxy corresponding
      nucleoside"

<400> SEQUENCE: 531
uggcacuagu aaacugagct t                                               21

<210> SEQ ID NO 532
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
```

```
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 532
tauugagaga aguccaccat t                                          21

<210> SEQ ID NO 533
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 533
ucuucugcga cgcggcgaut t                                          21

<210> SEQ ID NO 534
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 13, 14, 15, 16, 17, 18,
      19
<223> OTHER INFORMATION: /mod_base = "2'-hydroxy corresponding
      nucleoside"

<400> SEQUENCE: 534
gaaccacuga acaaauggct t                                          21

<210> SEQ ID NO 535
<211> LENGTH: 21
<212> TYPE: DNA
<213> ORGANISM: Artificial sequence
```

-continued

```
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 8, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 13, 14, 15, 16, 17, 18,
      19
<223> OTHER INFORMATION: /mod_base = "2'-hydroxy corresponding
      nucleoside"

<400> SEQUENCE: 535
aguuccgcag uauggaucgt t                                              21

<210> SEQ ID NO 536
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 12, 13, 14, 15, 16, 17, 18,
      19
<223> OTHER INFORMATION: /mod_base = "2'-hydroxy corresponding
      nucleoside"

<400> SEQUENCE: 536
gaugauuagg cagaggugat t                                              21

<210> SEQ ID NO 537
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 17
<223> OTHER INFORMATION: /mod_base = "2'-O-methyl corresponding
      nucleoside"
```

```
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
      18, 19
<223> OTHER INFORMATION: /mod_base = "2'-hydroxy corresponding
      nucleoside"

<400> SEQUENCE: 537
aaaauugaga gaaguccact t                                              21

<210> SEQ ID NO 538
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 9
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 10, 11, 12, 13, 14, 15, 16, 17,
      18, 19
<223> OTHER INFORMATION: /mod_base = "2'-hydroxy corresponding
      nucleoside"

<400> SEQUENCE: 538
cccaagaaua uggugaccct t                                              21

<210> SEQ ID NO 539
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 539
agaucuucug cgacgcggct t                                              21

<210> SEQ ID NO 540
<211> LENGTH: 21
<212> TYPE: DNA
```

```
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 540
ucugcgacgc ggcgauugat t                                              21

<210> SEQ ID NO 541
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 8, 12, 14, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 11, 13, 15, 16, 17, 19
<223> OTHER INFORMATION: /mod_base = "2'-hydroxy corresponding
      nucleoside"

<400> SEQUENCE: 541
aacgccgcag acacauccat t                                              21

<210> SEQ ID NO 542
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
```

```
<222> LOCATION: 1, 2, 3, 4, 5, 6, 7, 8, 9, 10, 11, 12, 13, 14, 16,
      17, 19
<223> OTHER INFORMATION: /mod_base = "2'-hydroxy corresponding
      nucleoside"

<400> SEQUENCE: 542
cuuggaggcu ugaacaguat t                                              21

<210> SEQ ID NO 543
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 9, 12, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 10, 11, 13, 14, 16, 17, 18, 19
<223> OTHER INFORMATION: /mod_base = "2'-hydroxy corresponding
      nucleoside"

<400> SEQUENCE: 543
acaaauggca cuaguaaact t                                              21

<210> SEQ ID NO 544
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 13, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 14, 15, 17, 18, 19
<223> OTHER INFORMATION: /mod_base = "2'-hydroxy corresponding
      nucleoside"

<400> SEQUENCE: 544
cugaacaaau ggcacuagut t                                              21

<210> SEQ ID NO 545
<211> LENGTH: 21
<212> TYPE: DNA
<213> ORGANISM: Artificial sequence
<220> FEATURE:
```

<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 545
gagaucuucu cgacgcggt t                                          21

<210> SEQ ID NO 546
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 13, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 15, 16,
      17, 19
<223> OTHER INFORMATION: /mod_base = "2'-hydroxy corresponding
      nucleoside"

<400> SEQUENCE: 546
cggaaguguu gauaagauat t                                          21

<210> SEQ ID NO 547
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 547
gggacugcga auuuuggcct t                                              21

<210> SEQ ID NO 548
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 10
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 11, 12, 13, 14, 15, 16, 17,
      18, 19
<223> OTHER INFORMATION: /mod_base = "2'-hydroxy corresponding
      nucleoside"

<400> SEQUENCE: 548
augauuaggc agaggugaat t                                              21

<210> SEQ ID NO 549
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 8, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 12, 13, 14, 15, 16, 17, 18,
      19
<223> OTHER INFORMATION: /mod_base = "2'-hydroxy corresponding
      nucleoside"

<400> SEQUENCE: 549
auggcacuag uaaacugagt t                                              21

<210> SEQ ID NO 550
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1

```
<223> OTHER INFORMATION: /mod_base = "nucleoside: lacks 5'-phosphate
      group"
<220> FEATURE:
<221> NAME/KEY: modified_base
<222> LOCATION: 7, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 14, 16, 17,
      19
<223> OTHER INFORMATION: /mod_base = "2'-hydroxy corresponding
      nucleoside"

<400> SEQUENCE: 550
agaggacaaa cgggcaacat t                                          21

<210> SEQ ID NO 551
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 8, 15, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 9, 10, 11, 12, 13, 14, 16, 17, 19
<223> OTHER INFORMATION: /mod_base = "2'-hydroxy corresponding
      nucleoside"

<400> SEQUENCE: 551
cacugaacaa auggcacuat t                                          21

<210> SEQ ID NO 552
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 6, 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 7, 8, 9, 10, 11, 13, 15, 16, 17, 18, 19
```

```
<223> OTHER INFORMATION: /mod_base = "2'-hydroxy corresponding
      nucleoside"

<400> SEQUENCE: 552
caauuuaugc cuacagccut t                                              21

<210> SEQ ID NO 553
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 11, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 12, 13, 14, 16, 18, 19
<223> OTHER INFORMATION: /mod_base = "2'-hydroxy corresponding
      nucleoside"

<400> SEQUENCE: 553
uaaaacgccg cagacacaut t                                              21

<210> SEQ ID NO 554
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 554
taaaacgccg cagacacaut t                                              21

<210> SEQ ID NO 555
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

```
<220> FEATURE:
<221> NAME/KEY: modified_base
<222> LOCATION: 3
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 555
ugcagaggug aagcgaagut t                                              21

<210> SEQ ID NO 556
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 17,
      18, 19
<223> OTHER INFORMATION: /mod_base = "2'-hydroxy corresponding
      nucleoside"

<400> SEQUENCE: 556
gugaagcgaa gugcacacgt t                                              21

<210> SEQ ID NO 557
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 14, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16,
      18, 19
```

```
<223> OTHER INFORMATION: /mod_base = "2'-hydroxy corresponding
      nucleoside"

<400> SEQUENCE: 557
auugagagaa guccaccact t                                              21

<210> SEQ ID NO 558
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 12, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 13, 14, 15, 17, 19
<223> OTHER INFORMATION: /mod_base = "2'-hydroxy corresponding
      nucleoside"

<400> SEQUENCE: 558
auaaaacgcc gcagacacat t                                              21

<210> SEQ ID NO 559
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 9, 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 10, 11, 13, 15, 16, 17, 18, 19
<223> OTHER INFORMATION: /mod_base = "2'-hydroxy corresponding
      nucleoside"

<400> SEQUENCE: 559
caaacgggca acauaccuut t                                              21

<210> SEQ ID NO 560
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
```

-continued

```
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 560
ccucaagguc ggucguugat t                                               21

<210> SEQ ID NO 561
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 561
guccaagagu ccucuuaugt t                                               21

<210> SEQ ID NO 562
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3
<223> OTHER INFORMATION: /mod_base = "2'-O-methyl corresponding
      nucleoside"
<220> FEATURE:
<221> NAME/KEY: modified_base
<222> LOCATION: 21
```

```
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 562
cucaaggucg gucguugact t                                              21

<210> SEQ ID NO 563
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 11, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 14, 15, 16,
      18, 19
<223> OTHER INFORMATION: /mod_base = "2'-hydroxy corresponding
      nucleoside"

<400> SEQUENCE: 563
cucuuguucc caagaauaut t                                              21

<210> SEQ ID NO 564
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9, 12, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 13, 14, 15, 16, 17, 19
<223> OTHER INFORMATION: /mod_base = "2'-hydroxy corresponding
      nucleoside"

<400> SEQUENCE: 564
cccgccugua acacgagcat t                                              21

<210> SEQ ID NO 565
```

```
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 565
uucugcgacg cggcgauugt t                                              21

<210> SEQ ID NO 566
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 566
gcuuggaggc uugaacagut t                                              21

<210> SEQ ID NO 567
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
``` nucleoside"

<400> SEQUENCE: 567
gaucuucugc gacgcggcgt t                                              21

<210> SEQ ID NO 568
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 15, 16, 17,
      18, 19
<223> OTHER INFORMATION: /mod_base = "2'-hydroxy corresponding
      nucleoside"

<400> SEQUENCE: 568
acgaaccacu gaacaaaugt t                                              21

<210> SEQ ID NO 569
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
      18, 19
<223> OTHER INFORMATION: /mod_base = "2'-hydroxy corresponding
      nucleoside"

<400> SEQUENCE: 569
ucguccgcgg gauucagcgt t                                              21

<210> SEQ ID NO 570
<211> LENGTH: 21
<212> TYPE: DNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate
    group"
<220> FEATURE:
<221> NAME/KEY: modified_base
<222> LOCATION: 2, 8, 18
<223> OTHER INFORMATION: /mod_base = "2'-O-methyl corresponding
    nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 9, 10, 11, 12, 13, 14, 15, 16, 17, 19
<223> OTHER INFORMATION: /mod_base = "2'-hydroxy corresponding
    nucleoside"

<400> SEQUENCE: 570
ccaagaauau ggugacccat t                                        21

<210> SEQ ID NO 571
<211> LENGTH: 21
<212> TYPE: DNA
<213> ORGANISM: Artificial sequence
<220> FEATURE:
<223> OTHER INFORMATION: Description of the artificial sequence:
    antisense strand of dsRNA
<220> FEATURE:
<221> NAME/KEY: modified_base
<222> LOCATION: 1
<223> OTHER INFORMATION: /mod_base = "nucleoside: lacks 5'-phosphate
    group"
<220> FEATURE:
<221> NAME/KEY: modified_base
<222> LOCATION: 3, 13
<223> OTHER INFORMATION: /mod_base = "2'-O-methyl corresponding
    nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 14, 15, 16, 17,
    18, 19
<223> OTHER INFORMATION: /mod_base = "2'-hydroxy corresponding
    nucleoside"

<400> SEQUENCE: 571
aguauggauc ggcagaggat t                                        21

<210> SEQ ID NO 572
<211> LENGTH: 21
<212> TYPE: DNA
<213> ORGANISM: Artificial sequence
<220> FEATURE:
<223> OTHER INFORMATION: Description of the artificial sequence:
    antisense strand of dsRNA
<220> FEATURE:
<221> NAME/KEY: modified_base
<222> LOCATION: 1
<223> OTHER INFORMATION: /mod_base = "nucleoside: lacks 5'-phosphate
    group"
<220> FEATURE:
<221> NAME/KEY: modified_base
<222> LOCATION: 1, 17
<223> OTHER INFORMATION: /mod_base = "2'-O-methyl corresponding
    nucleoside"
<220> FEATURE:
<221> NAME/KEY: modified_base
<222> LOCATION: 21

```
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 11, 12, 13, 14, 15, 16,
      18, 19
<223> OTHER INFORMATION: /mod_base = "2'-hydroxy corresponding
      nucleoside"

<400> SEQUENCE: 572
caaggucggu cguugacaut t                                              21

<210> SEQ ID NO 573
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 10, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 11, 12, 13, 15, 16, 17,
      18, 19
<223> OTHER INFORMATION: /mod_base = "2'-hydroxy corresponding
      nucleoside"

<400> SEQUENCE: 573
ugagaugauu aggcagaggt t                                              21

<210> SEQ ID NO 574
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 13, 15, 16, 17,
      18, 19
<223> OTHER INFORMATION: /mod_base = "2'-hydroxy corresponding
      nucleoside"

<400> SEQUENCE: 574
gaagcgaagu gcacacggut t                                              21
```

-continued

```
<210> SEQ ID NO 575
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 8, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 14, 15, 16, 17, 19
<223> OTHER INFORMATION: /mod_base = "2'-hydroxy corresponding
      nucleoside"

<400> SEQUENCE: 575
uccgcaguau ggaucggcat t                                              21

<210> SEQ ID NO 576
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 12, 13, 14, 15, 16, 17,
       18, 19
<223> OTHER INFORMATION: /mod_base = "2'-hydroxy corresponding
      nucleoside"

<400> SEQUENCE: 576
accacgaguc uagacucugt t                                              21

<210> SEQ ID NO 577
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
```

```
<222> LOCATION: 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15,
      16, 18, 19
<223> OTHER INFORMATION: /mod_base = "2'-hydroxy corresponding
      nucleoside"

<400> SEQUENCE: 577
agcuuggagg cuugaacagt t                                              21

<210> SEQ ID NO 578
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4, 10, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 11, 13, 14, 15, 16, 17, 18, 19
<223> OTHER INFORMATION: /mod_base = "2'-hydroxy corresponding
      nucleoside"

<400> SEQUENCE: 578
auuuaugccu acagccucct t                                              21

<210> SEQ ID NO 579
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 9, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 10, 12, 13, 14, 15, 16, 17, 18, 19
<223> OTHER INFORMATION: /mod_base = "2'-hydroxy corresponding
      nucleoside"

<400> SEQUENCE: 579
```
uuuaugccua cagccuccut t                                          21

<210> SEQ ID NO 580
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 580
aaauugagag aaguccacct t                                          21

<210> SEQ ID NO 581
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding
      nucleoside"

<400> SEQUENCE: 581
gcagagguga aaaaguugct t                                          21

<210> SEQ ID NO 582
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 582
tcgccuguaa cacgagcagt t    21

<210> SEQ ID NO 583
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 7, 14, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 15, 16, 18, 19
<223> OTHER INFORMATION: /mod_base = "2'-hydroxy corresponding nucleoside"

<400> SEQUENCE: 583
acugaacaaa uggcacuagt t    21

<210> SEQ ID NO 584
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 4, 7, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 8, 9, 10, 11, 12, 13, 14, 15, 16, 18, 19
<223> OTHER INFORMATION: /mod_base = "2'-hydroxy corresponding nucleoside"

<400> SEQUENCE: 584
ccgcaguaug gaucggcagt t                    21

<210> SEQ ID NO 585
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16,
      18, 19
<223> OTHER INFORMATION: /mod_base = "2'-hydroxy corresponding
      nucleoside"

<400> SEQUENCE: 585
ggugaagcga agugcacact t                    21

<210> SEQ ID NO 586
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 10, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 11, 12, 14, 15, 16, 17,
      18, 19
<223> OTHER INFORMATION: /mod_base = "2'-hydroxy corresponding
      nucleoside"

<400> SEQUENCE: 586
gcccgccugu aacacgagct t                    21

<210> SEQ ID NO 587
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1

```
<223> OTHER INFORMATION: /mod_base = "nucleoside: lacks 5'-phosphate
      group"
<220> FEATURE:
<221> NAME/KEY: modified_base
<222> LOCATION: 11, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 14, 15, 17,
      18, 19
<223> OTHER INFORMATION: /mod_base = "2'-hydroxy corresponding
      nucleoside"

<400> SEQUENCE: 587
gaaguguuga uaagauaggt t                                            21

<210> SEQ ID NO 588
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 588
ugcgacgcgg cgauugagat t                                            21

<210> SEQ ID NO 589
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9, 11
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 12, 13, 14, 15, 16, 17,
      18, 19
<223> OTHER INFORMATION: /mod_base = "2'-hydroxy corresponding
      nucleoside"

<400> SEQUENCE: 589
```
ugagaaggca cagacgggct t    21

<210> SEQ ID NO 590
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 12, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 13, 14, 15, 16,
      18, 19
<223> OTHER INFORMATION: /mod_base = "2'-hydroxy corresponding
      nucleoside"

<400> SEQUENCE: 590
ggaaguguug auaagauagt t    21

<210> SEQ ID NO 591
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 14, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 15, 16, 18, 19
<223> OTHER INFORMATION: /mod_base = "2'-hydroxy corresponding
      nucleoside"

<400> SEQUENCE: 591
gaggacaaac gggcaacaut t    21

<210> SEQ ID NO 592
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1

```
<223> OTHER INFORMATION: /mod_base = "nucleoside: lacks 5'-phosphate
      group"
<220> FEATURE:
<221> NAME/KEY: modified_base
<222> LOCATION: 4, 12, 15, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 13, 14, 16, 18, 19
<223> OTHER INFORMATION: /mod_base = "2'-hydroxy corresponding
      nucleoside"

<400> SEQUENCE: 592
ggacaaacgg gcaacauact t                                              21

<210> SEQ ID NO 593
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 593
gugcagaggu gaagcgaagt t                                              21

<210> SEQ ID NO 594
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15,
```

17, 19
<223> OTHER INFORMATION: /mod_base = "2'-hydroxy corresponding
      nucleoside"

<400> SEQUENCE: 594
aggugaagcg aagugcacat t                                              21

<210> SEQ ID NO 595
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 595
cgggacugcg aauuuuggct t                                              21

<210> SEQ ID NO 596
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 10, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 13, 14, 15, 17, 18, 19
<223> OTHER INFORMATION: /mod_base = "2'-hydroxy corresponding
      nucleoside"

<400> SEQUENCE: 596
cgccuguaac acgagcaggt t                                              21

<210> SEQ ID NO 597
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate

```
           group"
<220> FEATURE:
<221> NAME/KEY: modified_base
<222> LOCATION: 11, 13, 18
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 14, 15, 16, 17, 19
<223> OTHER INFORMATION: /mod_base = "2'-hydroxy corresponding
       nucleoside"

<400> SEQUENCE: 597
agugcgaauc cacacuccat t                                              21

<210> SEQ ID NO 598
<211> LENGTH: 21
<212> TYPE: DNA
<213> ORGANISM: Artificial sequence
<220> FEATURE:
<223> OTHER INFORMATION: Description of the artificial sequence:
       antisense strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 6
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16,
       17, 18, 19
<223> OTHER INFORMATION: /mod_base = "2'-hydroxy corresponding
       nucleoside"

<400> SEQUENCE: 598
ugccucaagg ucggucguut t                                              21

<210> SEQ ID NO 599
<211> LENGTH: 21
<212> TYPE: DNA
<213> ORGANISM: Artificial sequence
<220> FEATURE:
<223> OTHER INFORMATION: Description of the artificial sequence:
       antisense strand of dsRNA
<220> FEATURE:
<221> NAME/KEY: modified_base
<222> LOCATION: 1
<223> OTHER INFORMATION: /mod_base = "nucleoside: lacks 5'-phosphate
       group"
<220> FEATURE:
<221> NAME/KEY: modified_base
<222> LOCATION: 2, 10
<223> OTHER INFORMATION: /mod_base = "2'-O-methyl corresponding
       nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 11, 12, 13, 14, 15, 16, 17,
       18, 19
```

```
<223> OTHER INFORMATION: /mod_base = "2'-hydroxy corresponding
      nucleoside"

<400> SEQUENCE: 599
ccacgagucu agacucugut t                                              21

<210> SEQ ID NO 600
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 600
cuucugcgac gcggcgauut t                                              21

<210> SEQ ID NO 601
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 11, 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 12, 13, 15, 17, 18, 19
<223> OTHER INFORMATION: /mod_base = "2'-hydroxy corresponding
      nucleoside"

<400> SEQUENCE: 601
gacaaacggg caacauacct t                                              21

<210> SEQ ID NO 602
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
```

```
<220> FEATURE:
<221> NAME/KEY: modified_base
<222> LOCATION: 6, 9
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 13, 14, 15, 16, 17,
      18, 19
<223> OTHER INFORMATION: /mod_base = "2'-hydroxy corresponding
      nucleoside"

<400> SEQUENCE: 602
uuccgcagua uggaucggct t                                              21

<210> SEQ ID NO 603
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 13, 15, 16, 17,
      18, 19
<223> OTHER INFORMATION: /mod_base = "2'-hydroxy corresponding
      nucleoside"

<400> SEQUENCE: 603
aguguugaua agauagggct t                                              21

<210> SEQ ID NO 604
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 8, 11, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 9, 10, 12, 13, 15, 16, 17, 18, 19
<223> OTHER INFORMATION: /mod_base = "2'-hydroxy corresponding
``` nucleoside"

<400> SEQUENCE: 604
caaauggcac uaguaaacut t                                          21

<210> SEQ ID NO 605
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16,
      17, 19
<223> OTHER INFORMATION: /mod_base = "2'-hydroxy corresponding
      nucleoside"

<400> SEQUENCE: 605
ucaaggucgg ucguugacat t                                          21

<210> SEQ ID NO 606
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 606
cuagaaaauu gagagaagut t                                          21

<210> SEQ ID NO 607
<211> LENGTH: 21
<212> TYPE: DNA
<213> ORGANISM: Artificial sequence
<220> FEATURE:
<223> OTHER INFORMATION: Description of the artificial sequence:

-continued

```
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 607
gacaaaggac gucccgcgct t                                          21

<210> SEQ ID NO 608
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 8, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 14, 15, 17, 18, 19
<223> OTHER INFORMATION: /mod_base = "2'-hydroxy corresponding
      nucleoside"

<400> SEQUENCE: 608
aguccaccac gagucuagat t                                          21

<210> SEQ ID NO 609
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9, 12
<223> OTHER INFORMATION: /mod_base = "2'-O-methyl corresponding
      nucleoside"
<220> FEATURE:
<221> NAME/KEY: modified_base
<222> LOCATION: 21
```

```
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 13, 14, 15, 16, 17,
      18, 19
<223> OTHER INFORMATION: /mod_base = "2'-hydroxy corresponding
      nucleoside"

<400> SEQUENCE: 609
gaguuccgca guauggauct t                                              21

<210> SEQ ID NO 610
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 5, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 6, 7, 8, 9, 10, 11, 12, 13, 14, 16, 17, 18, 19
<223> OTHER INFORMATION: /mod_base = "2'-hydroxy corresponding
      nucleoside"

<400> SEQUENCE: 610
gcaguaugga ucggcagagt t                                              21

<210> SEQ ID NO 611
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 6, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 7, 8, 9, 10, 11, 12, 13, 14, 15, 17, 18, 19
<223> OTHER INFORMATION: /mod_base = "2'-hydroxy corresponding
      nucleoside"

<400> SEQUENCE: 611
cgcaguaugg aucggcagat t                                              21
```

-continued

```
<210> SEQ ID NO 612
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 4, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 7, 8, 9, 10, 11, 12, 13, 15, 16, 17, 18, 19
<223> OTHER INFORMATION: /mod_base = "2'-hydroxy corresponding
      nucleoside"

<400> SEQUENCE: 612
caguauggau cggcagaggt t                                           21

<210> SEQ ID NO 613
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 613
accgcguaaa gagaggugct t                                           21

<210> SEQ ID NO 614
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
```

```
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 614
gcgaggcgag ggaguucuut t                                              21

<210> SEQ ID NO 615
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 615
cugcgaggcg agggaguuct t                                              21

<210> SEQ ID NO 616
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 616
gcccuagaaa auugagagat t                                              21

<210> SEQ ID NO 617
<211> LENGTH: 21
<212> TYPE: DNA
<213> ORGANISM: Artificial sequence
<220> FEATURE:
```

```
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 617
cguaaagaga ggugcgccct t                                              21

<210> SEQ ID NO 618
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 7, 10
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 13, 14, 15, 16, 17,
      18, 19
<223> OTHER INFORMATION: /mod_base = "2'-hydroxy corresponding
      nucleoside"

<400> SEQUENCE: 618
guuccgcagu auggaucggt t                                              21

<210> SEQ ID NO 619
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
```

```
<222> LOCATION: 1..19
<223> OTHER INFORMATION: /mod_base = "2'-hydroxy corresponding
      nucleoside"

<400> SEQUENCE: 619
ucugcgaggc gagggaguut t                                              21

<210> SEQ ID NO 620
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 13, 14, 15, 16, 17,
      18, 19
<223> OTHER INFORMATION: /mod_base = "2'-hydroxy corresponding
      nucleoside"

<400> SEQUENCE: 620
guauggaucg gcagaggagt t                                              21

<210> SEQ ID NO 621
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 13, 15, 16, 17,
      18, 19
<223> OTHER INFORMATION: /mod_base = "2'-hydroxy corresponding
      nucleoside"

<400> SEQUENCE: 621
gagugcgaau ccacacucct t                                              21

<210> SEQ ID NO 622
<211> LENGTH: 21
<212> TYPE: DNA
<213> ORGANISM: Artificial sequence
```

```
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding
      nucleoside"

<400> SEQUENCE: 622
guaaagagag gugcgcccgt t                                             21

<210> SEQ ID NO 623
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 623
gcgacgcggc gauugagact t                                             21

<210> SEQ ID NO 624
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 10, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
```

<222> LOCATION: 1, 2, 3, 4, 5, 6, 7, 8, 9, 11, 12, 14, 15, 16, 17, 18, 19
<223> OTHER INFORMATION: /mod_base = "2'-hydroxy corresponding nucleoside"

<400> SEQUENCE: 624
ggaguuccgc aguauggaut t                                           21

<210> SEQ ID NO 625
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 6
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 625
ccgcguaaag agaggugcgt t                                           21

<210> SEQ ID NO 626
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 5
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 626
gccucaaggu cggucguugt t                                           21

<210> SEQ ID NO 627
<211> LENGTH: 21
<212> TYPE: DNA

<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 12, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 11, 13, 14, 16, 17, 18, 19
<223> OTHER INFORMATION: /mod_base = "2'-hydroxy corresponding
      nucleoside"

<400> SEQUENCE: 627
uaggaguucc gcaguauggt t                                           21

<210> SEQ ID NO 628
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
      17, 19
<223> OTHER INFORMATION: /mod_base = "2'-hydroxy corresponding
      nucleoside"

<400> SEQUENCE: 628
gggucguccg cgggauucat t                                           21

<210> SEQ ID NO 629
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:

```
<221> NAME/KEY: modified_base
<222> LOCATION: 1..19
<223> OTHER INFORMATION: /mod_base = "2'-hydroxy corresponding
      nucleoside"

<400> SEQUENCE: 629
ugcgaggcga gggaguucut t                                           21

<210> SEQ ID NO 630
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 4
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 630
gcguaaagag aggugcgcct t                                           21

<210> SEQ ID NO 631
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16,
      17, 18, 19
<223> OTHER INFORMATION: /mod_base = "2'-hydroxy corresponding
      nucleoside"

<400> SEQUENCE: 631
cgcguaaaga gaggugcgct t                                           21

<210> SEQ ID NO 632
<211> LENGTH: 21
<212> TYPE: DNA
```

<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 632
gucguccgcg ggauucagct t                                           21

<210> SEQ ID NO 633
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding
      nucleoside"

<400> SEQUENCE: 633
gcagagguga agcgaagugt t                                           21

<210> SEQ ID NO 634
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"

```
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 634
cugcgacgcg gcgauugagt t                                              21

<210> SEQ ID NO 635
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16, 17,
      18, 19
<223> OTHER INFORMATION: /mod_base = "2'-hydroxy corresponding
      nucleoside"

<400> SEQUENCE: 635
ggauucagcg ccgacgggat t                                              21

<210> SEQ ID NO 636
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
      18, 19
<223> OTHER INFORMATION: /mod_base = "2'-hydroxy corresponding
      nucleoside"

<400> SEQUENCE: 636
ggucguccgc gggauucagt t                                              21

<210> SEQ ID NO 637
<211> LENGTH: 21
```

```
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 4, 12
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 7, 8, 9, 10, 11, 13, 14, 15, 16, 17, 18, 19
<223> OTHER INFORMATION: /mod_base = "2'-hydroxy corresponding
      nucleoside"

<400> SEQUENCE: 637
caccacgagu cuagacucut t                                           21

<210> SEQ ID NO 638
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 11, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 15, 16, 17,
      18, 19
<223> OTHER INFORMATION: /mod_base = "2'-hydroxy corresponding
      nucleoside"

<400> SEQUENCE: 638
aggaguuccg caguauggat t                                           21

<210> SEQ ID NO 639
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 14
<223> OTHER INFORMATION: /mod_base = "2'-O-methyl corresponding
``` nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16, 17,
      18, 19
<223> OTHER INFORMATION: /mod_base = "2'-hydroxy corresponding
      nucleoside"

<400> SEQUENCE: 639
cguccgcggg auucagcgct t                                          21

<210> SEQ ID NO 640
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 14, 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 17,
      18, 19
<223> OTHER INFORMATION: /mod_base = "2'-hydroxy corresponding
      nucleoside"

<400> SEQUENCE: 640
aggagugcga auccacacut t                                          21

<210> SEQ ID NO 641
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 9, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 13, 14, 16, 17, 18, 19
<223> OTHER INFORMATION: /mod_base = "2'-hydroxy corresponding
      nucleoside"

<400> SEQUENCE: 641
gccuguaaca cgagcagggt t                                              21

<210> SEQ ID NO 642
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 642
cgggucgucc gcgggauuct t                                              21

<210> SEQ ID NO 643
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 7, 12, 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 8, 9, 10, 11, 13, 15, 16, 17, 18, 19
<223> OTHER INFORMATION: /mod_base = "2'-hydroxy corresponding
      nucleoside"

<400> SEQUENCE: 643
gccacccaag gcacagcuut t                                              21

<210> SEQ ID NO 644
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5, 8, 14
<223> OTHER INFORMATION: /mod_base = "2'-O-methyl corresponding
      nucleoside"

```
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 15, 16, 17, 18, 19
<223> OTHER INFORMATION: /mod_base = "2'-hydroxy corresponding
      nucleoside"

<400> SEQUENCE: 644
ccuguaacac gagcagggct t                                              21

<210> SEQ ID NO 645
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 5
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 17,
      18, 19
<223> OTHER INFORMATION: /mod_base = "2'-hydroxy corresponding
      nucleoside"

<400> SEQUENCE: 645
gauucagcgc cgacgggact t                                              21

<210> SEQ ID NO 646
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 14
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16, 17,
      18, 19
<223> OTHER INFORMATION: /mod_base = "2'-hydroxy corresponding
      nucleoside"

<400> SEQUENCE: 646
ccggaagugu ugauaagaut t                                              21
```

```
<210> SEQ ID NO 647
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 16
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding
      nucleoside"

<400> SEQUENCE: 647
uuccggaagu guugauaagt t                                              21

<210> SEQ ID NO 648
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
      nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 648
tuccggaagu guugauaagt t                                              21
```